US009993542B2

(12) United States Patent
Frazer

(10) Patent No.: US 9,993,542 B2
(45) Date of Patent: Jun. 12, 2018

(54) COMPOSITIONS AND USES THEREFOR

(71) Applicant: The University of Queensland, Queensland (AU)

(72) Inventor: Ian Hector Frazer, S. Lucia (AU)

(73) Assignee: Admedus Vaccines Pty Ltd., Brisbane, Queensland (AU)

( * ) Notice: Subject to any disclaimer, the term of this patent is extended or adjusted under 35 U.S.C. 154(b) by 0 days. days.

(21) Appl. No.: 14/454,341

(22) Filed: Aug. 7, 2014

(65) Prior Publication Data

US 2015/0132325 A1 May 14, 2015

Related U.S. Application Data

(62) Division of application No. 10/475,203, filed as application No. PCT/AU02/00486 on Apr. 18, 2002, now Pat. No. 8,858,951.

(30) Foreign Application Priority Data

Apr. 18, 2001 (AU) ...................................... PR4468

(51) Int. Cl.
| | |
|---|---|
| A61K 39/00 | (2006.01) |
| C07K 16/00 | (2006.01) |
| A61K 39/12 | (2006.01) |
| C07K 14/005 | (2006.01) |
| C07K 19/00 | (2006.01) |
| C12N 7/00 | (2006.01) |
| A61K 48/00 | (2006.01) |

(52) U.S. Cl.
CPC .............. *A61K 39/12* (2013.01); *A61K 39/00* (2013.01); *C07K 14/005* (2013.01); *C07K 19/00* (2013.01); *C12N 7/00* (2013.01); *A61K 48/00* (2013.01); *A61K 2039/5154* (2013.01); *A61K 2039/5156* (2013.01); *A61K 2039/5158* (2013.01); *A61K 2039/53* (2013.01); *A61K 2039/57* (2013.01); *C12N 2710/20022* (2013.01); *C12N 2710/20034* (2013.01)

(58) Field of Classification Search
None
See application file for complete search history.

(56) References Cited

U.S. PATENT DOCUMENTS

| | | | |
|---|---|---|---|
| 5,093,242 | A | 3/1992 | Bachmair et al. |
| 5,122,463 | A | 6/1992 | Varshaysky et al. |
| 5,612,179 | A | 3/1997 | Simons |
| 5,646,017 | A | 7/1997 | Bachmair et al. |
| 5,686,075 | A | 11/1997 | Taubman et al. |
| 6,019,984 | A | 2/2000 | Macinnes et al. |
| 6,319,503 | B1 | 11/2001 | Kenten et al. |
| 6,524,825 | B1 | 2/2003 | Mizzen et al. |
| 6,660,271 | B2 | 12/2003 | Kenten et al. |
| 2003/0148456 | A1 | 8/2003 | Mizzen et al. |

FOREIGN PATENT DOCUMENTS

| | | |
|---|---|---|
| WO | WO 93/02184 A1 | 2/1993 |
| WO | WO 95/20659 A1 | 8/1995 |
| WO | WO 95/31476 A1 | 11/1995 |
| WO | WO 96/19496 A1 | 6/1996 |
| WO | WO 97/05164 A1 | 2/1997 |
| WO | WO 98/23635 A1 | 6/1998 |
| WO | WO 99/02694 A1 | 1/1999 |
| WO | WO 99/07860 A1 | 2/1999 |
| WO | WO 99/42472 A1 | 8/1999 |
| WO | WO 99/42564 A2 | 8/1999 |
| WO | WO 00/354 78 A1 | 6/2000 |

OTHER PUBLICATIONS

Tobery et al. (Journal of Virology, 1999, vol. 162, p. 639-642) in IDS on Jul. 8, 2015.*
Hinkula et al. (Journal of Virology, 1997, vol. 71, p. 5528-5539) in IDS on Jul. 8, 2015.*
Delogu et al. (Infection and Immunity, published Jun. 2000, p. 3097-3102) in IDS on Jul. 8, 2015.*
Delogu et al. "DNA Vaccination against Tuberculosis: Expression of a Ubiquitin-Conjugated Tuberculosis Protein Enhances Antimycobacterial Immunity", Infection and Immunity, vol. 68, No. 6, published Jun. 2000, p. 3097-3102.
Tobery et al., "Cutting Edge: Induction of Enhanced CTL-Dependent Protective Immunity in Vivo by N-End Rule Targeting of a Model Tumor Antigen", Journal of Immunology, 1999, vol. 162, p. 639-642.
Hinkula et al., "Recognition of Prominent Viral Epitopes Induced by Immunization with Human Immunodeficiency Virus Type 1 Regulatory Genes", Journal of Virology, 1997, vol. 71, No. 7, p. 5528-5539.
Dietrich et al., "Listeriolysin—a useful cytolisin", Trends in Immunology, vol. 9, No. 4, Apr. 2001, 1 page).
Schiller et al. Journal of National Cancer Institute, 2000, p. 49-54, of record on Mar. 6, 2007.
Tobery et al., "Targeting of HIV-1 Antigen for Rapid Intracellular Degradation Enhances Cytotoxic T Lymphocyte (CTL) Recognition and the Induction of De Novo CTL Responses in vivo after Immunization", J. Exp. Med. 1997, vol. 185, No. 5, p. 909-920.
Schiller et al., "Papillomavirus-Like Particle Vaccines", Journal of the National Cancer Institute Monographs, No. 28, 2000, p. 50-54.
Shedlock et al., "DNA vaccination: antigen presentation and the induction of immunity", Journal of Leukocyte Biology, 2000, vol. 68, p. 793-806.

(Continued)

*Primary Examiner* — Agnieszka Boesen

(57) ABSTRACT

The invention is directed to the use of (i) a first antigen corresponding to a target antigen of interest, together with (ii) a second antigen, corresponding to a modified form of the target antigen, whose rate of intracellular proteolytic degradation is increased, enhanced or otherwise elevated relative to the first antigen, in compositions and methods for inducing both humoral and cellular immunity in an individual. The ability to provide compositions, which are capable of inducing both host-protective antibody and cell-mediated immune responses, facilitates the generation of immunogenic compositions capable of combating, inter alia, conditions that have long latency periods and, therefore, benefit from the dual approach of prophylaxis and therapy in one delivery.

18 Claims, 5 Drawing Sheets

(56) References Cited

OTHER PUBLICATIONS

Delogu et al., "DNA Vaccination against Tuberculosis: Expression of a Ubiquitin-Conjugated Tuberculosis Protein Enhances Antimycobacterial Immunity", Infection and Immunity, 2000, vol. 68, No. 6, p. 3097-3102.
Andre et al., "Increased Immune Response Elicited by DNA Vaccination with a Synthetic gp120 Sequence with Optimized Codon Usage", 1998, Journal of Virology, vol. 72, No. 2, p. 1497-1503.
Barry et al., "Biological Features of Genetic Immunization", 1997, Vaccine, vol. 15, No. 8, p. 788-791.
Donnelly et al., "Protection Against Papillomavirus with a Polynucleotide Vaccine", 1996, Journal of Infectious Diseases,vol. 173, p. 314-320.
Dupuy et al., "Nasal Immunization of Mice with Human Papillomavirus Type 16 (HPV-16) Virus-Like Particles or with the HPV-16 L1 Gene Elicits Specific Cytotoxic T Lymphocytes in Vaginal Draining Lymph Nodes", 1999, Journal of Virology, vol. 73, No. 11, p. 9063-9071.
Fu et al., "Induction of MHC class i-restricted CTL response by DNA immunication with ubiquitin-influenza virus nucleoprotein fusion antigens",1998, Vaccine, vol. 16, No. 18, p. 1711-1717.
Hines et al., "Prospects for human papillomavirus vaccine development emerging HPV vaccines", 1998, Gynecologic oncology and pathology, vol. 10, p. 15-19.
Lin et al., 1996, "Treatment of Established Tumors with a Novel Vaccine that Enhances Major Histocompatibility Class II Presentation of Tumor Antigen", Cancer Research, vol. 56, p. 21-26.
Liu et al., "Papillomavirus Virus-Like Particles for the Delivery of Multiple Cytotoxic T Cell Epitopes", 2000, Virology, 273, p. 374-382.
Liu et al., "Polynucleotide viral vaccines: codon optimisation and ubiquitin conjugation enhances prophylactic and therapeutic efficacy", 2002, Vaccine, vol. 20, p. 862-869.
Peng et al., "Papillomavirus Virus-like Particles Can Deliver CTL Epitopes to the MHC Class I Pathway", 1998, Virology, vol. 240, p. 147-157.
Penrose et al., "Proteasome-Mediated Degradation of the Papillimavirus E2-TA Protein is Regulated by Phosphorylation and Can Modulate Viral Genome Copy Number", 2000, Journal of Virology, vol. 74, No. 13, p. 6031-6038.
Schreckenberger et al., "Induction of an HPV 6bL1-specific mucosal IgA response by DNA immunization", 2000, Vaccine 19, p. 227-233.
Small et al., 2000, J. Clin. Oncol. 18(23):3894-3903.
Tindle et al., "Chimeric Hepatitis B Core Antigen Particles Containing B- and Th-Epitopes of Human Papillomavirus Type 16 E7 Protein Induce Specific Antibody and T-Helper Responses in Immunised Mice", 1994, Virology, vol. 200, p. 547-557.
Tobery et al., 1997, J. Exp. Med. 185:909-920.
Wu et al., "Deoxyribonucleic Acid Vaccines Encoding Antigens With Rapid Proteasome-Dependent Degradation Are Highly Efficient Inducers of Cytolytic L Lymphocytes", 1997, J. Immunol, 159:6037-6043.
Xiang et al., "An Autologous oral DNA vaccine protects against murine melanoma", 2000, Proc. Natl., Acad. Sci. U.S.A, vol. 97, No. 10, p. 5492-5497.
Zhou et al., "Papillomavirus Capsid Protein Expression Level Depends on the Match between Codon Usage and tRNA Availability", 1999, Journal of Virology, vol. 73, No. 6, p. 4972-4982.
Bachmair, A. et al., "In Vivo Half-Life of a Protein is a Function of Its Amino-Terminal Residue," Science, vol. 234, Research Articles, Oct. 10, 1996, pp. 179-186.
Bachmair, A. et al., "The Degradation Signal in a Short-Lived Protein," Cell vol. 56, Mar. 24, 1989, pp. 1019-1032.
Davydov, I. et al., "RGS4 Is Arginylated and Degraded by the N-end Rule Pathway in Vitro," The Journal of Biological Chemistry, vol. 275, No. 30, Jul. 28, 2000, pp. 22931-22941.
Hochstrasser, M. et al., "In Vivo Degradation of a Transcriptional Regulator: The Yeast α2 Repressor," Cell, vol. 61, May 18, 1990, pp. 697-708.
Mayer, R. et al., "Ubiquitin Superfolds: Intrinsic and Attachable Regulators of Cellular Activities," Currently Biology Ltd. ISSN 1359-0278, Oct. 1, 1998, 3 pages.
Townsend, A. et al., "Defective Presentation to Class I-Restricted Cytotoxic T Lymphocytes in Vaccinia-Infected Cells is Overcome by Enhanced Degradation of Antigen," J. Exp. Med., vol. 168, Oct. 1998, pp. 1211-1224.
Varshavsky, A. et al., "The Ubiquitin System and the N-End Rule Pathway," Biol. Chem., vol. 381, Oct. 2000, pp. 779-789.
Xiang, R. et al., "An Autologous Oral DNA Vaccine Protects Against Murine Melanoma," PNAS, vol. 97, No. 10, May 9, 2000, pp. 5492-5497; with Correction published Nov. 7, 2000, vol. 97, No. 23, pp. 12932.

\* cited by examiner

COMPOSITIONS AND USES THEREFOR

CROSS REFERENCE TO RELATED APPLICATIONS

This application is a divisional application of U.S. application Ser. No. 10/475,203, filed May 26, 2004, which is a national stage entry under 35 U.S.C. § 371 of PCT/AU2002/00486, filed Apr. 18, 2002, which claims the benefit of Australian Provisional Application number PR4468, filed Apr. 18, 2001, each of which is incorporated by reference in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is DAVI_013_01US_ST25.txt. The text file is about 132 KB, was created on Jan. 20, 2015, and is being submitted electronically via EFS-Web.

FIELD OF THE INVENTION

THIS INVENTION relates generally to compositions and methods for preventing and treating a disease or condition. More particularly, the present invention contemplates a method for the manufacture of a medicament exhibiting increased efficacy in prophylactic and therapeutic applications. Even more particularly, the present invention provides molecules which are capable of inducing both humoral and cellular immunity and provides for their use as a means for eliciting such immunity in an individual. The present invention further contemplates methods for cell-specific or tissue-targeted delivery of polynucleotide and/or polypeptide immunogens, capable of inducing simultaneously neutralising antibody and cell-mediated immune responses. Cells or tissues containing the polynucleotides also form part of the present invention. The ability to provide compositions capable of inducing both host-protective antibody and cell-mediated immune responses facilitates the generation of immunogenic compositions capable of combating, inter alia, conditions that have long latency periods and, therefore, benefit from the dual approach of prophylaxis and therapy in one delivery.

Bibliographic details of the publications numerically referred to in this specification are collected at the end of the description.

BACKGROUND OF THE INVENTION

New approaches for intervention in virally-induced disease are always sought after. Interest has been shown in adapting gene therapy for use in delivery of DNA immunogens to target cells and tissues. Success in this endeavour has been limited, however, partly because selective delivery of genes to target tissues has proven to be extremely difficult, and partly because success is dependent upon being able to predictably elicit either a specific antibody response or a cell-mediated response or both. Which response is desired, depends on the nature of the presenting problem.

While use of tissue-specific promoters to target gene therapy has been effective in some animal models, it has proven less so in man and selective tissue-specific promoters are not available for a wide range of tissues. Gene delivery systems such as vectors are not themselves tissue selective. Viral vectors, such as retroviruses and adenovirus, may be used and are to some extent selective. However, many vector systems are by their nature unable to produce stable integrants. Moreover, some also invoke immune responses themselves, thereby precluding predictable and effective immunological intervention.

A further reason why gene therapy has proven to be difficult is the unpredictability of the kind of immune response which can be generated as a result of delivery of packaged DNA, by whatever means, to a cell or tissue. For example, it is known that DNA vaccines delivered to the skin tend to cause the induction of antibodies, whereas the same vaccine delivered intramuscularly may favour a cellular response. In instances where virus infection is associated with long latency periods, such as is the case, for example, with infection by human immunodeficiency virus and herpes simplex virus, it may be desirable to be able to elicit responses from both arms of the immune system to allow simultaneous protection against future infection and treatment of existing infection.

One example where the unpredictability of the response is of concern is in attempts to overcome the effects of infection by the human papilloma virus (HPV). Many genotypes of HPV are known to be antecedent to ano-genital malignancy[1]; tumours can develop after a latency period of from 10 to 30 years. There is a need, therefore, to find means to induce both neutralising antibody to prevent HPV infection, and cell-mediated immunity to treat existing infection. Induction of a cell-mediated immune response to viral genes is desirable both to control existing infection and, particularly, to eliminate the premalignant consequences of HPV infection. A vaccine, which was capable of effecting both humoral and cellular immunity, would constitute a major advance in medicine's capability to intervene effectively in such disease conditions.

Recent attempts to increase the level of cellular response following DNA immunisation have had some success through conjugation of the sequences encoding the cellular protein ubiquitin. DNA immunisation as a form of gene therapy is a relatively new approach to vaccination. In theory, and sometimes in practice, the inoculated plasmid DNA enters the cell and the encoded proteins are expressed therein. In this way, access of the antigen to the major histocompatibility complex (MHC) class I antigen presentation pathway is more likely to occur. In some cases, enhanced Cytotoxic T Lymphocyte (CTL) responses have been shown following ubiquitination[31,32]. However, ubiquitination is known not to enhance the immunogenicity of all polynucleotide vaccines[35]. Furthermore, the increased CTL response is sometimes at the expense of immunogenicity and production of neutralising antibody[33].

Furthermore, the present inventors have previously shown that the L1 major capsid protein of HPV can self-assemble into virus-like particles (VLPs)[3]. Used as a vaccine, VLPs elicit conformation-dependent host-protective neutralising antibody[4]. However, papilloma virus (PV) infection is often persistent, and 20-50% of HPV-infected individuals do not develop PV-specific immunity[5-7], suggesting that PV infection is seen poorly by the immune system[8]. The capsid genes of HPV have been shown to have sub-optimal codon usage for expression in mammalian cells[12].

SUMMARY OF THE INVENTION

The present invention is predicated in part on a novel strategy for raising a more efficacious immune response against a target antigen. The strategy involves the use of (i) a first antigen corresponding to the target antigen, together with (ii) a second antigen, corresponding to a modified form of the target antigen, whose rate of intracellular proteolytic degradation is increased, enhanced or otherwise elevated relative to the first antigen. As more fully described hereinafter, the present strategy is used advantageously to elicit simultaneously prophylactic and/or therapeutic levels of humoral and cellular responses against an antigen of interest to combat, inter alia, conditions that have latency periods and, therefore, benefit from the dual approach of prophylaxis and therapy.

Thus, in one aspect of the present invention, there is provided a composition for eliciting a humoral and a cellular immune response against a target antigen, comprising a first antigen corresponding to the target antigen, or a polynucleotide from which the first antigen is expressible, together with a second antigen corresponding to a modified form of the target antigen, wherein the rate of intracellular proteolytic degradation of the second antigen is increased, enhanced or otherwise elevated relative to the first antigen, or a polynucleotide from which the second antigen is expressible.

In another aspect, the invention contemplates a composition for eliciting a humoral and a cellular immune response against a target antigen, comprising at least one polynucleotide from which is expressible a first antigen corresponding to the target antigen and a second antigen corresponding to a modified form of the target antigen, wherein the rate of intracellular proteolytic degradation of the second antigen is increased, enhanced or otherwise elevated relative to the first antigen.

In yet another aspect, the invention encompasses a composition for eliciting a humoral and a cellular immune response against a target antigen, comprising a first antigen corresponding to the target antigen and a second antigen corresponding to a modified form of the target antigen, wherein the rate of intracellular proteolytic degradation of the second antigen is increased, enhanced or otherwise elevated relative to the first antigen.

In still yet another aspect, the invention extends to a composition for eliciting a humoral and a cellular immune response against a target antigen, comprising a first antigen corresponding to the target antigen and a polynucleotide from which a second antigen corresponding to a modified form of the target antigen is expressible, wherein the rate of intracellular proteolytic degradation of the second antigen is increased, enhanced or otherwise elevated relative to the first antigen.

In another aspect, the invention envisions a composition for eliciting a humoral and a cellular immune response against a target antigen, comprising a polynucleotide from which a first antigen corresponding to the target antigen is expressible, together with a second antigen corresponding to a modified form of the target antigen, wherein the rate of intracellular proteolytic degradation of the second antigen is increased, enhanced or otherwise elevated relative to the first antigen.

Suitably, the intracellular proteolytic degradation is proteasome-mediated.

Preferably, the intracellular proteolytic degradation is ubiquitin-mediated.

Preferably, the second antigen comprises, or is otherwise associated with, an intracellular degradation signal or degron. In one embodiment, the intracellular degradation signal comprises a destabilising amino acid at the amino-terminus of the second antigen. In a preferred embodiment of this type, the destabilising amino acid is selected from isoleucine and glutamic acid, more preferably from histidine tyrosine and glutamine, and even more preferably from aspartic acid, asparagine, phenylalanine, leucine, tryptophan and lysine. In an especially preferred embodiment, the destabilising amino acid is arginine. In another preferred embodiment of this type, the second antigen is fused or otherwise conjugated to a masking entity, which masks said amino terminus so that when unmasked the second antigen will exhibit the desired rate of intracellular proteolytic degradation. Suitably, the masking entity is a masking protein sequence. The masking protein sequence is preferably cleavable by an endoprotease, which is suitably an endogenous endoprotease of a mammalian cell. For example, an endoprotease cleavage site may be interposed between the masking protein sequence and the second antigen. Suitable endoproteases include, but are not restricted to, serine endoproteases (e.g., subtilisins and furins), proteasomal endopeptidases, proteases relating to the MHC class I processing pathway and signal peptidases. In a preferred embodiment of this type, the masking protein sequence comprises a signal peptide sequence. Suitable signal peptides sequences are described, for example, by Nothwehr et al. (1990, *Bioessays* 12 (10): 479-484), Izard, et al. (1994, *Mol. Microbiol.* 13 (5): 765-773), Menne, et al. (2000, *Bioinformatics.* 16 (8): 741-742) and Ladunga (2000, *Curr. Opin. Biotechnol* 11 (1): 13-18).

Alternatively or in addition, the intracellular degradation signal comprises an ubiquitin acceptor, which allows for the attachment of ubiquitin by intracellular enzymes, which target the second antigen for degradation via the ubiquitin-proteosome pathway. Suitably, the ubiquitin acceptor is a molecule which contains a residue appropriately positioned from the amino terminus of the second antigen as to be able to be bound by ubiquitin molecules. Such residues preferentially have an epsilon amino group such as lysine. In a preferred embodiment of this type, the ubiquitin acceptor comprises at least one, preferably at least two, more preferably at least four and still more preferably at least six lysine residues, which are suitably present in a sufficiently segmentally mobile region of the second antigen.

In another embodiment, the intracellular degradation signal comprises a ubiquitin or biologically active fragment thereof. In a preferred embodiment of this type, the ubiquitin or biologically active fragment thereof is fused, or otherwise conjugated, to the second antigen. Suitably, the ubiquitin is of mammalian origin, more preferably of human or other primate origin. In a preferred embodiment of this type, the ubiquitin comprises the sequence set forth in SEQ ID NO: 2. In an alternate embodiment, the ubiquitin comprises two or more copies the sequence set forth in SEQ ID NO: 2.

The target antigen is suitably refractory or resistant to intracellular proteolytic cleavage, which is preferably associated with a poor or otherwise ineffective cytotoxic T lymphocyte (CTL) response. The target antigen may correspond to at least a portion of a protein to which an immune response is desired. Preferably, the target antigen corresponds to at least a portion of a structural protein. Suitably, the structural protein is a protein of a pathogenic organism (e.g., viral, bacterial, fungal, protozoan). In a preferred embodiment of this type, the structural protein is a viral protein, which is preferably a capsid protein or capsomer. Preferably, the viral capsid protein is a capsid protein of a crystalline virus. Examples of suitable viral capsid proteins include, but are not restricted to, the L1 and/or L2 proteins of papillomavirus, the capsid proteins of a Herpesvirus (e.g., GpD and GpB), VP1-3 of polyomavirus, VP1-6 of blue tongue virus, Hepatitis B surface antigen, Hepatitis C surface antigen, the capsid proteins of Parvovirus, the capsid proteins of Yeast Ty particles, the capsid proteins of Retroviruses (e.g., HIV and RSV), the capsid proteins of Rotavirus, the capsid proteins of Coronaviruses, and the capsid proteins of Adenovirus. In a preferred embodiment, the capsid protein is a papillomavirus (PV) capsid protein. The PV capsid protein is suitably selected from L1 and L2 capsid proteins.

The composition may further comprise an adjuvant. Preferably, the adjuvant delivers the antigens, preferably the second antigen, to the class I major histocompatibility (MHC) pathway. For example, such adjuvants include, but are not limited to, saponin-containing compounds (e.g., ISCOMs) and cytolysins, which mediates delivery of antigens to the cytosol of a target cell. The cytolysin may be linked to, or otherwise associated with, one or both of said antigens. The cytolysin preferably mediates transfer of the antigens from the vacuole (e.g., phagosome or endosome) to the cytosol of the target cell and in a preferred embodiment of this type, the cytolysin is a listeriolysin.

In another aspect, the invention resides in a nucleic acid composition for eliciting a humoral and a cellular immune response against a target antigen, comprising:
 a first polynucleotide encoding a first antigen corresponding to the target antigen; and
 a second polynucleotide encoding a second antigen, corresponding to a modified form of the target antigen, whose rate of intracellular proteolytic degradation is increased, enhanced or otherwise elevated relative to the first antigen;
 wherein said first polynucleotide and said second polynucleotide are operably linked to a regulatory polynucleotide.

In yet another aspect, the invention encompasses a nucleic acid composition for eliciting a humoral and a cellular immune response against a target antigen, comprising:
 a first polynucleotide encoding a first antigen corresponding to the target antigen; and
 a second polynucleotide encoding a second antigen, corresponding to a modified form of the target antigen, whose rate of intracellular proteolytic degradation is increased, enhanced or otherwise elevated relative to the first antigen;
 wherein said first polynucleotide and said second polynucleotide are operably linked to different regulatory polynucleotides.

In a further aspect, the invention contemplates a nucleic acid composition for eliciting a humoral and a cellular immune response against a target antigen, comprising:
 a synthetic construct comprising a first polynucleotide, which encodes a first antigen corresponding to the target antigen, and which is operably linked to a regulatory polynucleotide; and
 another synthetic construct comprising a second polynucleotide encoding a second antigen, which corresponds to a modified form of the target antigen, whose rate of intracellular proteolytic degradation is increased, enhanced or otherwise elevated relative to the first antigen, wherein said second polynucleotide is operably linked to a regulatory polynucleotide.

In one embodiment, the second polynucleotide comprises a first nucleic acid sequence, which encodes an antigen corresponding to the target antigen, and which is linked in reading frame with a second nucleic acid sequence encoding a ubiquitin or biologically active fragment thereof. In a preferred embodiment of this type, the second polynucleotide comprises a first nucleic acid sequence, which encodes an antigen corresponding to the target antigen, and which is linked downstream of, and in reading frame with, a second nucleic acid sequence encoding a ubiquitin or biologically active fragment thereof. In another embodiment of this type, the second polynucleotide comprises a first nucleic acid sequence, which encodes an antigen corresponding to the target antigen, and which is linked upstream of, and in reading frame with, a second nucleic acid sequence encoding a ubiquitin or biologically active fragment thereof. Preferably, but not exclusively, the ubiquitin-encoding nucleic acid sequence comprises the sequence set forth in SEQ ID NO: 1.

In another embodiment, the second polynucleotide comprises a first nucleic acid sequence encoding an antigen, which corresponds to the target antigen, and which is modified to include a destabilising amino acid at its amino-terminus, wherein said first nucleic acid sequence is linked downstream of, and in reading frame with, a second nucleic acid sequence encoding a masking protein sequence.

In one embodiment, the first polynucleotide and/or the second polynucleotide is codon optimised to permit enhanced expression of an antigen encoded thereby in a target cell.

In another embodiment, the first polynucleotide and/or the second polynucleotide is codon optimised to permit higher expression of the antigen encoded thereby in a target cell than in another cell.

The nucleic acid composition may optionally comprise a pharmaceutically acceptable carrier and/or diluent or an adjuvant as broadly described above.

The nucleic acid compositions as broadly described above may be in the form of one or more synthetic constructs.

The invention further contemplates a host cell containing the synthetic construct or synthetic construct system as broadly described above.

In still another aspect, the invention provides a method of eliciting a humoral and a cellular immune response against a target antigen, comprising:
 contacting at least one recipient cell with a composition comprising a first antigen corresponding to the target antigen, and a second antigen, corresponding to a modified form of the target antigen, whose rate of intracellular proteolytic degradation is increased, enhanced or otherwise elevated relative to the first antigen,
 whereby said first antigen and said second antigen are expressed together in the same recipient cell or expressed separately in different recipient cells.

According to another aspect, the invention provides a method of eliciting a humoral and a cellular immune response against a target antigen, comprising:
 contacting at least one recipient cell with a nucleic acid composition as broadly described above, whereby said first antigen and said second antigen are expressed together in the same recipient cell or expressed separately in different recipient cells.

Suitably, the nucleic acid composition is produced by:
 optimising the codon composition of a parent polynucleotide encoding an antigen selected from the group consisting of the first antigen and the second antigen to construct a codon optimised polynucleotide whereby expression of the antigen from the codon optimised polynucleotide in said at least one recipient cell is increased, enhanced or otherwise elevated relative to that from said parent polynucleotide.

In one embodiment, the codon composition is optimised by:
  selecting a first codon of the parent polynucleotide for replacement with a synonymous codon, wherein the first codon is selected on the basis that it has a higher translational efficiency than said synonymous codon in said at least one recipient cell, and
  replacing said first codon with said synonymous codon to construct said codon optimised polynucleotide.

In an alternate embodiment, the codon composition is optimised so that the antigen is expressible at a higher level in said recipient cell than in another cell. In a preferred embodiment of this type, the codon composition is optimised by:
  selecting a first codon of the parent polynucleotide for replacement with a synonymous codon which has a higher translational efficiency in said recipient cell than in said other cell; and
  replacing said first codon with said synonymous codon to form said codon optimised polynucleotide.

The recipient cell(s), which is contacted with the composition, is preferably an antigen-presenting cells, which is suitably selected from a dendritic cell, a macrophage or a B cell.

In yet another aspect, the invention extends to a composition of matter for eliciting a humoral and a cellular immune response against a target antigen, comprising antigen-presenting cells which have been contacted with a first antigen corresponding to the target antigen or with a polynucleotide from which the first antigen is expressible, and with a second antigen corresponding to a modified form of the target antigen, whose rate of intracellular proteolytic degradation is increased, enhanced or otherwise elevated relative to the first antigen or with a polynucleotide from which the second antigen is expressible, for a time and under conditions sufficient to express a processed form of said first antigen, and a processed form of said second antigen, for presentation to, and modulation of, T cells.

Suitably, the composition of matter further includes an adjuvant.

Suitably, the T cells are cytotoxic T lymphocytes (CTLs).

In still yet another aspect, the invention resides in a method of delivering an antigen to antigen-presenting cells for the production of antigen-primed antigen-presenting cells useful for eliciting a humoral and a cellular immune response against a target antigen, said method comprising:
  contacting antigen-presenting cells with a first antigen corresponding to the target antigen or with a polynucleotide from which the first antigen is expressible, and with a second antigen corresponding to a modified form of the target antigen, whose rate of intracellular proteolytic degradation is increased, enhanced or otherwise elevated relative to the first antigen or with a polynucleotide from which the second antigen is expressible, for a time and under conditions sufficient to express a processed form of said first antigen, and a processed form of said second antigen, for a time and under conditions sufficient to permit said antigens to be internalised by the antigen-presenting cells.

The antigen-presenting cells may be contacted in vivo or in vitro and are suitably selected from dendritic cells, macrophages and B cells. Preferably, the antigen-presenting cells are dendritic cells.

In a further aspect of the invention, there is provided a method for producing antigen-primed antigen-presenting cells for eliciting a humoral and a cellular immune response against a target antigen, comprising:
  contacting antigen-presenting cells with a first antigen corresponding to the target antigen or with a polynucleotide from which the first antigen is expressible, and with a second antigen corresponding to a modified form of the target antigen, whose rate of intracellular proteolytic degradation is increased, enhanced or otherwise elevated relative to the first antigen or with a polynucleotide from which the second antigen is expressible, for a time and under conditions sufficient to express a processed form of said first antigen, and a processed form of said second antigen, for a time and under conditions sufficient to permit said antigens to be internalised by the antigen-presenting cells; and
  culturing the antigen-presenting cells for a time and under conditions sufficient for said first and said second antigens to be processed for presentation by the antigen-presenting cells.

Suitably, the above method further comprises isolating antigen-presenting cells from a heterogeneous population of cells.

In a further aspect of the invention, there is provided a method for modulating an immune response, comprising administering to a patient in need of such treatment a composition as broadly described above.

According to a still further aspect of the invention, there is provided a method for treatment and/or prophylaxis of a disease or condition, comprising administering to a patient in need of such treatment an effective amount of a composition as broadly described above.

A further aspect of the present invention is directed to a method for eliciting a humoral and a cellular immune response against a target antigen, comprising coadministering to a patient:
  a first antigen corresponding to the target antigen, or a polynucleotide from which the first antigen is expressible; and
  a second antigen corresponding to a modified form of the target antigen, wherein the rate of intracellular proteolytic degradation of the second antigen is increased, enhanced or otherwise elevated relative to the first antigen, or a polynucleotide from which the second antigen is expressible.

In yet another aspect, the invention contemplates a method for eliciting a humoral and a cellular immune response against a target antigen, comprising coadministering to a patient:
  a polynucleotide from which a first antigen, corresponding to the target antigen, is expressible; and
  a polynucleotide from which a second antigen, corresponding to a modified form of the target antigen, is expressible, wherein the rate of intracellular proteolytic degradation of the second antigen is increased, enhanced or otherwise elevated relative to the first antigen.

In still yet another aspect, the invention encompasses a method for eliciting a humoral and a cellular immune response against a target antigen, comprising coadministering to a patient:
  a first antigen corresponding to the target antigen; and
  a polynucleotide from which a second antigen, corresponding to a modified form of the target antigen, is expressible, wherein the rate of intracellular proteolytic degradation of the second antigen is increased, enhanced or otherwise elevated relative to the first antigen.

In a further aspect, the invention resides in a method for eliciting a humoral and a cellular immune response against a target antigen, comprising coadministering to a patient:
  a polynucleotide from which a first antigen, corresponding to the target antigen, is expressible; and
  a second antigen corresponding to a modified form of the target antigen, wherein the rate of intracellular proteolytic degradation of the second antigen is increased, enhanced or otherwise elevated relative to the first antigen.

In still a further aspect, the invention provides a method for eliciting a humoral and a cellular immune response against a target antigen, comprising coadministering to a patient:
  antigen-presenting cells which have been contacted with a first antigen corresponding to the target antigen, or with a polynucleotide from which the first antigen is expressible, for a time and under conditions sufficient to express a processed form of said first antigen for presentation to, and modulation of, T cells; and
  antigen-presenting cells which have been contacted with a second antigen, corresponding to a modified form of the target antigen, whose rate of intracellular proteolytic degradation is increased, enhanced or otherwise elevated relative to the first antigen, or with a polynucleotide from which the second antigen is expressible, for a time and under conditions sufficient to express a processed form of said second antigen for presentation to, and modulation of, T cells,
  wherein the antigen-presenting cells which have been contacted with the first antigen and the antigen-presenting cells which have been contacted with the second antigen may be the same or different.

In still another aspect, the invention provides a method for eliciting a humoral and a cellular immune response against a target antigen, comprising coadministering to a patient:
  antigen-presenting cells which have been contacted with a first antigen corresponding to the target antigen, or with a polynucleotide from which the first antigen is expressible, together with a second antigen, corresponding to a modified form of the target antigen, whose rate of intracellular proteolytic degradation is increased, enhanced or otherwise elevated relative to the first antigen, or with a polynucleotide from which the second antigen is expressible, for a time and under conditions sufficient to express a processed form of said first antigen and a processed form of said second antigen for presentation to, and modulation of, T cells.

In a further aspect, the invention extends to the use of a first antigen or a polynucleotide from which the first antigen is expressible, together with a second antigen or a polynucleotide from which the second antigen is expressible, in the preparation of a medicament for the treatment of a disease or condition associated with a target antigen, said first antigen corresponding to the target antigen and said second antigen corresponding to a modified form of the target antigen, wherein the rate of intracellular proteolytic degradation of the second antigen is increased, enhanced or otherwise elevated relative to the first antigen.

In yet another aspect, the invention extends to the use of a first antigen or a polynucleotide from which the first antigen is expressible, together with antigen-presenting cells, in the preparation of a medicament for the treatment of a disease or condition associated with a target antigen, wherein said first antigen corresponds to the target antigen and wherein said antigen-presenting cells have been exposed to a second antigen, corresponding to a modified form of the target antigen, whose rate of intracellular proteolytic degradation is increased, enhanced or otherwise elevated relative to the first antigen, for a time and under conditions sufficient to express a processed form of said second antigen for presentation to, and modulation of, T cells.

In still yet another aspect, the invention contemplates the use of a antigen-presenting cells in the preparation of a medicament for the treatment of a disease or condition associated with a target antigen, wherein said antigen-presenting cells have been exposed to a first antigen corresponding to the target antigen, or to a polynucleotide from which the first antigen is expressible, together with a second antigen, corresponding to a modified form of the target antigen, whose rate of intracellular proteolytic degradation is increased, enhanced or otherwise elevated relative to the first antigen, or to a polynucleotide from which the second antigen is expressible, for a time and under conditions sufficient to express a processed form of said first antigen and a processed form of said second antigen for presentation to, and modulation of, T cells.

The invention also encompasses the use of the synthetic polypeptide, the synthetic polynucleotide and the synthetic construct as broadly described above in the study, and modulation of immune responses.

Figure 1:
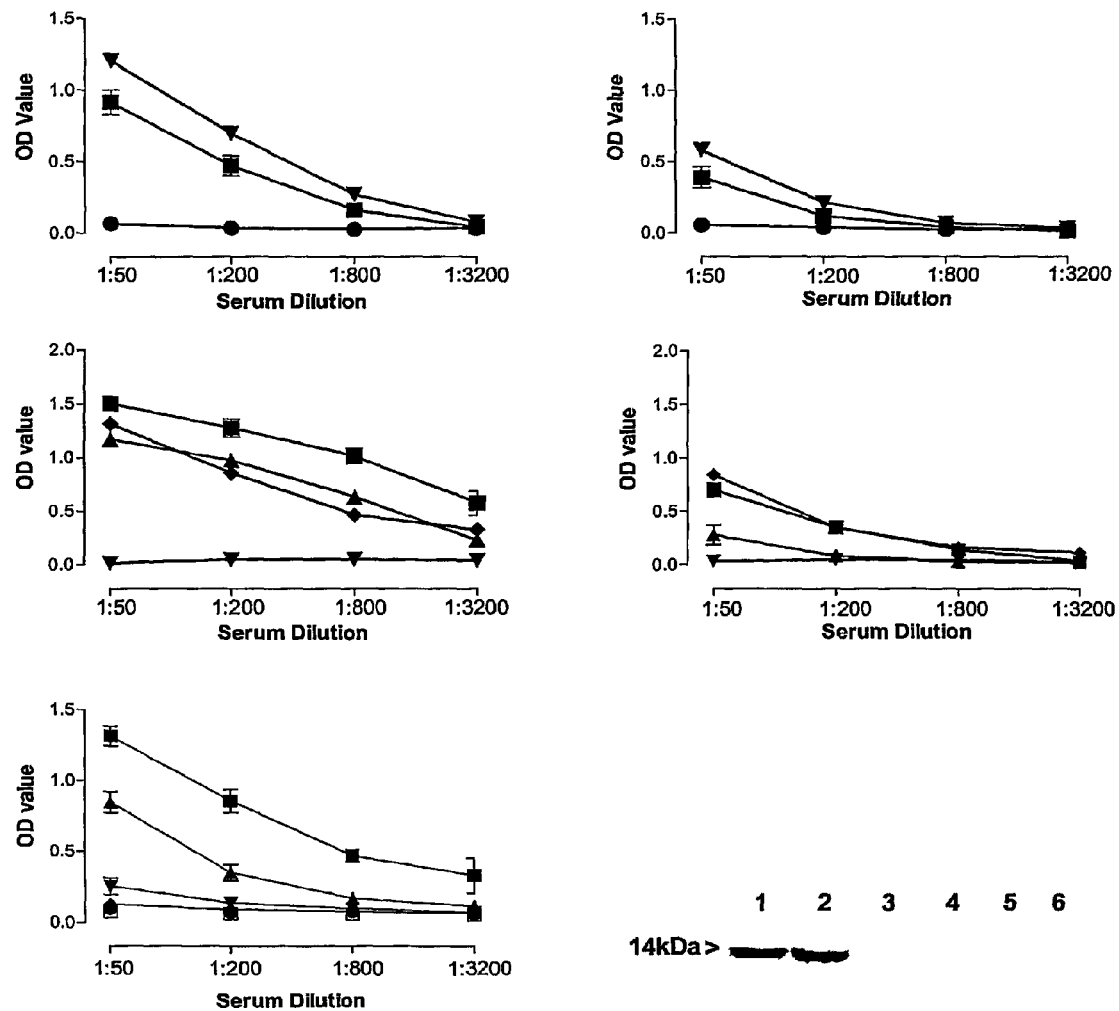
FIG. 1 is a graphical representation showing immunogenicity of codon-modified and unmodified HPV 6L1. Graphs a and b show reactivity of sera from mice immunised with (■)codon-modified L1 pH6L1Δ, single immunisation, or (▼)codon-modified L1 (pH6L1Δ), double immunisation, or (●)codon-unmodified L1(p6L1Δ), double immunisation with (a) HPV6bL1 VLPs (conformational antibody) or (b) denatured HPV6b L1 (linear antibody); Graphs c and d show reactivity of sera from mice immunised with (■)codon-modified HPV6b L1E7.1, (▲) codon modified HPV6b L1-E7.2, (♦)codon-modified HPV6b L1-HPV16E7 or (▼) native sequence HPV6b L1 with (c) HPV6b L1 VLPs (conformational antibody), or (d) denatured HPV6b L1 (linear antibody). All results are means ±1 S.E.M from groups of 5 mice. Graph e shows reactivity of sera from mice immunised with p6HL116E7(■ ▲), ubiquitin-conjugated pU6HL116E7(▼ ♦) or pCDNA3 (● □) against native VLPs (■ ▼ ●) or denatured L1 (▲ ♦ □). Graph f shows serum reactivity to recombinant HPV6b E7 from mice immunised with (lane 1,4) pH6L1E7.1, (lane 2,5) pH6L1E7.2, or (lane 3,6) p6L1A. Lane 1-3: lysate from Cos-1 cells transfected with pCDNAE7. Lane 4-6: Cos-1 cell lysate.

BRIEF DESCRIPTION OF THE SEQUENCES:
SUMMARY TABLE

TABLE A

| SEQUENCE ID | DESCRIPTION | LENGTH |
| --- | --- | --- |
| SEQ ID NO: 1 | Human ubiquitin coding sequence (CDS), 1 copy | 231 nts |
| SEQ ID NO: 2 | Polypeptide encoded by SEQ ID NO: 1 | 76 aa |
| SEQ ID NO: 3 | HPV type 6b wild-type L1 protein (L1) CDS as set forth in GenBank Accession No. NC_001355 | 1503 nts |
| SEQ ID NO: 4 | Polypeptide encoded by SEQ ID NO: 3 | 500 aa |
| SEQ ID NO: 5 | Synthetic construct HPV type 6b humanised L1 protein (L1) CDS as set forth in GenBank Accession No. AF322411 | 1503 nts |
| SEQ ID NO: 6 | Polypeptide encoded by SEQ ID NO: 5 | 500 aa |
| SEQ ID NO: 7 | Synthetic construct HPV type 6b wild-type truncated L1 protein (L1) CDS | 1404 nts |
| SEQ ID NO: 8 | Polypeptide encoded by SEQ ID NO: 7 | 467 aa |
| SEQ ID NO: 9 | Synthetic construct HPV type 6b humanised truncated L1 protein (L1) CDS as set forth in GenBank Accession No. AF322412 | 1404 nts |
| SEQ ID NO: 10 | Polypeptide encoded by SEQ ID NO: 9 | 467 aa |
| SEQ ID NO: 11 | Synthetic construct HPV type 6b humanised L1/E7.1 hybrid protein CDS as set forth in GenBank Accession No. AF322413 | 1554 nts |
| SEQ ID NO: 12 | Polypeptide encoded by SEQ ID NO: 11 | 517 aa |
| SEQ ID NO: 13 | Synthetic construct HPV type 6b humanised L1/E7.2 hybrid protein CDS as set forth in GenBank Accession No. AF322414 | 1554 nts |
| SEQ ID NO: 14 | Polypeptide encoded by SEQ ID NO: 13 | 517 aa |
| SEQ ID NO: 15 | Synthetic construct HPV type 6b humanised L1/ubiquitin hybrid protein CDS as set forth in GenBank Accession No. AF322415 | 1728 nts |
| SEQ ID NO: 16 | Polypeptide encoded by SEQ ID NO: 15 | 575 aa |
| SEQ ID NO: 17 | Synthetic construct HPV type 6b humanised ubiquitin/L1 delta/H-2 Db CTL epitope hybrid protein CDS as set forth in GenBank Accession No. AF323508 | 1677 nts |
| SEQ ID NO: 18 | Polypeptide encoded by SEQ ID NO: 17 | 558 aa |
| SEQ ID NO: 19 | Synthetic construct HPV type 6b humanised L1 delta/H-2 Db CTL CTL epitope hybrid protein CDS as set forth in GenBank Accession No. AF323509 | 1452 nts |
| SEQ ID NO: 20 | Polypeptide encoded by SEQ ID NO: 19 | 483 aa |
| SEQ ID NO: 21 | BPV type 1 wild-type L2 protein (L2) CDS as set forth in GenBank Accession No. X01768 | 1404 nts |
| SEQ ID NO: 22 | Polypeptide encoded by SEQ ID NO: 21 | 467 aa |
| SEQ ID NO: 23 | Synthetic construct BPV type 1 humanised L2 protein (L2) CDS | 1410 nts |
| SEQ ID NO: 24 | Polypeptide encoded by SEQ ID NO: 23 | 469 aa |

DETAILED DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

The term "about" is used herein to refer to conditions (e.g., amounts, concentrations, time etc.) that vary by as much as 30%, preferably by as much as 20%, and more preferably by as much as 10% to a specified condition.

The terms "administration concurrently" or "administering concurrently" or "coadministering" and the like refer to the administration of a single composition containing two or more actives, or the administration of each active as separate compositions and/or delivered by separate routes either simultaneously or sequentially within a short enough period of time that the effective result is equivalent to that obtained when all such actives are administered as a single composition.

By "antigen-binding molecule" is meant a molecule that has binding affinity for a target antigen. It will be understood that this term extends to immunoglobulins, immunoglobulin fragments and non-immunoglobulin derived protein frameworks that exhibit antigen-binding activity.

By "autologous" is meant something (e.g., cells, tissues etc.) derived from the same organism.

The term "allogeneic" as used herein refers to cells, tissues, organisms etc. that are of different genetic constitution although derived from the same species.

By "biologically active fragment" is meant a fragment of a full-length parent polypeptide which fragment retains the activity of the parent polypeptide. For example, a biologically active fragment of ubiquitin when conjugated to an antigen of interest will increase, enhance or otherwise elevate the rate of intracellular proteolytic degradation of that antigen. As used herein, the term "biologically active fragment" includes deletion mutants and small peptides, for example of at least 8, preferably at least 10, more preferably at least 15, even more preferably at least 20 and even more preferably at least 30 contiguous amino acids, which comprise the above activity. Peptides of this type may be obtained through the application of standard recombinant nucleic acid techniques or synthesised using conventional liquid or solid phase synthesis techniques. For example, reference may be made to solution synthesis or solid phase synthesis as described, for example, in Chapter 9 entitled "*Peptide Synthesis*" by Atherton and Shephard which is included in a publication entitled "*Synthetic Vaccines*" edited by Nicholson and published by Blackwell Scientific Publications. Alternatively, peptides can be produced by digestion of a polypeptide of the invention with proteinases such as endoLys-C, endoArg-C, endoGlu-C and staphylococcus V8-protease. The digested fragments can be purified by, for example, high performance liquid chromatographic (HPLC) techniques.

As used herein, the term "cis-acting sequence" or "cis-regulatory region" or similar term shall be taken to mean any sequence of nucleotides which is derived from an expressible genetic sequence wherein the expression of the genetic sequence is regulated, at least in part, by said sequence of nucleotides. Those skilled in the art will be aware that a cis-regulatory region may be capable of activating, silencing, enhancing, repressing or otherwise altering the level of expression and/or cell-type-specificity and/or developmental specificity of any structural gene sequence.

Throughout this specification, unless the context requires otherwise, the words "comprise", "comprises" and "comprising" will be understood to imply the inclusion of a stated step or element or group of steps or elements but not the exclusion of any other step or element or group of steps or elements.

By "corresponds to" or "corresponding to" is meant a polynucleotide (a) having a nucleotide sequence that is substantially identical or complementary to all or a portion of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein.

By "derivative" is meant a polypeptide that has been derived from the basic sequence by modification, for example by conjugation or complexing with other chemical moieties or by post-translational modification techniques as would be understood in the art. The term "derivative" also includes within its scope alterations that have been made to a parent sequence including additions, or deletions that provide for functionally equivalent molecules.

By "effective amount", in the context of treating, preventing or ameliorating the symptoms of a condition, is meant the administration of that amount of immunopotentiating composition or active compound that elicits an immune response in an individual in need of such treatment, prevention or amelioration, either in a single dose or as part of a series, that is effective for treatment of that condition. The effective amount will vary depending upon the health and physical condition of the individual to be treated, the taxonomic group of individual to be treated, the formulation of the composition, the assessment of the medical situation, and other relevant factors. It is expected that the amount will fall in a relatively broad range that can be determined through routine trials.

By "expressing", and like terms such as "expression" and "expressible", in the context or protein expression, is meant expression of a protein to a level sufficient to effect a particular function associated with the protein.

By "expressing said polynucleotide" is meant transcribing the polynucleotide such that mRNA is produced.

By "expression vector" is meant any autonomous genetic element capable of directing the synthesis of a protein encoded by the vector. Such expression vectors are known by practitioners in the art.

The term "gene" is used in its broadest context to include both a genomic DNA region corresponding to the gene as well as a cDNA sequence corresponding to exons or a recombinant molecule engineered to encode a functional form of a product.

"Homology" refers to the percentage number of amino acids that are identical or constitute conservative substitutions as defined in Table B infra. Homology may be determined using sequence comparison programs such as GAP (Deveraux et al. 1984). In this way, sequences of a similar or substantially different length to those cited herein might be compared by insertion of gaps into the alignment, such gaps being determined, for example, by the comparison algorithm used by GAP.

To enhance immune response ("immunoenhancement"), as is well-known in the art, means to increase the animal's capacity to respond to foreign or disease-specific antigens (e.g., viral antigens, cancer antigens) i.e., those cells primed to attack such antigens are increased in number, activity, and ability to detect and destroy those antigens. Strength of immune response is measured by standard tests including: direct measurement of peripheral blood lymphocytes by means known to the art; natural killer cell cytotoxicity assays (see, e.g., Provinciali et al. (1992, *J. Immunol. Meth.* 155: 19-24), cell proliferation assays (see, e.g., Vollenweider and Groseurth (1992, *J. Immunol. Meth.* 149: 133-135), immunoassays of immune cells and subsets (see, e.g., Loeffler et al. (1992, *Cytom.* 13: 169-174); Rivoltini et al. (1992, *Can. Immunol. Immunother.* 34: 241-251); or skin tests for cell-mediated immunity (see, e.g., Chang et al. (1993, *Cancer Res.* 53: 1043-1050). Any statistically significant increase in strength of immune response as measured by the foregoing tests is considered "enhanced immune response" "immunoenhancement" or "immunopotentiation" as used herein. Enhanced immune response is also indicated by physical manifestations such as fever and inflammation, as well as healing of systemic and local infections, and reduction of symptoms in disease, i.e., decrease in tumour size, alleviation of symptoms of a disease or condition including, but not restricted to, leprosy, tuberculosis, malaria, naphthous ulcers, herpetic and papillomatous warts, gingivitis, artherosclerosis, the concomitants of AIDS such as Kaposi's sarcoma, bronchial infections, and the like. Such physical manifestations also define "enhanced immune response" "immunoenhancement" or "immunopotentiation" as used herein.

Reference herein to "immuno-interactive" includes reference to any interaction, reaction, or other form of association between molecules and in particular where one of the molecules is, or mimics, a component of the immune system.

By "isolated" is meant material that is substantially or essentially free from components that normally accompany it in its native state.

By "modulating" is meant increasing or decreasing, either directly or indirectly, the level and/or functional activity of a target molecule. For example, an agent may indirectly modulate the said level/activity by interacting with a molecule other than the target molecule. In this regard, indirect modulation of a gene encoding a target polypeptide includes within its scope modulation of the expression of a first nucleic acid molecule, wherein an expression product of the first nucleic acid molecule modulates the expression of a nucleic acid molecule encoding the target polypeptide.

The term "5' non-coding region" is used herein in its broadest context to include all nucleotide sequences which are derived from the upstream region of an expressible gene, other than those sequences which encode amino acid residues which comprise the polypeptide product of said gene, wherein 5' non-coding region confers or activates or otherwise facilitates, at least in part, expression of the gene.

The term "oligonucleotide" as used herein refers to a polymer composed of a multiplicity of nucleotide units (deoxyribonucleotides or ribonucleotides, or related structural variants or synthetic analogues thereof) linked via phosphodiester bonds (or related structural variants or synthetic analogues thereof). Thus, while the term "oligonucleotide" typically refers to a nucleotide polymer in which the nucleotides and linkages between them are naturally occurring, it will be understood that the term also includes within its scope various analogues including, but not restricted to, peptide nucleic acids (PNAs), phosphoramidates, phosphorothioates, methyl phosphonates, 2-O-methyl ribonucleic acids, and the like. The exact size of the molecule may vary depending on the particular application. An oligonucleotide is typically rather short in length, generally from about 10 to 30 nucleotides, but the term can refer to molecules of any length, although the term "polynucleotide" or "nucleic acid" is typically used for large oligonucleotides.

The term "operably connected" or "operably linked" as used herein means placing a structural gene under the regulatory control of a promoter, which then controls the transcription and optionally translation of the gene. In the construction of heterologous promoter/structural gene combinations, it is generally preferred to position the genetic sequence or promoter at a distance from the gene transcription start site that is approximately the same as the distance between that genetic sequence or promoter and the gene it controls in its natural setting; i.e. the gene from which the genetic sequence or promoter is derived. As is known in the art, some variation in this distance can be accommodated without loss of function. Similarly, the preferred positioning of a regulatory sequence element with respect to a heterologous gene to be placed under its control is defined by the positioning of the element in its natural setting; i.e. the genes from which it is derived.

The term "patient" refers to patients of human or other mammal and includes any individual it is desired to examine or treat using the methods of the invention. However, it will be understood that "patient" does not imply that symptoms are present. Suitable mammals that fall within the scope of the invention include, but are not restricted to, primates, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes).

By "pharmaceutically-acceptable carrier" is meant a solid or liquid filler, diluent or encapsulating substance that may be safely used in topical or systemic administration.

The term "polynucleotide" or "nucleic acid" as used herein designates mRNA, RNA, cRNA, cDNA or DNA. The term typically refers to oligonucleotides greater than 30 nucleotides in length.

"Polypeptide", "peptide" and "protein" are used interchangeably herein to refer to a polymer of amino acid residues and to variants and synthetic analogues of the same. Thus, these terms apply to amino acid polymers in which one or more amino acid residues is a synthetic non-naturally occurring amino acid, such as a chemical analogue of a corresponding naturally occurring amino acid, as well as to naturally-occurring amino acid polymers.

By "primer" is meant an oligonucleotide which, when paired with a strand of DNA, is capable of initiating the synthesis of a primer extension product in the presence of a suitable polymerising agent. The primer is preferably single-stranded for maximum efficiency in amplification but may alternatively be double-stranded. A primer must be sufficiently long to prime the synthesis of extension products in the presence of the polymerisation agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotides, although it may contain fewer nucleotides. Primers can be large polynucleotides, such as from about 200 nucleotides to several kilobases or more. Primers may be selected to be "substantially complementary" to the sequence on the template to which it is designed to hybridise and serve as a site for the initiation of synthesis. By "substantially complementary", it is meant that the primer is sufficiently complementary to hybridise with a target nucleotide sequence. Preferably, the primer contains no mismatches with the template to which it is designed to hybridise but this is not essential. For example, non-complementary nucleotides may be attached to the 5' end of the primer, with the remainder of the primer sequence being complementary to the template. Alternatively, non-complementary nucleotides or a stretch of non-complementary nucleotides can be interspersed into a primer, provided that the primer sequence has sufficient complementarity with the sequence of the template to hybridise therewith and thereby form a template for synthesis of the extension product of the primer.

"Probe" refers to a molecule that binds to a specific sequence or sub-sequence or other moiety of another molecule. Unless otherwise indicated, the term "probe" typically refers to a polynucleotide probe that binds to another nucleic acid, often called the "target nucleic acid", through complementary base pairing. Probes may bind target nucleic acids lacking complete sequence complementarity with the probe, depending on the stringency of the hybridisation conditions. Probes can be labelled directly or indirectly.

Reference herein to a "promoter" is to be taken in its broadest context and includes the transcriptional regulatory sequences of a classical genomic gene, including the TATA box which is required for accurate transcription initiation, with or without a CCAAT box sequence and additional regulatory elements (i.e. upstream activating sequences, enhancers and silencers) which alter gene expression in response to developmental and/or environmental stimuli, or in a tissue-specific or cell-type-specific manner. A promoter is usually, but not necessarily, positioned upstream or 5', of a structural gene, the expression of which it regulates. Furthermore, the regulatory elements comprising a promoter are usually positioned within 2 kb of the start site of transcription of the gene. Preferred promoters according to the invention may contain additional copies of one or more specific regulatory elements to further enhance expression in a cell, and/or to alter the timing of expression of a structural gene to which it is operably connected.

The term "recombinantpolynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably linked to the nucleotide sequence.

By "recombinant polypeptide" is meant a polypeptide made using recombinant techniques, i.e., through the expression of a recombinant polynucleotide.

The term "synonymous codon" as used herein refers to a codon having a different nucleotide sequence than another codon but encoding the same amino acid as that other codon.

By "translational efficiency", is meant the efficiency of a cell's protein synthesis machinery to incorporate the amino acid encoded by a codon into a nascent polypeptide chain. This efficiency can be evidenced, for example, by the rate at which the cell is able to synthesise the polypeptide from an RNA template comprising the codon, or by the amount of the polypeptide synthesised from such a template.

By "vector" is meant a nucleic acid molecule, preferably a DNA molecule derived, for example, from a plasmid, bacteriophage, or plant virus, into which a nucleic acid sequence may be inserted or cloned. A vector preferably contains one or more unique restriction sites and may be capable of autonomous replication in a defined host cell including a target cell or tissue or a progenitor cell or tissue thereof, or be integrable with the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. The vector may also include a selection marker such as an antibiotic resistance gene that can be used for selection of suitable transformants. Examples of such resistance genes are well known to those of skill in the art.

2. Abbreviations

BPV: Bovine papillomavirus
CRPV: Cottontail rabbit papillomavirus
DTH: Delayed Type Hypersensitivity
HAI: hemagglutination inhibition assay
HPV: Human papillomavirus
PV: papillomavirus
VLP: virus like particle 3. Production of Antigens of the Invention In work leading up to the present invention, the inventors sought to develop immunogenic agents, particularly polynucleotides, which would combine the desired effects of enhanced immunogenicity, as well as predictable/controlled ability to elicit host-protective antibody, whilst not precluding or diminishing the induction of a cell-mediated response to facilitate treatment of existing infection. It was observed that in cases where antibody was favoured, the approach used reduced the induction of a cell-mediated response. Similarly, in cases where the latter effect was favoured, the approach used reduced the former desired effect. In seeking to overcome one of the difficulties without removing the second desired benefit, the inventors inadvertently discovered that by tackling simultaneously the problems of impaired immunogenicity and controlled immunological responses, a combined approach could overcome both hurdles.

Accordingly, the present invention is predicated in part on a novel strategy for eliciting simultaneously a host-protective antibody response and a cell-mediated immune response against a target antigen to combat, inter alia, conditions that have latency periods and, therefore, benefit from the dual approach of prophylaxis and therapy. The strategy involves administering to an individual a first antigen corresponding to the target antigen, and being suitably intracellularly resistant to proteolysis. In addition, a second antigen, corresponding to a modified form of the target antigen, is administered to the individual, wherein the rate of intracellular proteolytic degradation of the second antigen is increased, enhanced or otherwise elevated relative to the first antigen. The first and second antigens may be administered in proteinaceous form, or in nucleic acid form, or a combination thereof. The antigenic determinant(s) or epitope(s) of the first antigen and the second antigen may be the same or different. Accordingly, the epitope-containing sequence of the first antigen and the second antigen may be the same or different. Preferably, the first antigen and the second antigen comprise the same epitope(s). Suitably, when corresponding epitopes are different between the first antigen and the second antigen, such epitopes are preferably capable of eliciting the production of elements that bind to a corresponding epitope of the target antigen.

Exemplary target antigens include, but are not limited to, at least a portion of a structural protein including, but not restricted to, structural proteins of pathogenic organisms (e.g., viral, bacterial, fungal, protozoan) such as capsid proteins or capsomers. In a preferred embodiment, the capsid protein is of viral origin. Preferably, the viral capsid protein relates to a crystalline virus. Examples of suitable viral capsid proteins include, but are not restricted to, the L1 and/or L2 proteins of papillomavirus, the capsid proteins of a Herpesvirus (e.g., GpD and GpB), VP1-3 of polyomavirus, VP1-6 of blue tongue virus, Hepatitis B surface antigen, Hepatitis C surface antigen, the capsid proteins of Parvovirus, the capsid proteins of Yeast Ty particles, the capsid proteins of Retroviruses (e.g., HIV and RSV), the capsid proteins of Rotavirus, the capsid proteins of Coronaviruses, and the capsid proteins of Adenovirus. Alternatively, the target antigen is a structural protein relating to the crystalline core of a lipid enveloped virus. For a more comprehensive list of viral structural proteins, see Fields Virology (editors-in-chief, Bernard N. Fields, David M. Knipe, Peter M. Howley, 4$^{th}$ edition, Lippincott-Raven Publishers, 1999, Philadelphia, USA).

Alternatively, suitable viral capsid proteins include those that can be used to produce virus-like particles including, but not restricted to, Ty-virus-like particles as for example described by Oliveira-Ferreira et. al. (2000 *Vaccine*, 18 (17): 1863-1869), Hirschberg et al. (1999, *Int Immunol*, 11 (12): 1927-1934), Klein et al. (1997, *AIDS Res Hum Retroviruses*, 13(5): 393-399), Allsopp et al. (1996, *Eur J Immunol*, 26 (8): 1951-195), Bachmann et al. (1996, supra), Layton et al. (1996, *Immunology*, 87 (2): 171-178; 1993, *J Immunol*, 151 (2): 1097-1107), Brookman et al. (1995, *Virology*, 207 (1): 59-67), Burns et al. (1994, *Mol Biotechnol*, 1 (2): 137-145), Martin et al. (1993, *AIDS*, 7(10): 1315-1323) and Adams et al. (1987, *Nature*, 329 (6134): 68-70), human immuno deficiency virus-like particles as for example described by Paliard et al. (2000, *AIDS Res Hum Retroviruses*, 16 (3): 273-282), Notka et al. (1999, *Biol Chem*, 380 (3): 341-352) and Wagner et al. (1998, *Virology*, 245 (1): 65-74; 1994, *Behring Inst Mitt*, (95): 23-34), Norwalk virus-like particles as for example described by Ball et al. (1999, *Gastroenterology*, 111 (1): 40-48) and White et al. (1996, *J Virol*, 70 (10): 6589-6597), p24-VLP as for example described by Benson et al. (1999, *AIDS Res Hum Retroviruses*, 15 (2): 105-113), papilloma virus-like particles as for example described by Zhou et al. (1991, *Virology*, 181: 203-210; ibid 185: 251-257), and International publication WO 93/02184), Christensen et al. (2000, *Virology*, 269 (2): 451-461), and Benyacoub et al., (1999, *Infect Immun*, 67 (7): 3674-3679), Hepatitis virus-like particles as for example described by Falcon et al. (1999, *Tissue Cell*, 31 (2): 117-125), Li et al. (1997, *J Virol*, 71 (10): 7207-7213) and Schirmbeck et al. (1996, *Intervirology*, 39 (1-2): 111-119), polyomavirus virus-like particles as for example described by Goldmann et al. (1999, *J Virol*, 73 (5): 4465-4469) and Szomolanyi-Tsuda et al., (1998, *J Virol*, 72 (8): 6665-6670), adeno-associated virus-like particles as for example described by Hoque et al. (1999, *Biochem Biophys Res Commun*, 266 (2): 371-376), infectious bursal disease virus-like particles as for example described by Hu et al. (1999 *Biotechnol Bioeng*, 63 (6): 721-729), Kibenge et al. (1999, *Can J Vet Res*, 63 (1): 49-55) and Fernandez-Arias et al. (1998, *J Gen Virol*, 79 (Pt 5): 1047-1054), rotavirus-like particles as for example described by Jiang et al. (1999, *Vaccine*, 17 (7-8): 1005-1013), Ciarlet et al. (1998, *J Virol*, 72 (11): 9233-9246), Gilbert et al. (1997, *J Virol*, 71 (6): 4555-4563) and Conner et al. (1996, *J Infect Dis*, 174 Suppl 1:S88-S92), calicivirus-like particles as for example described by Jiang et al. (1999, *J Virol Methods*, 78 (1-2): 81-91), bovine leukemia virus-like particles as for example described by Kakker et al. (1999, *Virology*, 265 (2): 308-318), rabbit haemorrhagic disease virus-like particles as for example described by Nagesha et al. (1999, *Arch Virol*, 144 (12): 2429-2439), parvovirus-like particles as for example described by Sedlik et al. (1999, *J Virol*, 73 (4): 2739-2744), Lo-Man et al. (1998, *Eur J Immunol*, 28 (4): 1401-1407) and Sedlik et al (1997, *Proc Natl Acad Sci USA*, 94 (14): 7503-7508, transposable element D-based virus like particles as for example described by Hajek et al. (1998, *J Virol*, 72 (11): 8718-8724), mouse coronavirus-like particles as for example described by Bos et al. (1997, *J Virol*, 71 (12): 9427-9433; 1996, *Virology*, 218 (1): 52-60), potato leafroll luteovirus-like particles as for example described by Lamb et al. (1996, *J Gen Virol*, 11 (Pt 7): 1349-1358), bluetongue virus-like particles as for example described by Murray and Eaton. (1996, *Vaccines for. Aust Vet J*, 73 (6): 207-210), protozoan virus-like particles as for example described by Sitja-Bobadilla et al. (1996, *Int J Parasitol*, 26 (4): 457-459), and Epstein-Barr virus-like particles as for example described by Yano et al. (1986, *Int J Cancer*, 38 (2): 275-284). In a preferred embodiment, the capsid protein is a papillomavirus capsid protein. The capsid protein is suitably selected from L1 and L2 capsid proteins.

3.1 Production of Modified Antigen

A second or modified antigen according to the present invention may be prepared using any suitable technique that renders it less resistant to proteolysis intracellularly relative to a first antigen corresponding to the target antigen of interest. However, it should be noted that the present invention is not dependent on, and not directed to, any one particular technique by which the second or modified antigen is produced. The intracellular half life of a first or target antigen is suitably greater than about 3 minutes, preferably greater than about 5 minutes, more preferably greater than about 10 minutes, even more preferably greater than about 15 minutes, even more preferably greater than about 30 minutes, even more preferably greater than about 1 hour, even more preferably greater than about 10 hours, even more preferably greater than about 24 hours, and still even more preferably greater than about 50 hours. Suitably, a proteolytically resistant antigen is one that retains greater than about 10% of its tertiary structure after about 3 minutes, preferably after about 5 minutes, more preferably after about 10 minutes, even more preferably after about 15 minutes, even more preferably after about 30 minutes, even more preferably after about 1 hour, even more preferably after about 10 hours, even more preferably after about 24 hours, and still even more preferably after about 50 hours at intracellular or intracellular-like conditions. Preferably, a proteolytically resistant antigen is one that retains greater than about 20% of its tertiary structure after about 3 minutes, preferably after about 5 minutes, more preferably after about 10 minutes, even more preferably after about 15 minutes, even more preferably after about 30 minutes, even more preferably after about 1 hour, even more preferably after about 10 hours, even more preferably after about 24 hours, and still even more preferably after about 50 hours at intracellular or intracellular-like conditions. More preferably, a proteolytically resistant antigen is one that retains greater than about 50% of its tertiary structure after about 3 minutes, preferably after about 5 minutes, more preferably after about 10 minutes, even more preferably after about 15 minutes, even more preferably after about 30 minutes, even more preferably after about 1 hour, even more preferably after about 10 hours, even more preferably after about 24 hours, and still even more preferably after about 50 hours at intracellular or intracellular-like conditions. The intracellular or intracellular-like conditions are preferably physiological for the cell type. The cell type is preferably an antigen presenting cell, more preferably a professional antigen presenting cell including, but not restricted to, a dendritic cell, a macrophage and a B cell. The temperature of the intracellular or intracellular-like conditions is preferably physiological for the cell type. Exemplary temperatures for mammalian cells range suitably from about 30° C. to about 42° C., and preferably from about 35° C. to about 37° C. The intracellular half life of the second antigen is suitably less than about 50 hours, preferably less than about 10 hours, more preferably less than about 1 hour, even more preferably less than about 30 minutes, even more preferably less than about 15 minutes, even more preferably less than about 10 minutes and still even more preferably less than about 3 minutes. At a minimum, enhanced proteolytic degradation of the second antigen refers to a level of proteolytic degradation that is at least about 5%, preferably at least about 10%, more preferably at least about 20%, even more preferably at least about 40%, even more preferably at least about 50%, even more preferably at least about 60%, even more preferably at least about 70%, even more preferably at least about 80%, even more preferably at least about 90%, sill even more preferably at least about 95%, greater than that of the target or first antigen. Assays for measuring degradation of proteins are known to persons of skill in the art. For example, proteolytic degradation may be measured using a mammalian cell lysate assay including, but not restricted to, the reticulocyte lysate assay of Bachmair et al in U.S. Pat. No. 5,646,017.

The second antigen may be derived from a parent antigen corresponding to the target antigen. The parent antigen is suitably selected from a natural antigen, a synthetic antigen or a combination thereof. Preferably, the parent antigen is modified to include an intracellular degradation signal or degron. The degron is suitably a ubiquitin-mediated degradation signal selected from a destabilising amino acid at the amino-terminus of an antigen, a ubiquitin acceptor, a ubiquitin or combination thereof.

Thus, in one embodiment, the parent antigen is modified to include a destabilising amino acid at its amino-terminus so that the protein so modified is subject to the N-end rule pathway as disclosed, for example, by Bachmair et al in U.S. Pat. No. 5,093,242 and by Varshavsky et al. in U.S. Pat. No. 5,122,463. In a preferred embodiment of this type, the destabilising amino acid is selected from isoleucine and glutamic acid, more preferably from histidine tyrosine and glutamine, and even more preferably from aspartic acid, asparagine, phenylalanine, leucine, tryptophan and lysine. In an especially preferred embodiment, the destabilising amino acid is arginine. In some proteins, the amino-terminal end is obscured as a result of the protein's conformation (i.e., its tertiary or quaternary structure). In these cases, more extensive alteration of the amino-terminus may be necessary to make the protein subject to the N-end rule pathway. For example, where simple addition or replacement of the single amino-terminal residue is insufficient because of an inaccessible amino-terminus, several amino acids (including lysine, the site of ubiquitin joining to substrate proteins) may be added to the original amino-terminus to increase the accessibility and/or segmental mobility of the engineered amino terminus.

Proteins can be designed or modified at the protein or nucleic acid level to provide a second antigen with the desired metabolic characteristics. A straightforward approach to modifying a parent protein in order to increase its metabolic stability is to directly engineer the amino-terminus of the protein at the protein level. To provide a desired amino-terminal amino acid, the amino-terminus of the protein of interest can be chemically altered, for example, by adding an amino acid of the destabilising class to the amino-terminus of a protein or polypeptide, employing an appropriate chemistry. Thus, for example, a stable protein can be destabilised by adding a destabilising amino acid to the amino-terminus. One distinct way to modify the amino-terminus of a protein would be to employ specific enzymes, amino acid-protein ligases, which catalyse post-translational addition of a single amino acid to the protein's amino-terminus. Other methods for non-genetic alterations of the same type can readily be ascertained by those skilled in the art.

Modification or design of the amino-terminus of a protein can also be accomplished at the genetic level. Conventional techniques of site-directed mutagenesis for addition or substitution of appropriate codons to the 5' end of an isolated or synthesised antigen-encoding polynucleotide can be employed to provide a desired amino-terminal structure for the encoded protein. For example, so that the protein expressed has the desired amino acid at its amino-terminus the appropriate codon for a destabilising amino acid can be inserted or built into the amino-terminus of the protein-encoding sequence. Where necessary, a nucleic acid sequence encoding the amino-terminal region of a protein can be modified to introduce one or more lysine residues in an appropriate context, which act as a ubiquitin acceptor as described in more detail below. This can be achieved most conveniently by employing DNA constructs encoding "universal destabilising segments". A universal destabilising segment comprises a nucleic acid construct which encodes a polypeptide structure, preferably segmentally mobile, containing one or more lysine residues, the codons for lysine residues being positioned within the construct such that when the construct is inserted into the coding sequence of the antigen-encoding polynucleotide, the lysine residues are sufficiently spatially proximate to the amino-terminus of the encoded protein to serve as the second determinant of the complete amino-terminal degradation signal. The insertion of such constructs into the 5' portion of a antigen-encoding polynucleotide would provide the encoded protein with a lysine residue (or residues) in an appropriate context for destabilisation.

The codon for the amino-terminal amino acid of the protein of interest can be made to encode the desired amino acid by, for example, site-directed mutagenesis techniques currently standard in the field. Suitable mutagenesis methods are described for example in the relevant sections of Ausubel, et al. (supra) and of Sambrook, et al., (supra). Alternatively, suitable methods for altering DNA are set forth, for example, in U.S. Pat. Nos. 4,184,917, 4,321,365 and 4,351,901, which are incorporated herein by reference. Instead of in vitro mutagenesis, the synthetic polynucleotide can be synthesised de novo using readily available machinery. Sequential synthesis of DNA is described, for example, in U.S. Pat. No. 4,293,652. However, it should be noted that the present invention is not dependent on, and not directed to, any one particular technique for constructing a polynucleotide encoding a modified antigen as described herein.

If the antigen-encoding polynucleotide is a synthetic or recombinant polynucleotide the appropriate 5' codon can be built-in during the synthetic process. Alternatively, nucleotides for a specific codon can be added to the 5' end of an isolated or synthesised polynucleotide by ligation of an appropriate nucleic acid sequence to the 5' (amino-terminus-encoding) end of the polynucleotide. Nucleic acid inserts encoding appropriately located lysine residues (such as the "universal destabilising segments" described above) can suitably be inserted into the 5' region to provide for the second determinant of the complete amino-terminal degradation.

In a preferred embodiment, the second or modified antigen, which comprises a destabilising amino acid at its amino terminus, is fused or otherwise conjugated to a masking entity, which masks said amino terminus so that when unmasked the second antigen will exhibit the desired rate of intracellular proteolytic degradation. Suitably, the masking entity is a masking protein sequence. The fusion protein is designed so that the masking protein sequence fused to the amino-terminus of the protein of interest is susceptible to specific cleavage at the junction between the two. Removal of the protein sequence thus unmasks the amino-terminus of the protein of interest and the half-life of the released protein is thus governed by the predesigned amino-terminus. The fusion protein can be designed for specific cleavage in vivo, for example, by a host cell endoprotease or for specific cleavage in a in vitro system where it can be cleaved after isolation from a producer cell (which lacks the capability to cleave the fusion protein). Thus, in a preferred embodiment, the masking protein sequence is cleavable by an endoprotease, which is preferably an endogenous endoprotease of a mammalian cell. Suitable endoproteases include, but are not restricted to, serine endoproteases (e.g., subtilisins and furins) as described, for example, by Creemers, et al. (1998, *Semin. Cell Dev. Biol.* 9 (1): 3-10), proteasomal endopeptidases as described, for example, by Zwickl, et al. (2000, *Curr. Opin. Struct. Biol.* 10 (2): 242-250), proteases relating to the MHC class I processing pathway as described, for example, by Stolze et al. (2000, *Nat. Immunol.* 1 413-418) and signal peptidases as described, for example, by Dalbey, et al. (1997, *Protein Sci.* 6 (6): 1129-1138). In a preferred embodiment of this type, the masking protein sequence comprises a signal peptide sequence. Suitable signal peptides sequences are described, for example, by Nothwehr et al. (1990, *Bioessays* 12 (10): 479-484), Izard, et al. (1994, *Mol. Microbiol.* 13 (5): 765-773), Menne, et al. (2000, *Bioinformatics.* 16 (8): 741-742) and Ladunga (2000, *Curr. Opin. Biotechnol.* 11 (1): 13-18). Suitably, an endoprotease cleavage site is interposed between the masking protein sequence and the second antigen.

A second or modified antigen with an attached masking sequence may be conveniently prepared by fusing a nucleic acid sequence encoding a masking protein sequence upstream of another nucleic acid sequence encoding an antigen, which corresponds to the target antigen of interest and which includes a destabilising amino acid at its amino-terminus. The codon for the amino-terminal amino acid of the antigen of interest is suitably located immediately adjacent to the 3' end of the masking protein-encoding nucleic acid sequence.

In another embodiment, the parent antigen is modified to include, or is otherwise associated with, an ubiquitin acceptor which is a molecule that preferably contains at least one residue appropriately positioned from the N-terminal of the antigen as to be able to be bound by ubiquitin molecules. Such residues preferentially have an epsilon amino group such as lysine. Physical analysis demonstrates that multiple lysine residues function as ubiquitin acceptor sites (King et al., 1996, *Mol. Biol. Cell* 7: 1343-1357; King et al., 1996, *Science* 274: 1652-1659). Examples of other ubiquitin acceptors include lacI or Sindis virus RNA polymerase. Ubiquitination at the N-terminal of the protein specifically targets the protein for degradation via the ubiquitin-proteosome pathway.

Other protein processing signals that destabilise an antigen of interest and allow for enhanced intracellular degradation are contemplated in the present invention. These other methods may not necessarily be mediated by the ubiquitin pathway, but may otherwise permit degradation of proteins in the cytoplasm via proteosomes. For example, the present invention contemplates the use of other intracellular processing signals which govern the rate(s) of intracellular protein degradation including, but not limited to, those described by Bohley et al. (1996, *Biol. Chem. Hoppe. Seyler* 377: 425-435). Such processing signals include those that allow for phosphorylation of the target protein (Yaglom et al., 1996, *Mol. Cell Biol.* 16: 3679-3684; Yaglom et al., 1995, *Mol. Cell Biol.* 15: 731-741). Also contemplated by the present invention are modification of an parent antigen that allow for post-translational arginylation (Ferber et al 1987, *Nature* 326: 808-811; Bohley et al., 1991, *Biomed. Biochim. Acta* 50: 343-346) of the protein which can enhance its rate(s) of intracellular degradation. The present invention also contemplates the use of certain structural features of proteins that can influence higher rates of intracellular protein turn-over, including protein surface hydrophobicity, clusters of hydrophobic residues within the protein (Sadis et al., 1995, *Mol. Cell Biol.* 15: 4086-4094), certain hydrophobic pentapeptide motifs at the protein's carboxy-terminus (C-terminus) (e.g., ARINV (SEQ ID NO: 25), as found on the C-terminus of ornthine decarboxylase (Ghoda et al., 1992, *Mol. Cell Biol.* 12: 2178-2185; Li, et al., 1994, *Mol. Cell Biol.* 14: 87-92), or AANDENYALAA (SEQ ID NO: 26), as found in C-terminal tags of aberrant polypeptides (Keiler et al., 1996, *Science* 271: 990-993) or PEST regions (regions rich in proline (P), glutamic acid (E), serine (S), and threonine (T), which are optionally flanked by amino acids comprising electropositive side chains (Rogers et al. 1986, *Science* 234 (4774): 364-368; 1988, *J. Biol. Chem.* 263: 19833-19842). Moreover, certain motifs have been identified in proteins that appear necessary and possibly sufficient for achieving rapid intracellular degradation. Such motifs include RXALGXIXN (SEQ ID NO: 27) region (where X=any amino acid) in cyclins (Glotzer et al., 1991, *Nature* 349: 132-138) and the KTKRNYSARD (SEQ ID NO: 28) motif in isocitrate lyase (Ordiz et al., 1996, *FEBS Lett.* 385:43-46).

The present invention also contemplates enhanced cellular degradation of a parent antigen which may occur by the incorporation into that antigen known protease cleavage sites. For example amyloid beta-protein can be cleaved by beta- and gamma-secretase (Iizuka et al. 1996, *Biochem. Biophys. Res. Commun.* 218: 238-242) and the two-chain vitamin K-dependent coagulation factor X can be cleaved by calcium-dependent endoprotease(s) in liver (Wallin et al., 1994, *Thromb. Res.* 73: 395-403).

In yet another embodiment, the parent antigen is conjugated to a ubiquitin or a biologically active fragment thereof, to produce a second or modified antigen whose rate of intracellular proteolytic degradation is increased, enhanced or otherwise elevated relative to the parent antigen. In a preferred embodiment of this type, the ubiquitin or biologically active fragment is fused, or otherwise conjugated, to the second antigen. Suitably, the ubiquitin is of mammalian origin, more preferably of human or other primate origin. In a preferred embodiment of this type, the ubiquitin comprises the sequence set forth in SEQ ID NO: 2. In an alternate embodiment, the ubiquitin comprises two or more copies the sequence set forth in SEQ ID NO: 2.

In one embodiment, the ubiquitin-antigen fusion protein is suitably produced by covalently attaching an antigen corresponding to the target antigen to a ubiquitin or a biologically active fragment thereof. Covalent attachment may be effected by any suitable means known to persons of skill in the art. For example, protein conjugates may be prepared by linking proteins together using bifunctional reagents. The bifunctional reagents can be homobifunctional or heterobifunctional.

Homobifunctional reagents are molecules with at least two identical functional groups. The functional groups of the reagent generally react with one of the functional groups on a protein, typically an amino group. Examples of homobifunctional reagents include glutaraldehyde and diimidates. An example of the use of glutaraldehyde as a cross-linking agent is described by Poznansky et al. (1984, *Science*, 223: 1304-1306). The use of diimidates as a cross-linking agent is described for example by Wang, et al. (1977, *Biochemistry*, 16: 2937-2941). Although it is possible to use homobifunctional reagents for the purpose of forming a modified antigen according to the invention, skilled practitioners in the art will appreciate that it is difficult to attach different proteins in an ordered fashion with these reagents. In this regard, in attempting to link a first protein with a second protein by means of a homobifunctional reagent, one cannot prevent the linking of the first protein to each other and of the second to each other. Heterobifunctional crosslinking reagents are, therefore, preferred because one can control the sequence of reactions, and combine proteins at will. Heterobifunctional reagents thus provide a more sophisticated method for linking two proteins. These reagents require one of the molecules to be joined, hereafter called Partner B, to possess a reactive group not found on the other, hereafter called Partner A, or else require that one of the two functional groups be blocked or otherwise greatly reduced in reactivity while the other group is reacted with Partner A. In a typical two-step process for forming heteroconjugates, Partner A is reacted with the heterobifunctional reagent to form a derivatised Partner A molecule. If the unreacted functional group of the crosslinker is blocked, it is then deprotected. After deprotecting, Partner B is coupled to derivatised Partner A to form the conjugate. Primary amino groups on Partner A are reacted with an activated carboxylate or imidate group on the crosslinker in the derivatisation step. A reactive thiol or a blocked and activated thiol at the other end of the crosslinker is reacted with an electrophilic group or with a reactive thiol, respectively, on Partner B. When the crosslinker possesses a reactive thiol, the electrophile on Partner B preferably will be a blocked and activated thiol, a maleimide, or a halomethylene carbonyl (e.g. bromoacetyl or iodoacetyl) group. Because biological macromolecules do not naturally contain such electrophiles, they must be added to Partner B by a separate derivatisation reaction. When the crosslinker possesses a blocked and activated thiol, the thiol on Partner B with which it reacts may be native to Partner B.

An example of a heterobifunctional reagent is N-succinimidyl 3-(2-pyridyldithio)propionate (SPDP) (see for example Carlsson et al., 1978, *Biochem. J.*, 173: 723-737). Other heterobifunctional reagents for linking proteins include for example succinimidyl 4-(N-maleimidomethyl) cyclohexane-1-carboxylate (SMCC) (Yoshitake et. al., 1979, *Eur. J. Biochem*, 101: 395-399), 2-iminothiolane (IT) (Jue et al., 1978, *Biochemistry*, 17: 5399-5406), and S-acetyl mercaptosuccinic anhydride (SAMSA) (Klotz and Heiney, 1962, *Arch. Biochem. Biophys.*, 96: 605-612). All three react preferentially with primary amines (e.g. lysine side chains) to form an amide or amidine group which links a thiol to the derivatized molecule (e.g. a heterologous antigen) via a connecting short spacer arm, one to three carbon atoms long. Examples of heterobifunctional reagents comprising reactive groups having a double bond that reacts with a thiol group include SMCC mentioned above, succinimidyl m-maleimidobenzoate, succinimidyl 3-(maleimido)propionate, sulfosuccinimidyl 4-(p-maleimidophenyl)butyrate, sulfosuccinimidyl 4-(N-maleimidomethylcyclohexane-1-carboxylate and maleimidobenzoyl-N-hychoxysuccinimide ester (MBS). In a preferred embodiment, MBS is used to produce the conjugate. Other heterobifunctional reagents for forming conjugates of two proteins are described for example by Rodwell et al. in U.S. Pat. No. 4,671,958 and by Moreland et al in U.S. Pat. No. 5,241,078.

In an alternate embodiment, a ubiquitin-antigen fusion protein is suitably expressed by a synthetic chimeric polynucleotide comprising a first nucleic acid sequence, which encodes an antigen corresponding to the target antigen, and which is linked downstream of, and in reading frame with, a second nucleic acid sequence encoding a ubiquitin or biologically active fragment thereof. In a preferred embodiment of this type, the second polynucleotide comprises a first nucleic acid sequence, which encodes an antigen corresponding to the target antigen, and which is linked immediately adjacent to, downstream of, and in reading frame with, a second nucleic acid sequence encoding a ubiquitin or biologically active fragment thereof. In another embodiment, the second polynucleotide comprises a first nucleic acid sequence, which encodes an antigen corresponding to the target antigen, and which is linked upstream of, and in reading frame with, a second nucleic acid sequence encoding a ubiquitin or biologically active fragment thereof. In yet another embodiment of this type, the second polynucleotide comprises a first nucleic acid sequence, which encodes an antigen corresponding to the target antigen, and which is linked immediately adjacent to, upstream of, and in reading frame with, a second nucleic acid sequence encoding a ubiquitin or biologically active fragment thereof. Preferably, but not exclusively, the ubiquitin-encoding nucleic acid sequence comprises the sequence set forth in SEQ ID NO: 1.

The invention further contemplates a synthetic construct (or expression vector), comprising a polynucleotide encoding a modified antigen as broadly described above, wherein said polynucleotide is operably linked to a regulatory polynucleotide. A polynucleotide encoding the modified antigen can be constructed from any suitable parent polynucleotide encoding an antigen that corresponds to the target antigen of interest. The parent polynucleotide is suitably a natural gene. However, it is possible that the parent polynucleotide is not naturally-occurring but has been engineered using recombinant techniques.

The regulatory polynucleotide suitably comprises transcriptional and/or translational control sequences, which will generally be appropriate for the host cell used for expression of the antigen-encoding polynucleotide. Typically, the transcriptional and translational regulatory control sequences include, but are not limited to, a promoter sequence, a 5' non-coding region, a cis-regulatory region such as a functional binding site for transcriptional regulatory protein or translational regulatory protein, an upstream open reading frame, transcriptional start site, translational start site, and/or nucleotide sequence which encodes a leader sequence, termination codon, translational stop site and a 3' non-translated region. Constitutive or inducible promoters as known in the art are contemplated by the invention. The promoters may be either naturally occurring promoters, or hybrid promoters that combine elements of more than one promoter. Promoter sequences contemplated by the present invention may be native to the host cell to be introduced or may be derived from an alternative source, where the region is functional in the host cell.

The synthetic construct of the present invention may also comprise a 3' non-translated sequence. A 3' non-translated sequence refers to that portion of a gene comprising a DNA segment that contains a polyadenylation signal and any other regulatory signals capable of effecting mRNA processing or gene expression. The polyadenylation signal is characterised by effecting the addition of polyadenylic acid tracts to the 3' end of the mRNA precursor. Polyadenylation signals are commonly recognised by the presence of homology to the canonical form 5' AATAAA-3' although variations are not uncommon. The 3' non-translated regulatory DNA sequence preferably includes from about 50 to 1,000 nucleotide base pairs and may contain transcriptional and translational termination sequences in addition to a polyadenylation signal and any other regulatory signals capable of effecting mRNA processing or gene expression.

In a preferred embodiment, the expression vector further contains a selectable marker gene to allow the selection of transformed host cells. Selection genes are well known in the art and will vary with the host cell used.

The expression vector may also include a fusion partner (typically provided by the expression vector) so that the recombinant polypeptide of the invention is expressed as a fusion polypeptide with said fusion partner. The main advantage of fusion partners is that they assist identification and/or purification of said fusion polypeptide. In order to express said fusion polypeptide, it is necessary to ligate an antigen-encoding polynucleotide according to the invention into the expression vector so that the translational reading frames of the fusion partner and the polynucleotide coincide. Well known examples of fusion partners include, but are not limited to, glutathione-S-transferase (GST), Fc portion of human IgG, maltose binding protein (MBP) and hexahistidine ($HIS_6$), which are particularly useful for isolation of the fusion polypeptide by affinity chromatography. For the purposes of fusion polypeptide purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with ($HIS_6$) fusion partners and the Pharmacia GST purification system. In a preferred embodiment, the recombinant polynucleotide is expressed in the commercial vector pFLAG as described more fully hereinafter. Another fusion partner well known in the art is green fluorescent protein (GFP). This fusion partner serves as a fluorescent "tag" which allows the fusion polypeptide of the invention to be identified by fluorescence microscopy or by flow cytometry. The GFP tag is useful when assessing subcellular localisation of the fusion polypeptide of the invention, or for isolating cells which express the fusion polypeptide of the invention. Flow cytometric methods such as fluorescence activated cell sorting (FACS) are particularly useful in this latter application. Preferably, the fusion partners also have protease cleavage sites, such as for Factor $X_a$ or Thrombin, which allow the relevant protease to partially digest the fusion polypeptide of the invention and thereby liberate the recombinant polypeptide of the invention therefrom. The liberated polypeptide can then be isolated from the fusion partner by subsequent chromatographic separation. Fusion partners according to the invention also include within their scope "epitope tags", which are usually short peptide sequences for which a specific antibody is available. Well known examples of epitope tags for which specific monoclonal antibodies are readily available include c-Myc, influenza virus haemagglutinin and FLAG tags.

The step of introducing into the host cell the recombinant polynucleotide may be effected by any suitable method including transfection, and transformation, the choice of which will be dependent on the host cell employed. Such methods are well known to those of skill in the art.

Recombinant polypeptides of the invention may be produced by culturing a host cell transformed with an expression vector containing nucleic acid encoding a polypeptide, biologically active fragment, variant or derivative according to the invention. The conditions appropriate for protein expression will vary with the choice of expression vector and the host cell. This is easily ascertained by one skilled in the art through routine experimentation. Suitable host cells for expression may be prokaryotic or eukaryotic. One preferred host cell for expression of a polypeptide according to the invention is a bacterium. The bacterium used may be *Escherichia coli*. Alternatively, the host cell may be an insect cell such as, for example, SF9 cells that may be utilised with a baculovirus expression system.

The recombinant protein may be conveniently prepared by a person skilled in the art using standard protocols as for example described in Sambrook, et al., MOLECULAR CLONING. A LABORATORY MANUAL (Cold Spring Harbor Press, 1989), in particular Sections 16 and 17; Ausubel et al., CURRENT PROTOCOLS IN MOLECULAR BIOLOGY (John Wiley & Sons, Inc. 1994-1998), in particular Chapters 10 and 16; and Coligan et al., CURRENT PROTOCOLS IN PROTEIN SCIENCE (John Wiley & Sons, Inc. 1995-1997), in particular Chapters 1, 5 and 6.

Alternatively, the modified antigen may be synthesised using solution synthesis or solid phase synthesis as described, for example, in Chapter 9 of Atherton and Shephard (supra) and in Roberge et al (1995, *Science* 269: 202).

3.2 Production of Unmodified Antigens (First Antigens)

Unmodified antigen, for use in producing the immunomodulatory compositions of the invention, may be prepared by any suitable technique. By "unmodified antigen" is meant any antigen, whether natural or synthetic that mimics or retains the intracellular proteolytic degradation of the target antigen. Accordingly, the unmodified antigen may be isolated from a natural source or may be prepared by recombinant techniques as is known in the art. Preferably, the unmodified antigen is prepared in recombinant form as for example described above for the modified antigens of the invention. For example, an unmodified antigen may be prepared by a procedure including the steps of (a) providing a polynucleotide encoding an unmodified antigen, which is operably linked to a regulatory polynucleotide; (b) introducing the polynucleotide into a suitable host cell; (c) culturing the host cell to express recombinant polypeptide from said polynucleotide; and (d) isolating the recombinant polypeptide.

The invention also envisions a synthetic construct, comprising a polynucleotide encoding an unmodified antigen as broadly described above, wherein said polynucleotide is operably linked to a regulatory polynucleotide. A polynucleotide encoding the unmodified antigen can be constructed from any suitable parent polynucleotide, which codes for an antigen that corresponds to the target antigen of interest. The parent polynucleotide is suitably a natural gene. However, it is possible that the parent polynucleotide is not naturally-occurring but has been engineered using recombinant techniques.

4. Codon Optimisation of Antigen-Encoding Polynucleotides

The codon composition of antigen-encoding polynucleotides may be altered to enhance the expression of the antigen in a particular cell or tissue. Such codon optimisation is predicated on the replacement of existing codons in a parent polynucleotide with synonymous codons that have a higher translational efficiency in a chosen cell or tissue. Any suitable method of replacing synonymous codons for existing codons is contemplated by the present invention. For example, reference may be made to International Application Publication No WO 96/09378 which utilise such substitution to provide a method of expressing proteins of eukaryotic and viral origin at high levels in in vitro mammalian cell culture systems. Preferably, the codon composition of the polynucleotide is modified to permit selective expression of the antigen encoded thereby in a target cell or tissue of choice using methods as set forth in detail in International Application Publication Nos WO 99/02694 and WO 00/42215. In this regard, the present inventors were able to show in WO 99/02694 and in copending U.S. application Ser. No. 09/479,645 that there are substantial differences in the relative abundance of particular isoaccepting transfer RNAs in different cells or tissues of an organism (e.g., a mammal) and that this plays a pivotal role in protein expression from a coding sequence with a given codon usage or composition. Modification of the codons utilised in transgenes designed to generate translated proteins can lead to much higher and selective expression of particular genes in a cell or tissue of interest. Briefly, the method is based on the observation that translational efficiencies of different codons vary between different cells or tissues. Such differences can be exploited, together with codon composition of a gene, to regulate and direct expression of a protein or a functional fragment or epitope thereof to a particular cell or cell type, including cells in a selected tissue. Codons are selected such that the synonymous codon has a higher translational efficiency in a target cell or tissue relative to one or more other cells or tissues.

One or more codons in a gene may be substituted in order to target expression of the gene to particular cells or tissues. It is preferable but not necessary to replace all the existing codons of the parent nucleic acid molecule with synonymous codons having higher translational efficiencies in the target cell or tissue compared to the other cells or tissues. Increased expression can be accomplished even with partial replacement. Suitably, the replacement step affects 5%, 10%, 15%, 20%, 25%, 30%, more preferably 35%, 40%, 50%, 60%, 70% or more of the existing codons of the parent polynucleotide. The difference in level of protein expressed in the desired target cell or tissue from a synthetic polynucleotide, relative to that expressed in the other cells or tissues, depends on the percentage of existing codons replaced by synonymous codons and the difference in translational efficiencies of the synonymous codons in the target cell or tissue, relative to the other cells or tissues.

By optimising codon content, according to the procedures disclosed in WO 99/02694 and in copending U.S. application Ser. No. 09/479,645, it has been shown that a protein can be expressed from a synthetic polynucleotide in a target cell or tissue at levels greater than 10,000-fold over those expressed in another cell or tissue. A nucleic acid molecule, which has undergone such codon modification, is referred to herein as "optimised".

5. Synthetic Constructs of the Invention

The invention also provides a synthetic construct for eliciting a humoral and a cellular immune response against a target antigen, comprising a first polynucleotide encoding a first antigen corresponding to the target antigen; and a second polynucleotide encoding a second antigen, corresponding to a modified form of the target antigen, whose rate of intracellular proteolytic degradation is increased, enhanced or otherwise elevated relative to the first antigen. In one embodiment the first polynucleotide and the second polynucleotide are operably linked to a regulatory polynucleotide. For example, the first and second polynucleotides may be expressed from a single promoter. In an alternate embodiment, the first polynucleotide and the second polynucleotide are operably linked to different regulatory polynucleotides. For example, the first and second polynucleotides may be expressed from different promoters.

The invention also contemplates a synthetic construct system for eliciting a humoral and a cellular immune response against a target antigen, comprising a synthetic construct comprising a first polynucleotide, which encodes a first antigen corresponding to the target antigen, and which is operably linked to a regulatory polynucleotide; and another synthetic construct comprising a second polynucleotide encoding a second antigen, which corresponds to a modified form of the target antigen, whose rate of intracellular proteolytic degradation is increased, enhanced or otherwise elevated relative to the first antigen, wherein said second polynucleotide is operably linked to a regulatory polynucleotide.

6. Delivery of Antigens to Cytosol

Modified and unmodified antigens according to the present invention or polynucleotides from which they are expressible may be linked to, or otherwise associated with, a cytolysin to enhance the transfer of the antigens into the cytosol of a target cell for delivery to the MHC class I pathway. Exemplary cytolysins include saponin compounds such as saponin-containing Immune Stimulating Complexes (ISCOMs) (see e.g., Cox and Coulter, 1997, *Vaccine* 15(3): 248-256 and U.S. Pat. No. 6,352,697), phospholipases (see, e.g., Camilli et al., 1991, *J. Exp. Med.* 173: 751-754), pore-forming toxins (e.g., an alpha-toxin), natural cytolysins of gram-positive bacteria, such as listeriolysin O (LLO, e.g., Mengaud et al., 1988, *Infect. Immun.* 56: 766-772 and Portnoy et al., 1992, *Infect. Immun.* 60: 2710-2717), streptolysin O (SLO, e.g., Palmer et al., 1998, *Biochemistry* 37(8): 2378-2383) and perfringolysin O (PFO, e.g., Rossjohn et al., *Cell* 89(5): 685-692). Where the target cell is phagosomal, acid activated cytolysins may be advantageously used. For example, listeriolysin exhibits greater pore-forming ability at mildly acidic pH (the pH conditions within the phagosome), thereby facilitating delivery of vacuole (including phagosome and endosome) contents to the cytoplasm (see, e.g., Portnoy et al., *Infect. Immun.* 1992, 60: 2710-2717).

The cytolysin may be provided together with one or both of the modified and unmodified antigens of the present invention in the form of a single composition or may be provided as a separate composition. In one embodiment, the cytolysin is fused or otherwise linked to one or both of said antigens, wherein the fusion or linkage permits the delivery of the antigen(s) to the cytosol of the target cell. In another embodiment, the cytolysin and antigen(s) are provided in the form of a delivery vehicle such as, but not limited to, a liposome or a microbial delivery vehicle selected from virus, bacterium, or yeast. Suitably, when the delivery vehicle is a microbial delivery vehicle, the delivery vehicle is non-virulent. In a preferred embodiment of this type, the delivery vehicle is a non-virulent bacterium, as for example described by Portnoy et al. in U.S. Pat. No. 6,287,556, comprising a first polynucleotide encoding a non-secreted functional cytolysin operably linked to a regulatory polynucleotide which expresses the cytolysin in the bacterium, and a second polynucleotide encoding one or more of said target antigens. Non-secreted cytolysins may be provided by various mechanisms, e.g. absence of a functional signal sequence, a secretion incompetent microbe, such as microbes having genetic lesions (e.g. a functional signal sequence mutation), or poisoned microbes, etc. A wide variety of nonvirulent, non-pathogenic bacteria may be used; preferred microbes are relatively well characterised strains, particularly laboratory strains of *E. coli*, such as MC4100, MC1061, DH5.alpha., etc. Other bacteria that can be engineered for the invention include well-characterised, nonvirulent, non-pathogenic strains of *Listeria monocytogenes, Shigella flexneri, mycobacterium, Salmonella, Bacillus subtilis*, etc. In a particular embodiment, the bacteria are attenuated to be non-replicative, non-integrative into the host cell genome, and/or non-motile inter- or intra-cellularly.

The delivery vehicles described above can be used to deliver one or more antigens of the invention to virtually any target cell capable of endocytosis of the subject vehicle, including phagocytic, non-phagocytic, pathogenic or diseased cells. Exemplary target animal cells include epithelial cells, endothelial cells, muscle cells, liver cells, pancreatic cells, neural cells, fibroblasts, tumour cells, leukocytes such as macrophages, neutrophils, B-cells, T-cells, monocytes, etc. In embodiments when the delivery vehicle is a microbe, the subject methods generally require microbial uptake by the target cell and subsequent lysis within the target cell vacuole (including phagosomes and endosomes). While phagocytic target cells generally provide for microbial uptake and lysis, for many cell types, it is necessary to provide the microbe (e.g., bacterium) with an invasin to facilitate or mediate uptake by the target cell and an autolysin to facilitate or mediate autolysis of the microbe within the target cell vacuole, as for example described by Portnoy et al. in U.S. Pat. No. 6,287,556.

7. Antigen-Presenting Cell Embodiments

The invention further provides a composition of matter for eliciting a humoral and a cellular immune response against a target antigen, comprising antigen-presenting cells which express a processed form of the first antigen as broadly described above, and a processed form of the second antigen as broadly described above, for presentation to, and modulation of, T cells. Antigen-primed antigen-presenting cells may be prepared by a method including contacting antigen-presenting cells with (1) a first antigen as broadly described above or a polynucleotide from which the first antigen is expressible, and (2) a second antigen as broadly described above or a polynucleotide from which the second antigen is expressible, for a time and under conditions sufficient to permit said first and second antigens to be internalised by the antigen-presenting cells; and culturing the antigen-containing antigen-presenting cells for a time and under conditions sufficient for the antigen(s) to be processed for presentation by the antigen-presenting cells. The antigen-presenting cells may be selected from dendritic cells, macrophages and B cells. In preferred embodiments of the invention, the antigen-presenting cells are dendritic cells.

7.1 Sources of Dendritic Cells

Dendritic cells can be isolated by methods known to those of skill in the art. Suitably, mammalian and preferably human dendritic cells are used from an appropriate tissue source, which is suitably blood or bone marrow. Dendritic cell precursors, from which the immature dendritic cells for use in antigen internalisation according to the invention, are present in blood as peripheral blood mononuclear cells (PBMCs). Although most easily obtainable from blood, the precursor cells may also be obtained from any tissue in which they reside, including bone marrow and spleen tissue. Peripheral blood precursors may be purified using monoclonal antibodies, density gradients or centrifugation or any combination of these. Circulating frequency may be increased in vivo using flt-3 ligand. When cultured in the presence of cytokines such as a combination of GM-CSF and IL-4 or IL-13 as described below, the non-proliferating precursor cells give rise to immature dendritic cells for use in this invention.

An exemplary method for culturing pluripotential PBMCs to produce immature dendritic cells is described by Albert et al. (International Publication WO 99/42564). In this respect, cultures of immature dendritic cells, i.e. antigen-capturing phagocytic dendritic cells, may be obtained by culturing non-proliferating precursor cells (PBMCs) in the presence of cytokines which promote their differentiation. A combination of GM-CSF and IL-4 produces significant quantities of the immature dendritic cells, i.e. antigen-capturing phagocytic or internalisation-competent dendritic cells. Other cytokines that promote differentiation of precursor cells into immature dendritic cells include, but are not limited to, IL-13.

Maturation of dendritic cells requires the addition to the cell environment, preferably the culture medium, of a dendritic cell one or more maturation factors which may be selected from monocyte conditioned medium and/or factors including TNF-α IL-6, IFN-α and IL-1. Alternatively, a mixture of necrotic cells or necrotic cell lysate may be added to induce maturation. Maturation can be induced in vitro using plastic adherence, cytokines, LPS, bacteria, DNA containing CpG repeats, RNA or polyIC, CD40-ligation, necrotic cells. In this regard, reference may be made to Steinman et al. (International Publication WO 97/29182) who describe methods and compositions for isolation and maturation of dendritic cells.

Other methods for isolation, expansion and/or maturation of dendritic cells for the upurpose of the present invention are described for example by Takamizawa et al. (1997, *J*

*Immunol,* 158 (5): 2134-2142), Thomas and Lipsky (1994, *J Immunol,* 153 (9): 4016-4028), O'Doherty et al. (1994, *Immunology,* 82 (3): 487-93), Fearnley et al. (1997, *Blood,* 89 (10): 3708-3716), Weissman et al. (1995, *Proc Natl Acad Sci USA,* 92 (3): 826-830), Freudenthal and Steinman (1990, *Proc Natl Acad Sci USA,* 87 (19): 7698-7702), Romani et al. (1996, *J Immunol Methods,* 196 (2): 137-151), Reddy et al. (1997, *Blood,* 90 (9): 3640-3646), Thurnher et al. (1997, *Exp Hematol,* 25 (3): 232-237), Caux et al. (1996, *J Exp Med,* 184 (2): 695-706; 1996, *Blood,* 87 (6): 2376-85), Luft et al. (1998, *Exp Hematol,* 26 (6): 489-500; 1998, *J Immunol,* 161 (4): 1947-1953), Cella et al. (1999, *J Exp Med,* 189 (5): 821-829; 1997, *Nature,* 388 (644): 782-787; 1996, *J Exp Med,* 184 (2): 747-572), Ahonen et al. (1999, *Cell Immunol,* 197(1): 62-72) and Piemonti et al. (1999, *J Immunol,* 162 (11): 6473-6481).

Alternatively, transformed or immortalised dendritic cell lines may be produced using oncogenes such as v-myc as for example described by Paglia et al. (1993, *J Exp Med,* 178 (6): 1893-1901).

7.2 Antigen Priming of Antigen-Presenting Cells

The amount of antigen to be placed in contact with antigen-presenting cells, which are preferably dendritic cells, can be determined empirically by persons of skill in the art. Antigen-presenting cells (which are preferably dendritic cells, are incubated with the antigen for 1-2 hr at 37° C. For most antigens, 10 µg/mL to 1-10 million dendritic cells is suitable for priming the dendritic cells. In a preferred embodiment, immature dendritic cells are utilised for the antigen internalisation.

The antigen(s) should be exposed to the antigen-presenting cells for a period of time sufficient for the antigen-presenting cells to internalise the antigen(s). The time necessary for the cells to internalise and present the processed antigen(s) may be determined using pulse-chase protocols in which exposure to antigen(s) is followed by a washout period. Once the minimum time necessary for cells to express processed antigen(s) on their surface is determined, a protocol may be used to prepare cells and antigen(s) for eliciting immunogenic responses. Those of skill in the art will recognise in this regard that the length of time necessary for an antigen-presenting cell to phagocytose or internalise a antigen may vary depending on the antigen used. Efficiency of priming of the antigen-presenting cells can be determined by assaying T cell cytotoxic activity in vitro or using antigen-presenting cells as targets of CTLs. Other methods known to practitioners in the art, which can detect the presence of antigen on the surface of antigen-presenting cells after exposure to one or more of the modified and unmodified antigens, are also contemplated by the presented invention.

In preferred embodiments where the antigen-presenting cells are dendritic cells, such cells have the capacity to efficiently present a processed form of the modified antigen and the unmodified antigen in the form of peptides on both MHC class I and class II molecules. Antigens are acquired by dendritic cells through the exogenous pathway by phagocytosis and, as a result, efficiently charge MHC class II molecules. Accordingly, both $CD4^+$ T helper lymphocytes and CTL may be activated by dendritic cells presenting modified and optionally unmodified antigen in the context of MHC class II. These lymphocytes can provide critical sources of help, both for generating active $CD8^+$ CTL and can in some circumstances be primed as $CD4^+$ CTL with specificity for the target antigen during the acute response to antigen, and for generating the memory that is required for long term resistance and vaccination. Further, modified antigen and optionally unmodified antigen uptake and presentation by dendritic cells, allows these cells to tailor the peptides that are appropriate for an individuals MHC products, and increases the number of specialised stimulatory antigen-presenting cells. Moreover, dendritic cells can be charged with multiple antigens on multiple MHCs to yield polyclonal or oligoclonal stimulation of T cells. Thus, by using the antigens of the present invention to charge MHC class I and class II molecules, efficient T cell modulation in situ can be achieved.

8. Compositions

The modified antigens and unmodified antigens described respectively in Sections 3 and 4, the synthetic construct and synthetic construct system described in Section 5, and the antigen-primed antigen-presenting cells described in Section 7 (therapeutic/prophylactic agents) can be used as active ingredients for the treatment or prophylaxis of various conditions associated with the presence of a target antigen. These therapeutic/prophylactic agents can be administered to a patient either by themselves, or in compositions where they are mixed with a suitable pharmaceutically acceptable carrier and/or diluent, or an adjuvant.

The invention also encompasses a method for stimulating a patient's immune system, and preferably for eliciting a humoral and a cellular immune response against a target antigen, by administering to the patient a therapeutic agent or composition as described above. Such stimulation may be utilised for the treatment and/or prophylaxis of a disease or condition including, but not restricted to, a pathogenic infection (e.g., viral, bacterial, fungal, protozoan). Alternatively, the stimulation can be used to modulate an immune response to an autoantigen (e.g., associated with Rheumatoid arthritis).

Thus, the invention contemplates a method for treatment and/or prophylaxis of a disease or condition, comprising administering to a patient in need of such treatment a therapeutically/prophylactically effective amount of a composition as broadly described above. In one embodiment, the method comprises administering concurrently to the patient an unmodified antigen as broadly described above, or a polynucleotide from which the unmodified antigen is expressible, together with a modified antigen as broadly described above, or a polynucleotide from which the modified antigen is expressible. In another embodiment, the method comprises coadministering to a patient a polynucleotide from which said unmodified antigen is expressible, and a polynucleotide from which said modified antigen is expressible. In yet another embodiment, the method comprises coadministering to a patient said unmodified antigen and a polynucleotide from which said modified antigen is expressible. In still yet another embodiment, the method comprises concurrently administering to a patient a polynucleotide from which said unmodified antigen is expressible, together with said modified antigen. In a further embodiment, the method comprises coadministering to a patient said unmodified antigen and antigen-presenting cells which have been exposed to said modified antigen, or a polynucleotide from which said modified antigen is expressible, for a time and under conditions sufficient to express a processed form of said modified antigen for presentation to, and modulation of, T cells. In still a further embodiment, the method comprises administering concurrently to a patient antigen-presenting cells which have been exposed to said modified antigen, or a polynucleotide from which said modified antigen is-expressible, and to said unmodified antigen, or a polynucleotide from which said unmodified antigen is expressible, for a time and under conditions sufficient to express a processed form of said modified antigen and a processed form of said unmodified antigen for presentation to, and modulation of, T cells.

Depending on the specific conditions being treated, therapeutic/prophylactic agents may be formulated and administered systemically or locally. Techniques for formulation and administration may be found in "Remington's Pharmaceutical Sciences," Mack Publishing Co., Easton, Pa., latest edition. Suitable routes may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. For injection, the therapeutic agents of the invention may be formulated in aqueous solutions, preferably in physiologically compatible buffers such as Hanks' solution, Ringer's solution, or physiological saline buffer. For transmucosal administration, penetrants appropriate to the barrier to be permeated are used in the formulation. Such penetrants are generally known in the art. Intra-muscular and subcutaneous injection is appropriate, for example, for administration of immunogenic compositions, vaccines and DNA vaccines.

The therapeutic/prophylactic agents can be formulated readily using pharmaceutically acceptable carriers well known in the art into dosages suitable for oral administration. Such carriers enable the compounds of the invention to be formulated in dosage forms such as tablets, pills, capsules, liquids, gels, syrups, slurries, suspensions and the like, for oral ingestion by a patient to be treated. These carriers may be selected from sugars, starches, cellulose and its derivatives, malt, gelatine, talc, calcium sulphate, vegetable oils, synthetic oils, polyols, alginic acid, phosphate buffered solutions, emulsifiers, isotonic saline, and pyrogen-free water.

Pharmaceutical compositions suitable for use in the present invention include compositions wherein the active ingredients are contained in an effective amount to achieve its intended purpose. The dose of agent administered to a patient should be sufficient to effect a beneficial response in the patient over time such as a reduction in the symptoms associated with the condition. The quantity of the therapeutic/prophylactic agent(s) to be administered may depend on the subject to be treated inclusive of the age, sex, weight and general health condition thereof. In this regard, precise amounts of the therapeutic/prophylactic agent(s) for administration will depend on the judgement of the practitioner. In determining the effective amount of the agent to be administered in the treatment or prophylaxis of the condition, the physician may evaluate tissue levels of a target antigen, and progression of the disease or condition. In any event, those of skill in the art may readily determine suitable dosages of the therapeutic agents of the invention.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilisers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Such compositions may be prepared by any of the methods of pharmacy but all methods include the step of bringing into association one or more therapeutic agents as described above with the carrier which constitutes one or more necessary ingredients. In general, the pharmaceutical compositions of the present invention maybe manufactured in a manner that is itself known, e.g., by means of conventional mixing, dissolving, granulating, dragee-making, levigating, emulsifying, encapsulating, entrapping or lyophilising processes.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterise different combinations of active compound doses.

Pharmaceutical which can be used orally include push-fit capsules made of gelatin, as well as soft, sealed capsules made of gelatin and a plasticiser, such as glycerol or sorbitol. The push-fit capsules can contain the active ingredients in admixture with filler such as lactose, binders such as starches, and/or lubricants such as talc or magnesium stearate and, optionally, stabilisers. In soft capsules, the active compounds may be dissolved or suspended in suitable liquids, such as fatty oils, liquid paraffin, or liquid polyethylene glycols. In addition, stabilisers may be added.

Dosage forms of the therapeutic agents of the invention may also include injecting or implanting controlled releasing devices designed specifically for this purpose or other forms of implants modified to act additionally in this fashion. Controlled release of an agent of the invention may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, controlled release may be effected by using other polymer matrices, liposomes and/or microspheres.

Therapeutic agents of the invention may be provided as salts with pharmaceutically compatible counterions. Pharmaceutically compatible salts may be formed with many acids, including but not limited to hydrochloric, sulphuric, acetic, lactic, tartaric, malic, succinic, etc. Salts tend to be more soluble in aqueous or other protonic solvents that are the corresponding free base forms.

For any compound used in the method of the invention, the effective dose can be estimated initially from cell culture assays. For example, a dose can be formulated in animal models to achieve a circulating concentration range that includes the IC50 as determined in cell culture (e.g., the concentration of a test agent, which achieves a half-maximal reduction in target antigen). Such information can be used to more accurately determine useful doses in humans.

Toxicity and therapeutic efficacy of the compounds of the invention can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilised. The exact formulation, route of administration and dosage can be chosen by the individual physician in view of the patient's condition. (See for example Fingl et al., 1975, in "The Pharmacological Basis of Therapeutics", Ch. 1 p1).

Dosage amount and interval may be adjusted individually to provide plasma levels of the active compound(s) which are sufficient to maintain target antigen-reducing effects or effects that ameliorate the disease or condition. Usual patient dosages for systemic administration range from 1-2000 mg/day, commonly from 1-250 mg/day, and typically from 10-150 mg/day. Stated in terms of patient body weight, usual dosages range from 0.02-25 mg/kg/day, commonly from 0.02-3 mg/kg/day, typically from 0.2-1.5 mg/kg/day. Stated in terms of patient body surface areas, usual dosages range from 0.5-1200 mg/m$^2$/day, commonly from 0.5-150 mg/m$^2$/day, typically from 5-100 mg/m$^2$/day.

Alternately, one may administer the agent in a local rather than systemic manner, for example, via injection of the compound directly into a tissue, often in a depot or sustained release formulation. Furthermore, one may administer the agent in a targeted drug delivery system, for example, in a liposome coated with tissue-specific antibody. The liposomes will be targeted to and taken up selectively by the tissue.

From the foregoing, it will be appreciated that the agents of the invention may be used as therapeutic or prophylactic immunomodulating compositions or vaccines. Accordingly, the invention extends to the production of immunomodulating compositions containing as active compounds one or more of the therapeutic/prophylactic agents of the invention. Any suitable procedure is contemplated for producing such vaccines. Exemplary procedures include, for example, those described in NEW GENERATION VACCINES (1997, Levine et al., Marcel Dekker, Inc. New York, Basel Hong Kong).

A preferred aspect of the present invention contemplates the use of nucleic acid compositions for the purpose of vaccination or immunomodulation. In this regard, a synthetic construct can be used to immunise a patient, which construct includes a polynucleotide encoding a modified antigen according to the invention, and/or a polynucleotide encoding an unmodified antigen according to the invention, wherein said polynucleotide(s) is operably connected to one or more regulatory sequences that direct expression of said polynucleotide(s) in said patient.

Typically, such constructs or vectors are derived from viral DNA sequences such as adenovirus, adeno-associated viruses, herpes-simplex viruses and retroviruses. Suitable immunomodulating vectors currently available to the skilled person may be found, for example, in Wu and Ataai (2000, *Curr. Opin. Biotechnol* 11 (2): 205-208), Vigna and Naldini (2000, *J. Gene Med.* 2 (5): 308-316), Kay, et al. (2001, *Nat. Med.* 7 (1): 33-40), Athanasopoulos, et al. (2000, *Int. J. Mol. Med.* 6 (4): 363-375) and Walther and Stein (2000, *Drugs* 60 (2): 249-271).

Administration of the immunomodulating construct to a patient, preferably a human patient, may include delivery via direct oral intake, systemic injection, or delivery to selected tissue(s) or cells, or indirectly via delivery to cells isolated from the patient or a compatible donor. In a preferred embodiment, the immunomodulating construct is delivered intradermally. Delivery of said immunomodulating construct to cells or tissues of the patient or said compatible donor may be facilitated by microprojectiie bombardment, liposome mediated transfection (e.g., lipofectin or lipofectamine), electroporation, calcium phosphate or DEAE-dextran-mediated transfection, for example. A discussion of suitable delivery methods may be found in Chapter 9 of CURRENT PROTOCOLS IN MOLECULAR BIOLOGY (Eds. Ausubel et al.; John Wiley & Sons Inc., 1997 Edition), for example, which is herein incorporated by reference.

The step of introducing the immunomodulating construct into a target cell or tissue will differ depending on the intended use and species, and can involve one or more of non-viral and viral vectors, cationic liposomes, retroviruses, and adenoviruses such as, for example, described in Mulligan, R. C., (1993). Such methods can include, for example:

A. Local application of the expression vector by injection (Wolff et al., 1990), surgical implantation, instillation or any other means. This method can also be used in combination with local application by injection, surgical implantation, instillation or any other means, of cells responsive to the protein encoded by the expression vector so as to increase the effectiveness of that treatment. This method can also be used in combination with local application by injection, surgical implantation, instillation or any other means, of another factor or factors required for the activity of said protein.

B. General systemic delivery by injection of DNA, (Calabretta et al., 1993), or RNA, alone or in combination with liposomes (Zhu et al., 1993), viral capsids or nanoparticles (Bertling et al., 1991) or any other mediator of delivery. Improved targeting might be achieved by linking the polynucleotide/expression vector to a targeting molecule (the so-called "magic bullet" approach employing, for example, an antigen-binding molecule), or by local application by injection, surgical implantation or any other means, of another factor or factors required for the activity of the protein encoded by said expression vector, or of cells responsive to said protein.

C. Injection or implantation or delivery by any means, of cells that have been modified ex vivo by transfection (for example, in the presence of calcium phosphate: Chen et al., 1987, or of cationic lipids and polyamines: Rose et al., 1991), infection, injection, electroporation (Shigekawa et al., 1988) or any other way so as to increase the expression of said polynucleotide in those cells. The modification can be mediated by plasmid, bacteriophage, cosmid, viral (such as adenoviral or retroviral; Mulligan, 1993; Miller, 1992; Salmons et al., 1993) or other vectors, or other agents of modification such as liposomes (Zhu et al., 1993), viral capsids or nanoparticles (Bertling et al., 1991), or any other mediator of modification. The use of cells as a delivery vehicle for genes or gene products has been described by Barr et al., 1991 and by Dhawan et al., 1991. Treated cells can be delivered in combination with any nutrient, growth factor, matrix or other agent that will promote their survival in the treated subject.

Immmunomodulating compositions according to the present invention can contain a physiologically acceptable diluent or excipient such as water, phosphate buffered saline and saline. They may also include an adjuvant as is well known in the art. Suitable adjuvants include, but are not limited to: surface active substances such as hexadecylamine, octadecylamine, octadecyl amino acid esters, lysolecithin, dimethyldioctadecylaminonium bromide, N,N-dicoctadecyl-N', N'bis(2-hydroxyethyl-propanediamine), methoxyhexadecylglycerol, and pluronic polyols; polyamines such as pyran, dextransulfate, poly IC carbopol; peptides such as muramyl dipeptide and derivatives, dimethylglycine, tuftsin; oil emulsions; and mineral gels such as aluminum phosphate, aluminum hydroxide or alum; lymphokines, QuilA and immune stimulating complexes (ISCOMS).

The modified antigen-primed, and optionally unmodified antigen-primed, antigen-presenting cells of the invention and antigen-specific T lymphocytes generated with these antigen-presenting cells can be used as active compounds in immunomodulating compositions for prophylactic or therapeutic applications. The primed cells, which are preferably mature dendritic cells, can be injected by any method that elicits an immune response into a syngeneic animal or human. Preferably, antigen-presenting cells are injected back into the same animal or human from whom the source tissue/cells was obtained. The injection site may be subcutaneous, intraperitoneal, intramuscular, intradermal, or intravenous. The number of antigen-primed antigen-presenting cells reinjected back into the animal or human in need of treatment may vary depending on inter alia, the antigen and size of the individual. This number may range for example between about $10^4$ and $10^8$, and more preferably between about $10^6$ and $10^7$ antigen-primed antigen-presenting cells (e.g., dendritic cells). The antigen-presenting cells should be administered in a pharmaceutically acceptable carrier, which is non-toxic to the cells and the individual. Such carrier may be the growth medium in which the antigen-presenting cells were grown, or any suitable buffering medium such as phosphate buffered saline.

In one embodiment, the antigen-primed antigen-presenting cells of the invention could also be used for generating large numbers of $CD8^+$ or $CD4^+$ CTL, for adoptive transfer to immunosuppressed individuals who are unable to mount normal immune responses. For example, antigen-specific $CD8^+$ CTL can be adoptively transferred for therapeutic purposes in individuals afflicted with HIV infection (Koup et al., 1991, *J. Exp. Med.*, 174: 1593-1600; Carmichael et al., 1993, *J. Exp. Med.*, 177: 249-256; and Johnson et al., 1992, *J. Exp. Med.*, 175: 961-971), malaria (Hill et al., 1992, *Nature*, 360: 434-439) and malignant tumours such as melanoma (Van der Brogen et al., 1991, *Science*, 254: 1643-1647; and Young and Steinman, 1990, *J. Exp. Med.*, 171: 1315-1332).

In another embodiment, the immunomodulating composition of the invention is suitable for treatment or prophylaxis of a cancer. Cancers which could be suitably treated in accordance with the practices of this invention include cancers associated with a viral infection such as cervical cancer (e.g., papillomavirus infection) and Burkitt's lymphoma (e.g., Epstein Barr virus infection). Other virus associated cancers include, but are not restricted to, HTLV1 associated leukemia, Non Hodgkins lymphoma (EBV), anal cancer, skin cancer (HPV), hepatocellular carcinoma (HBV) and Kaposis sarcoma (HHV8).

In yet another embodiment, the immunomodulating composition is suitable for treatment or prophylaxis of a viral, bacterial or parasitic infection. Viral infections contemplated by the present invention include, but are not restricted to, infections caused by HIV, Hepatitis, Influenza, Japanese encephalitis virus, Epstein-Barr virus and respiratory syncytial virus. Bacterial infections include, but are not restricted to, those caused by *Neisseria* species, *Meningococcal* species, *Haemophilus* species *Salmonella* species, *Streptococcal* species, *Legionella* species and *Mycobacterium* species. Parasitic infections encompassed by the invention include, but are not restricted to, those caused by *Plasmodium* species, *Schistosoma* species, *Leishmania* species, *Trypanosoma* species, *Toxoplasma* species and *Giardia* species.

The effectiveness of the immunization may be assessed using any suitable technique. For example, CTL lysis assays may be employed using stimulated splenocytes or peripheral blood mononuclear cells (PBMC) on peptide coated or recombinant virus infected cells using $^{51}Cr$ labeled target cells. Such assays can be performed using for example primate, mouse or human cells (Allen et al., 2000, *J. Immunol.* 164(9): 4968-4978 also Woodberry et al., infra). Alternatively, the efficacy of the immunization may be monitored using one or more techniques including, but not limited to, HLA class I tetramer staining—of both fresh and stimulated PBMCs (see for example Allen et al., supra), proliferation assays (Allen et al., supra), ELISPOT assays and intracellular cytokine staining (Allen et al., supra), ELISA Assays—for linear B cell responses; and Western blots of cell sample expressing the synthetic polynucleotides. Particularly relevant will be the cytokine profile of T cells activated by antigen, and more particularly the production and secretion of IFNγ, IL-2, IL4, IL5, IL-10, TGFβ and TNF α.

9. Methods for Assessing Immunomodulation

An individual's capacity to respond to foreign or disease-specific antigens (e.g., viral antigens and cancer antigens) may be assessing whether those cells primed to attack such antigens are increased in number, activity, and ability to detect and destroy those antigens. Strength of immune response is measured by standard tests including: direct measurement of peripheral blood lymphocytes by means known to the art; natural killer cell cytotoxicity assays (see, e.g., Provinciali M. et al (1992, *J. Immunol. Meth.* 155: 19-24), cell proliferation assays (see, e.g., Vollenweider, I. and Groseurth, P. J. (1992, *J. Immunol. Meth.* 149: 133-135), immunoassays of immune cells and subsets (see, e.g., Loeffler, D. A., et al. (1992, *Cytom.* 13: 169-174); Rivoltini, L., et al. (1992, *Can. Immunol. Immunother.* 34: 241-251); or skin tests for cell-mediated immunity (see, e.g., Chang, A. E. et al (1993, *Cancer Res.* 53: 1043-1050).

The cytotoxic activity of T lymphocytes, and in particular the ability of cytotoxic T lymphocytes to be induced by antigen-presenting cells, may be assessed by any suitable technique known to those of skill in the art. For example, a sample comprising T lymphocytes to be assayed for cytotoxic activity is obtained and the T lymphocytes are then exposed to antigen-primed antigen-presenting cells, which have been caused to present antigen. After an appropriate period of time, which may be determined by assessing the cytotoxic activity of a control population of T lymphocytes which are known to be capable of being induced to become cytotoxic cells, the T lymphocytes to be assessed are tested for cytotoxic activity in a standard cytotoxic assay. Such assays may include, but are not limited to, the chromium release CTL assay known in the art.

The method of assessing CTL activity is particularly useful for evaluating an individual's capacity to generate a cytotoxic response against cells expressing tumour or viral antigens. Accordingly, this method is useful for evaluating an individual's ability to mount an immune response against a cancer or virus.

In order that the invention may be readily understood and put into practical effect, particular preferred embodiments will now be described by way of the following non-limiting examples.

EXAMPLES

Example 1

Mice, DNA Immunisation and Cell Lines

Specific pathogen-free female BALB/c and C57BL/6 mice aged 6 to 8 weeks were purchased from the Animal Resource Centre (Perth, Australia) and were maintained under clean conditions in a conventional mouse house.

Female BALB/c and C57 BL/6 mice, 6 to 8 weeks old, were immunised by particle bombardment with DNA-coated gold beads (2 µg DNA/dose) using the helium-powered Helios Gene Gun delivery system (Bio-Rad Laboratories, Richmond, Calif., U.S.A.). DNA (1.0 µg) was coupled to 0.5 mg of 1.0-µm-diameter gold particles, as recommended by the manufacturer. DNA-coated microcarriers were delivered into the abdominal epidermis at a helium pressure setting of 400 psi.

A human papillomavirus (HPV) 16 E7 transduced EL-4 cell line, C236, and the parent cell line (EL-4) were maintained in complete RPMI-1640 medium plus 10% foetal bovine serum (CSL, Melbourne, Australia).

Example 2

Codon Replacements in the HPV6bL1, E7 and Ubiquitin Genes

The HPV6bL1, HPV6b-E7 and the human ubiquitin gene sequences were modified to substitute preferred codons for rarely used codons, according to previously described methods[12]. A polynucleotide encoding HPV6bL1 truncated of the C terminal 33 amino acids was made as a codon-modified construct (H6L1Δ) (SEQ ID NO: 9) and also with the native codons (6L1Δ) (SEQ ID NO: 7).

An HPV6bL1-E7 fusion gene (H6L1E7.1) (SEQ ID NO: 11) was constructed by adding to H6L1Δ a codon-modified sequence corresponding to amino acids 2-50 of the HPV6b E7 protein. H6L1E7.2 (SEQ ID NO: 13) was similarly constructed by adding a polynucleotide encoding amino acids 49-98 of HPV6b E7, and H6L1-H16E7 (SEQ ID NO: 19) was constructed by adding a polynucleotide corresponding to the minimal H-2 $D^b$ CTL epitope of HPV16 (RAHYNTVTF). Construction of codon-modified BPV1 L2 (SEQ ID NO: 23), termed HBL2, has been described previously[12].

A ubiquitin-HL1-16E7 fusion construct (SEQ ID NO: 15) was produced by adding a sequence encoding a ubiquitin monomer 5' to the L1-16E7 gene construct. Codon-modified genes of the desired sequence were synthesised by Operon (Alameda, Calif., U.S.A.), and all sequences were verified by big dye terminator sequencing. Sequences for the seven novel codon-modified polynucleotide vaccine constructs used herein were deposited with GenBank under Accession Numbers AF322411-5 (SEQ ID NO: 9, 11, 13, 15, respectively) and AF323508-9 (SEQ ID NO: 17 and 19, respectively).

Example 3

Plasmid Constructions

Primers were designed to allow cloning of gene constructs into eukaryotic expression plasmids. All primers coded for one flanking EcoKL or KpnI restriction site at their N-terminus, and for 18-24 nucleotides of the corresponding gene. These were used to amplify PV gene sequences by PCR. Amplified PCR products were cut with KpnI and EcoRI restriction enzymes and, ligated to the pCDNA3 mammalian expression vector containing the simian virus 40 (SV40) ori (Invitrogen, Carlsbad, Calif., U.S.A.) to produce the corresponding expression plasmids.

Example 4

Measurement of Antibody Responses

Measurement of total VLP-specific IgG in serum was performed by capture ELISA, as previously described[37]. To measure HPV6b L1 antibody against linear epitopes, HPV6b L1 VLPs were denatured by alkaline reduction (0.2M $Na_2CO_3$ buffer, pH 10.6, 0.01 M dithiothreitol)[38] and coated directly onto ELISA plates at a concentration of 20 µg/ml. For the L2 antibody assay (see Example 11, below), ELISA plates were coated with 50 µl of purified His-tag recombinant BPVL2 protein at a concentration of 10 µg/ml in 50 mM carbonate buffer, pH. 9.6. For the E7 specific antibody assay, Cos-1 cells (see Example 6, below) were transfected with pCDNA3E7[39] for 48 hours. Cell lysates were prepared in 0.5% NP-40, 0.1 M Tris-HCl (Ph. 8.5). Sodium dodecyl sulphate-polyacrylamide gel electrophoresis (SDS-PAGE) was carried out using standard methods. Proteins were transferred to nitrocellulose membrane. Sera were applied diluted 1:100 in PBS with 5% non-fat dried milk. Secondary antibody was peroxidase-conjugated anti-mouse (Sigma, St Louis, Mo., U.S.A.), and was detected by ECL.

Example 5

Codon Modification Generates Increased Immunogenicity

To investigate the effect of codon modification on immunogenicity of a human papillomavirus 6 (HPV6) L1 capsid protein polynucleotide vaccine, plasmids were constructed to express HPV6b L1, utilising either the native nucleotide sequence (p6L1Δ) (SEQ ID NO: 7) or a sequence modified to encode the same L1 primary protein, using codons commonly found in highly expressed human genes (pH6L1Δ) (SEQ ID NO: 9). Both L1 gene constructs were truncated by 33 codon triplets at the C terminus. This removed a region encoding the L1 nuclear localisation signals[16], which allows addition of sequences encoding defined T cell epitopes from papillomavirus (PV) non-structural proteins for therapeutic effect, while preserving the ability of the L1 protein to form virus-like particles (VLPs)[17].

Plasmids were purified using a Qiagen Plasmid Mega Kit (Qiagen, Chatsworth, Calif., U.S.A.) and were dissolved in phosphate-buffered saline (PBS) at a concentration of 1 µg/µL.

Conformational antibody against HPV6b was detected after a single immunisation with pH6L1Δ (SEQ ID NO: 9), delivered intracutaneously on gold beads, and the antibody titre increased after a further immunisation (see FIG. 1a). Antibody reactive with denatured HPV6b L1 protein was also observed, at lesser titre than antibody reactive with HPV6b VLPs (see FIG. 1b). In contrast, no antibody specific for HPV6b VLPs or for denatured HPV6b L1 was found following immunisation with the non-codon-modified L1 gene p6L1Δ (SEQ ID NO: 7) (FIGS. 1a and 1b). Thus, a codon-modified L1 polynucleotide vaccine was significantly more immunogenic than the native gene, and induced antibody predominantly to conformational epitopes of the virus. Similar data with native (SEQ ID NO: 3) and codon modified (SEQ ID NO: 5) plasmids expressing a full length HPV6b L1 protein were also obtained.

Previous studies with PV L1 polynucleotide vaccines have shown that codon unmodified vaccines are relatively non-immunogenic, in keeping with the current findings. Repeated intranasal immunisation of mice with an HPV16 L1 polynucleotide vaccine induced serum IgG and vaginal IgA responses that were scarcely above background, although some T cell proliferation and cytokine release was observed in splenocytes from immunised animals exposed to particulate L1 VLP antigen[13]. Intravaginal immunisation of rabbits with HPV6b L1 DNA required cholera toxin to induce some VLP specific IgA antibody in vaginal secretions, whereas animals immunised intramuscularly with the same construct had no detectable serum L1 specific antibody by ELISA and low titre antibody by immunoblot[14]. CRPV L1 polynucleotide vaccines are, in contrast to HPV, immunogenic, whether delivered by im injection[32] or intradermally[33]. While CRPV is generally similar in codon usage to other PV genes, the CRPV L1 gene is relatively GC rich with a GC content approaching the mammalian genome consensus (Human consensus 52.5%; CRPV 47.7%; HPV6 42.5%), and several codons relatively infrequently used in mammalian genes are significantly less common in CRPV L1 than in BPV1, HPV6, or HPV16 (Table 1). Presumably, one or more of these codons are poorly translated in the cell types in which L1 expression is required for induction of antibody in vivo. Additionally, internal RNA sequences inhibitory to translation of PV L1 genes[34] might be less inhibitory in CRPV than in other PV genomes.

Example 6

Humoral Immunity in Mice Immunised with Chimeric L1-E7 Hybrid Polynucleotides

To induce immune responses that might be therapeutic as well as prophylactic for PV infection, chimeric polynucleotide vaccines were constructed by incorporating the L1 capsid gene (pH6L1Δ) (SEQ ID NO: 9) with segments of E7 (SEQ ID NO: 11 and 13), a non-structural protein of PV found abundantly in infected cells, added to the C terminus. Mice immunised with each of these chimeric codon-modified L1 polynucleotide vaccines developed high levels of virus specific antibody (see FIGS. 1c and 1d). Induction of E7 specific immunity by the L1-E7 chimeric vaccines was tested using HPV6bE7 transfected Cos-1 cells as a source of HPV6b E7 protein, immunoreactivity with a 14 kD protein, presumed to be E7, was observed in mice immunised with L1 chimeric polynucleotide vaccines which incorporated the N- or C-terminal region of HPV6bE7 (pH6L1E7.1 or pH6L1E7.2, SEQ ID NO: 11 and 13, respectively) (see FIG. 1f). As expected, no reactivity with HPV6bE7 in serum from mice immunised with pH6L1Δ (SEQ ID NO: 9), or from non-immunised mice, was seen.

Example 7

Cell-Mediated Immunity in Mice Immunised with Chimeric L1-E7 Hybrid Polynucleotides As therapeutic intervention for PV appears to require cell-mediated immune responses to PV proteins, induction of cellular immune responses by the polynucleotide vaccines was then measured. First, the induction of delayed type hypersensitivity (DTH) to the L1 capsid protein was examined. The DTH reaction was assayed by an ear-swelling test, as previously described[40], using purified HPV6b L1VLPs[11] as the challenge antigen. L1-specific DTH responses were observed to be induced by immunisation with codon-modified pH6L1Δ (SEQ ID NO: 9), and also by codon-modified L1E7 chimeric vaccines pH6L1E7.1 and pH6L1E7.2 (SEQ ID NO: 11 and 13, respectively), but not by codon-unmodified p6L1Δ (SEQ ID NO: 7) or by the pCDNA3 vector (see FIG. 2a).

Figure 2:
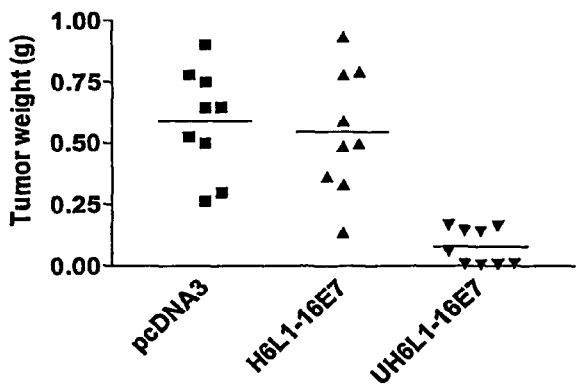
FIG. 2 is a graphical representation showing cell-mediated immunity to L1 induced by polynucleotide vaccines. Graph a shows cutaneous DTH responses to L1 measured in groups of mice immunised with codon-modified pH6L1A, or codon-modified chimeric H6L1E7.1 or 0.2, with unmodified 6L1 or p6L1Δ, or with pCDNA3 vector. Graph b illustrates HPV 16 E7 CTL epitope specific IFNγ secreting lymph node T cell precursors in C57BL/6 mice immunised with either pcDNA3, codon-modified HPV6L1-HPV16E7 (pH6L1E7) or ubiquitin-conjugated codon-modified HPV6L1-HPV16E7 DNA (pUH6L1E7). Mean of triplicates ±1 SD are shown. Graph c shows protection against the subcutaneous growth of E7 expressing TC-1 tumours in mice immunised with pcDNA3, pH6L116E7 (paired t test, P<0.01, pH6L116E7 vs pUH6L116E7), or pUH6L116E7 DNA (paired t test, P<0.01, pcDNA3 vs pUH6L116E7).
Figure 2:
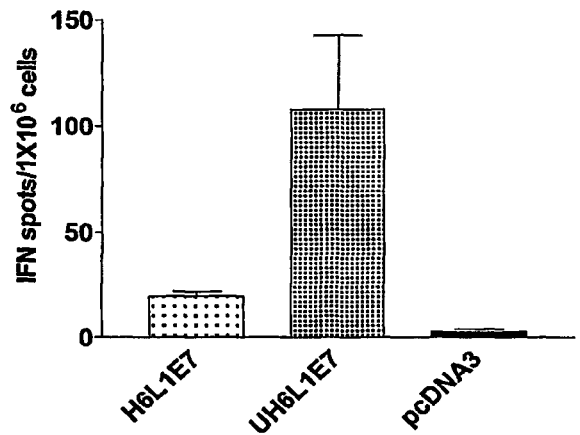
Figure 2:
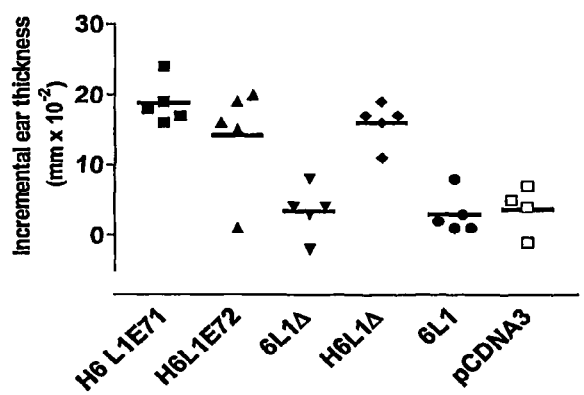

The cytotoxic T lymphocyte (CTL) response induced to a dominant H-2$^b$ restricted CTL epitope of HPV16 E7, incorporated in the codon-modified chimeric construct pH6L1-16E7 (SEQ ID NO: 19), was found to be relatively poor (see FIG. 2b).

Example 8

Ubiquitination of 6L1 Improves CTL Response

To determine whether ubiquitination of the codon-modified 6L1 gene product could improve the CTL response, a vaccine was made in which a single copy of the ubiquitin gene was inserted, in frame, 5' to the codon-modified chimeric L1-E7 gene (SEQ ID NO: 17).

Splenocytes were prepared from immunised animals and CTL activity was assessed after a 3 day in vitro re-stimulation with rIL-2 (Sigma), and peptide RAHYNTVTF, as previously described[44]. Assays were performed in triplicate, and spontaneous $^{51}$Cr release from the various targets did not exceed 15%.

A modified ELISPOT assay[41] was used to detect HPV-16 E7-specific CD8+ T cells. Filtration plates (96-well) (Millipore, Bedford, Mass., U.S.A.) were coated with 10 μg/mL rat anti-mouse IFN-γ antibody (clone R4-6A2, Pharmingen, San Diego, Calif., U.S.A.) in 50 μL PBS. After overnight incubation at 4° C., the wells were washed and blocked with culture medium containing 10% foetal bovine serum. 1×10$^6$ of fresh isolated spleen and lymph node cells were added to the well, along with 20 IU/mL IL-2. Cells were incubated at 37° C. for 24 hours either with or without 1 μg/mL HPV16 E7 specific H-2D$^b$ CTL epitope (E7, amino acid 49-57). After culture, the plate was washed and then followed by incubation with 5 μg/mL biotinylated IFN-γ antibody (clone XMG1.2, PharMingen, Franklin Lakes, N.J., U.S.A.) in 50 μL in PBS at 4° C. overnight. After washing six times, 1.25 μg/mL avidin-alkaline phosphatase (Sigma) in 50 μL PBS was added and incubated for 2 hours at room temperature. After washing, spots were developed by adding 50 μL of 5-bromo-4-chloro-3-3-indolyl phosphate/nitroblue tetrazolium solution (Boehringer Manheim, Indianapolis, Ind., U.S.A.) and incubated at room temperature for 1 hour. The spots were counted using a dissecting microscope.

The ubiquitin-containing vaccine, in contrast to the construct without ubiquitin, induced a significant E7-specific CD8 T cell response (see FIG. 2b).

Example 9

CTL Response Following Ubiquitination is Host-Protective

Mice were challenged with an E7-expressing tumour, in order to assess whether the observed improved CTL response was host protective. Mice were S.C.-challenged with 2×10$^6$ cells/mouse TC-1 tumour cell[42], in the scruff of neck, and tumour weight recorded 10 days after challenge, as previously described[43].

Figure 3:
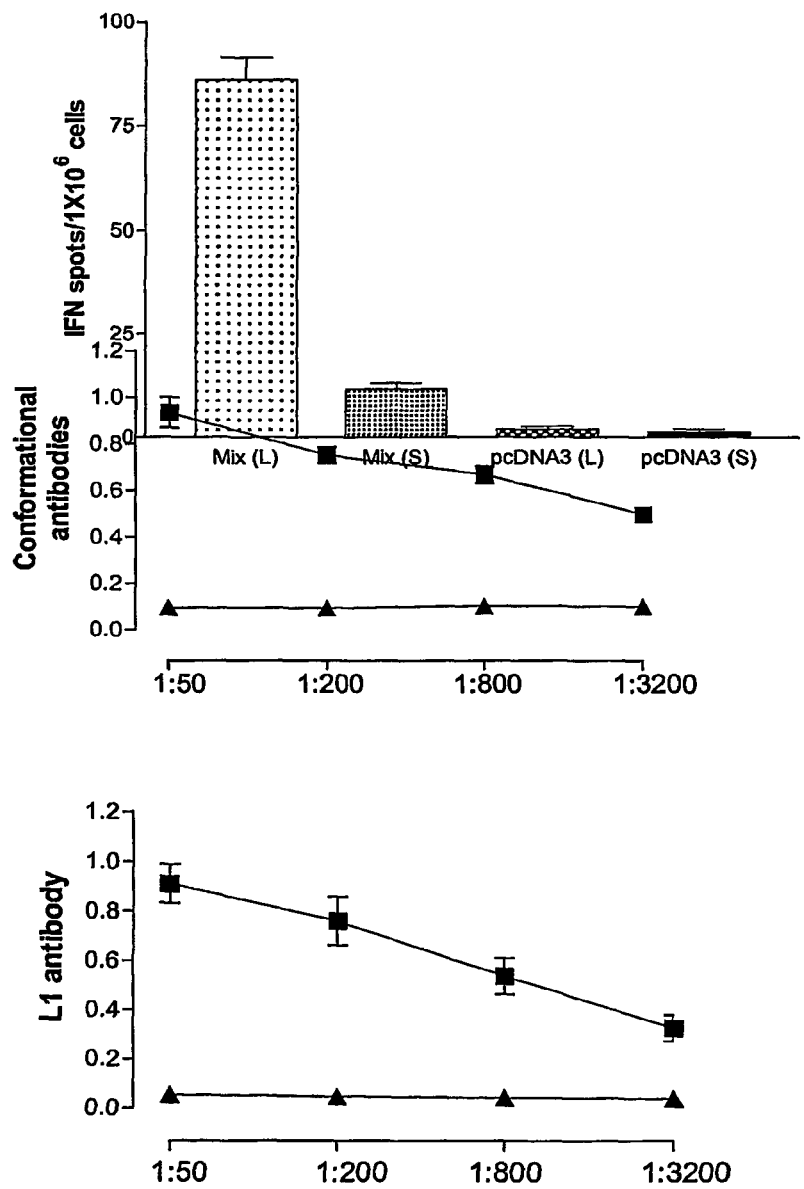
FIG. 3 is a graphical representation illustrating induction of neutralising antibody and CD8+ve T cells by a mixed polynucleotide vaccine comprising ubiquitin conjugated and non conjugated HPV6bL116E7. a. HPV 16 E7 CTL epitope specific IFNγ secreting lymph node(L) or spleen(S) T cell precursors in C57BL/6 mice immunised with a mixture of codon modified HPV6L1-HPV16E7 and Ubiquitin conjugated codon modified HPV6L1-HPV16E7 DNA (mix) or a control.

As can be seen in FIG. 2c, mice immunised with ubiquitin-conjugated H6L1-16E7 (SEQ ID NO: 17) showed significant reduction in tumour weight, compared with animals immunised with the same construct without ubiquitin. These data confirmed that the induced cellular response was, indeed, host protective. Of interest, the ubiquitin-conjugated chimeric construct induced only low levels of HPV specific antibodies (refer to FIG. 1e) when compared with the non-ubiquitin construct. A mixed polynucleotide vaccine comprising the codon modified L1-E7 with and without ubiquitin was, therefore, made to establish whether the mixture would convey the properties of both immunogens. Mice immunised with the mixture acquired both conformational and non-conformational antibody to L1 (FIGS. 3a,b) and developed IFN-γ secreting CD8$^+$ cells in lymph node and spleen (FIG. 3c), and were protected against tumour challenge (data not shown) confirming that the immune response to the mixed polynucleotide vaccine was as would be expected from the response to each of the two parts.

Example 10

HPV6bL1 Polynucleotide Vaccine Induces Neutralising Antibodies

Figure 4:
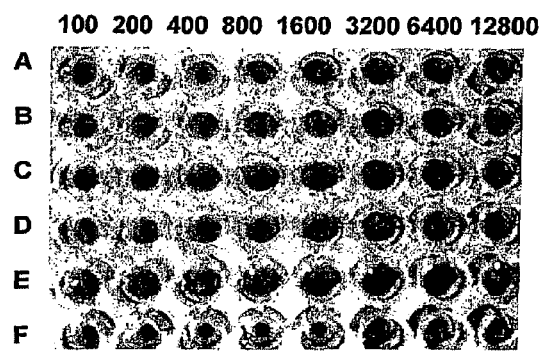
FIG. 4 is a photographic representation of a plate showing inhibition of HPV6 L1 induced agglutination of mouse erythrocytes by sera from mice immunised with codon-modified or unmodified HPV6b L1 DNA. Serial dilutions (1:100-1:12800) of sera from mice immunised with codon modified L1 genes; A: pH6L1Δ, one immunisation; B: pH6L1Δ, two immunisations; C: pH6L1E7.1; D: pH6L1E7.2, inhibited agglutination, whereas unmodified gene (E: p6L1Δ) did not induce inhibitory antibody. Rabbit anti-HPV6 L1 antibody (F) was used as a positive control.

To confirm that the various modified L1 vaccine constructs each induced PV neutralising antibody, sera were tested in a hemagglutination inhibition assay (HAI) shown to correlate with virus neutralisation[18]. The method used was as previously described[18]. Sera from mice immunised with each of the codon-modified and codon-modified chimeric constructs showed strong HAI activity (see FIG. 4), whereas no HAI activity were found in the sera from mice immunised with the unmodified L1 gene.

Example 11

Anti-BPVL2 Antibodies in Mice Immunised with an L2 Polynucleotide Vaccine

To confirm for a further PV gene that the immunogenicity of a polynucleotide vaccine could be enhanced by codon modification, mice were immunised with a codon-modified (SEQ ID NO: 23) or an unmodified (SEQ ID NO: 21) BPV1 L2 polynucleotide vaccine, or with a BPV1 L2-HPV16E7 fusion gene, also codon-modified or unmodified.

Figure 5:
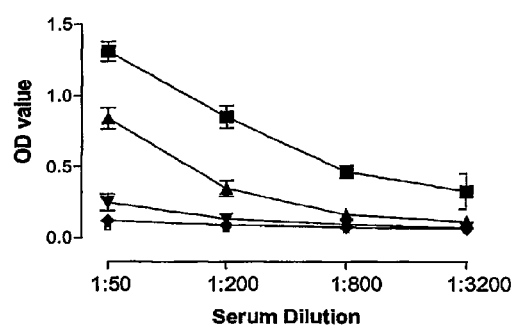
FIG. 5 is a graphical representation showing immunogenicity of codon modified and unmodified BPV1 L2. Groups of C57BL/6 mice were immunised with HBL2E7(■); HBL2 (▲); L2E7(▼); L2(◆) and L2 specific reactivity measured by ELISA. Results are shown as the mean reactivity ±1 SD.

Mice immunised with codon-modified HBL2 (SEQ ID NO: 23) and HBL2E7 developed anti-BPVL2 antibodies, whereas mice immunised with a codon-unmodified L2 (SEQ ID NO: 21) gene did not (see FIG. 5), confirming that the immunogenicity of the L2 gene was also improved by codon modification.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

Tables

TABLE 1

Codons significantly less frequently used in CRPV L1 than in PV L1 genes poorly immunogenic as DNA vaccines.

| Codon | Occurrences in L1 | | | Consensus Mammalian Usage/1000 codons[1] |
|---|---|---|---|---|
| | CRPV | HPV6 | BPV1 | |
| TTG (Leu) | 2 | 10 | 7 | 12.3 |
| TTA (Leu) | 3 | 14 | 8 | 7.2 |
| AAT (Asn) | 2 | 4 | 4 | 17.1 |
| CGT (Arg) | 1 | 4 | 2 | 4.6 |

[1]Codons encoding Leu occur as 98 of 1000, Asn as 37 of 1000, and Arg as 56 of 1000 codons when averaged across the mammalian GenBank database

BIBLIOGRAPHY

1. Wallin, K. L. et al. Type-specific persistence of human papillomavirus DNA before the development of invasive cervical cancer. N. Engl. J. Med. 341, 1633-1638 (1999).
2. Kirnbauer, R., Booy, F., Cheng, N., Lowy, D. R. & Schiller, J. T. Papillomavirus L1 major capsid protein self-assembles into virus-like particles that are highly immunogenic. Proc. Natl. Acad. Sci. USA 89, 12180-12184 (1992).
3. Zhou, L, Sun, X. Y., Stenzel, D. J. & Frazer, I. H. Expression of vaccinia recombinant HPV 16 L1 and L2 ORF proteins in epithelial cells is sufficient for assembly of HPV virion-like particles. Virology 185, 251-257 (1991),
4. Christensen, N. D., Reed, C. A., Cladel, N. M., Han, R. & Kreider, J. W. Immunization with viruslike particles induces long-term protection of rabbits against challenge with cottontail rabbit papillomavirus. J. Virol. 70, 960-965 (1996).
5. Carter, J. J. et al. Comparison of human papillomavirus types 16, 18, and 6 capsid antibody responses following incident infection. J. Infect. Dis. 181, 1911-1919 (2000).
6. Dillner, J. et al. Antibodies against linear and conformational epitopes of human papillomavirus type 16 that independently associate with incident cervical cancer. Int. J. Cancer 60, 377-382 (1995).
7. Kirnbauer, R. et al. A virus-like particle enzyme-linked immunosorbent assay detects serum antibodies in a majority of women infected with human papillomavirus type 16. JNCI 86, 494-499 (1994).
8. Frazer, L H. et al. Potential strategies utilised by papillomavirus to evade host immunity. Immunol. Rev. 168, 131-142 (1999).
9. Han, R. et al. DNA vaccination prevents and/or delays carcinoma development of papillomavirus-induced skin papillomas on rabbits. J. Virol. 74, 9712-9716 (2000).
10. Christensen, N. D., Cladel, N. M., Reed, C. A. & Han, R. Rabbit oral papillomavirus complete genome sequence and immunity following genital infection [In Process Citation]. Virology 269, 451-461 (2000).
11. Zhang, L. F. et al. HPV6b virus like particles are potent immunogens without adjuvant in man. Vaccine 18, 1051-1058 (2000).

12. Zhou J., Liu, W. J., Peng, S. W., Sun, X. Y. & Frazer, I. H. Papillomavirus capsid protein expression level depends on the match between codon usage and tRNA availability. *J. Virol.* 73, 4972-4982 (1999).
13. Dupuy, C, Buzoni-Gatel, D., Touze, A., Bout, D. & Coursaget, P. Nasal immunization of mice with human papillomavirus type 16 (HPV-16) virus-like particles or with the HPV-16 L1 gene elicits specific cytotoxic T lymphocytes in vaginal draining lymph nodes. *J. Virol.* 73, 9063-9071 (1999).
14. Schreckenberger. C. et al. Induction of an HPV 6bL1-specific mucosal IgA response by DNA immunization. *Vaccine* 19, 227-233 (2000).
15. Hines, J. F., Ghim, S. J. & Jenson, A. B. Prospects for human papillomavirus vaccine development: emerging HPV vaccines. *Curr. Opin. Infect. Dis.* 11, 57-61 (1998).
16. Zhou, J. et al. Identification of the nuclear localization signal of human papillomavirus type 16 L1 protein. *Virology* 185, 625-632 (1991).
17. Müller, M. et al. Chimeric papillomavirus-like particles. *Virology* 234, 93-111 (1997).
18. Roden, R. B. S. et al. Papillomavirus L1 capsids agglutinate mouse erythrocytes through a proteinaceous receptor. *J. Virol.* 69, 5147-5151 (1995).
19. Zur Megede, J. et al. Increased expression and immunogenicity of sequence-modified human immunodeficiency virus type 1 gag gene. *J. Virol.* 74, 2628-2635 (2000).
20. Nagata, T., Uchijima, M., Yoshida, A., Kawashima, M. & Koide, Y. Codon optimization effect on translational efficiency of DNA vaccine in mammalian cells: analysis of plasmid DNA encoding a CTL epitope derived from microorganisms. *Biochem. Biophys. Res. Commun.* 261, 445-451 (1999).
21. Andre, S. et al. Increased immune response elicited by DNA vaccination with a synthetic gp120 sequence with optimized codon usage. *J. Virol.* 72, 1497-1503 (1998).
22. Haas, J., Park, E. C. & Seed, B. Codon usage limitation in the expression of HTV-1 envelope glycoprotein. *Curr. Biol.* 6, 315-324 (1996).
23. Barry, M. A. & Johnston, S. A. Biological features of genetic immunization. *Vaccine* 15, 788-791 (1997).
24. Donnelly, J. J. et al. Protection against papillomavirus with a polynucleotide vaccine. *J. Infect. Dis.* 173, 314-320 (1996).
25. Sundaram, P., Xiao, W. & Brandsma, J. L. Particle-mediated delivery of recombinant expression vectors to rabbit skin induces high-titered polyclonal antisera (and circumvents purification of a protein immunogen). *Nucleic Acids Res.* 24, 1375-1377 (1996).
26. Schwartz, S. Cis-acting negative RNA elements on papillomavirus late mRNAs. *Semin. Virol.* 8, 291-300 (1998).
27. Tindle, R. W. Human papillomavirus vaccines for cervical cancer. *Curr. Opin. Immunol.* 8, 643-650 (1996).
28. Marais, D., Passmore, J. A., Maclean, J., Rose, R. & Williamson, A. L. A recombinant human papillomavirus (HPV) type 16 L1-vaccinia virus murine challenge model demonstrates cell-mediated immunity against HPV virus-like particles. *J. Gen. Virol.* 80, 2471-2475 (1999).
29. De Bruijn, M. L. H. et al. L1-specific protection from tumor challenge elicited by HPV16 virus-like particles. *Virology* 250, 371-376 (1998).
30. Michalek, M. T., Grant, E. P., Gramm, C., Goldberg, A. L. & Rock, K. L. A role for the ubiquitin-dependent proteolytic pathway in MHC class I-restricted antigen presentation. *Nature* 363, 552-554 (1993).
31. Xiang, R. et al. An autologous oral DNA vaccine protects against murine melanoma. *Proc. Natl. Acad. Sci. U. S. A* 97, 5492-5497 (2000).
32. Tobery, T. W. & Siliciano, R. F. Targeting of HIV-1 antigens for rapid intracellular degradation enhances cytotoxic T lymphocyte (CTL) recognition and the induction of de novo CTL responses in vivo after immunization. *J. Exp. Med.* 185, 909-920 (1997).
33. Wu, Y. Q. & Kipps, T. J. Deoxyribonucleic acid vaccines encoding antigens with rapid proteasome-dependent degradation are highly efficient inducers of cytolytic T lymphocytes. *J. Immunol.* 159, 6037-6043 (1997).
34. Tuting, T., Storkus, W. J. & Falo, L. D., Jr. DNA immunization targeting the skin: molecular control of adaptive immunity. *J. Invest Dermatol.* 111, 183-188 (1998).
35. Fu, T. M. et al. Induction of MHC class I-restricted CTL response by DNA immunization with ubiquitin-influenza virus nucleoprotein fusion antigens. *Vaccine* 16, 1711-1717 (1998).
36. Tindle, R. W. et al. A vaccine conjugate of 'ISCAR' immunocarrier and peptide epitopes of the E7 cervical cancer-associated protein of human papillomavirus type 16 elicits specific Th1- and Th2-type responses in immunized mice in the absence of oil-based adjuvants. *Clin. Exp. Immunol* 101, 265-271 (1995).
37. Peng, S. W., Frazer, I. H., Fernando, G. J. & Zhou J. Papillomavirus virus-like particles can deliver defined CTL epitopes to the MHC class I pathway. *Virology* 240, 147-157 (1998).
38. Favre, M., Breitburd, F., Croissant, O. & Orth, G. Structural polypeptides of rabbit, bovine, and human papillomaviruses. *J. Virol.* 15, 1239-1247 (1975).
39. Barnard, P. & McMillan, N. A. J. The human papillomavirus E7 oncoprotein abrogates signaling mediated by interferon-α. *Virology* 259, 305-313 (1999).
40. De Moerloose, P. A., Frazer, I. H., Sewell, W. A., Collins, E. J. & Mackay, I. R. Cell-mediated immunity to hepatitis B virus antigens in mice: correlation of in vivo and in vitro assays. *Clin. Exp. Immunol.* 64, 285-294 (1986).
41. Miyahira, Y. et al. Quantification of antigen specific $CD8^+$ T cells using an ELISPOT assay. *Journal of Immunological Methods* 181, 45-54 (1995).
42. Lin, K. Y. et al. Treatment of established tumors with a novel vaccine that enhances major histocompatibility class II presentation of tumor antigen. *Cancer Res.* 56, 21-26 (1996).
43. Fernando, G. J. P., Stewart, T. J., Tindle, R. W. & Frazer, I. H. Th2-type $CD4^+$ cells neither enhance nor suppress antitumor CTL activity in a mouse tumor model. *J. Immunol.* 161, 2421-2427 (1998).
44. Frazer, I. H. et al. Split tolerance to a viral antigen expressed in thymic epithelium and keratinocytes. *Eur. J. Immunol.* 28, 2791-2800 (1998).

The invention claimed is:

1. A method of eliciting a humoral and a cellular immune response against a target antigen, comprising contacting at least one recipient cell with a composition comprising a first antigen corresponding to the target antigen, and a second antigen, corresponding to the target antigen and comprising an intracellular degradation signal that is absent in the first antigen, wherein the presence of the intracellular degradation signal increases the rate of intracellular proteolytic degradation of the second antigen relative to the first antigen, wherein the intracellular degradation signal is a ubiquitin, wherein the first and second antigens are physically separated from each other, wherein the first antigen elicits a humoral immune response to the target antigen and wherein the second antigen elicits a cellular immune response to the target antigen, whereby said first antigen and said second antigen are expressed together in the same recipient cell or expressed separately in different recipient cells.

2. The method of claim 1, wherein the recipient cell(s) is selected from a dendritic cell, a macrophage or a B cell.

3. A method of eliciting a humoral and a cellular immune response against a target antigen, comprising contacting at least one recipient cell with at least one nucleic acid composition comprising a first polynucleotide encoding a first antigen corresponding to the target antigen, and a second polynucleotide encoding a second antigen, corresponding to the target antigen and comprising an intracellular degradation signal that is absent in the first antigen, wherein the presence of the intracellular degradation signal increases the rate of intracellular proteolytic degradation of the second antigen relative to the first antigen, wherein the intracellular degradation signal is a ubiquitin, wherein the first and second antigens are physically separated from each other, wherein the first antigen elicits a humoral immune response to the target antigen and wherein the second antigen elicits a cellular immune response to the target antigen, wherein said first polynucleotide and said second polynucleotide are expressed from different constructs, whereby said first antigen and said second antigen are expressed together in the same recipient cell or expressed separately in different recipient cells.

4. The method of claim 3, wherein the nucleic acid composition is produced by optimising the codon composition of a parent polynucleotide encoding an antigen selected from the group consisting of the first antigen and the second antigen to construct a codon optimised polynucleotide whereby expression of the antigen from the codon optimised polynucleotide in said at least one recipient cell is increased, enhanced or otherwise elevated relative to that from said parent polynucleotide.

5. The method of claim 3, wherein said codon composition is optimised by: selecting a first codon of the parent polynucleotide for replacement with a synonymous codon, wherein the first codon is selected on the basis that it has a higher translational efficiency than said synonymous codon in said at least one recipient cell, and replacing said first codon with said synonymous codon to construct said codon optimised polynucleotide.

6. The method of claim 3, wherein said codon composition is optimised so that the antigen is expressible at a higher level in said recipient cell than in another cell.

7. The method of claim 3, wherein said codon composition is optimised by: selecting a first codon of the parent polynucleotide for replacement with a synonymous codon which has a higher translational efficiency in said recipient cell than in another cell; and replacing said first codon with said synonymous codon to form said codon optimised polynucleotide.

8. The method of claim 3, wherein the recipient cell(s) is selected from a dendritic cell, a macrophage or a B cell.

9. A method for modulating an immune response, comprising administering to a patient in need of such treatment a composition comprising (a) a first antigen corresponding to a target antigen, together with a second antigen corresponding to the target antigen and comprising an intracellular degradation signal that is absent from the first antigen, wherein the presence of the intracellular degradation signal increases the rate of intracellular proteolytic degradation of the second antigen relative to the first antigen, wherein the intracellular degradation signal is a ubiquitin, wherein the first and second antigens are physically separated from each other, wherein the first antigen elicits a humoral immune response to the target antigen and wherein the second antigen elicits a cellular immune response to the target antigen; (b) a first polynucleotide encoding a first antigen corresponding to a target antigen, a second polynucleotide encoding a second antigen, corresponding to the target antigen and comprising an intracellular degradation signal that is absent in the first antigen, wherein the presence of the intracellular degradation signal increases the rate of intracellular proteolytic degradation of the second antigen relative to the first antigen, wherein the intracellular degradation signal is a ubiquitin, wherein the first and second antigens are physically separated from each other, wherein the first antigen elicits a humoral immune response to the target antigen and wherein the second antigen elicits a cellular immune response to the target antigen, wherein said first polynucleotide and said second polynucleotide are expressed from different constructs; or (c) antigen-presenting cells which have been contacted with a first antigen corresponding to a target antigen or with a polynucleotide from which the first antigen is expressible, and with a second antigen corresponding to the target antigen and comprising an intracellular degradation signal that is absent in the first antigen, wherein the first and second antigens are physically separated from each other, wherein the presence of the intracellular degradation signal increases the rate of intracellular proteolytic degradation of the second antigen relative to the first antigen wherein the intracellular degradation signal is a ubiquitin or with a polynucleotide from which the second antigen is expressible, for a time and under conditions sufficient to express a processed form of said first antigen, and a processed form of said second antigen, for presentation to, and modulation of, T cells.

10. A method for treatment and/or prophylaxis of a disease or condition, comprising administering to a patient in need of such treatment an effective amount of a composition comprising (a) a first antigen corresponding to a target antigen, together with a second antigen corresponding to the target antigen and comprising an intracellular degradation signal that is absent in the first antigen, wherein the presence of the intracellular degradation signal increases the rate of intracellular proteolytic degradation of the second antigen relative to the first antigen wherein the intracellular degradation signal is a ubiquitin, wherein the first and second antigens are physically separated from each other; (b) a first polynucleotide encoding a first antigen corresponding to a target antigen, a second polynucleotide encoding a second antigen, corresponding to the target antigen and comprising an intracellular degradation signal that is absent in the first antigen, wherein the presence of the intracellular degradation signal increases the rate of intracellular proteolytic degradation of the second antigen relative to the first antigen, wherein the intracellular degradation signal is a ubiquitin wherein the first and second antigens are physically separated from each other, wherein the first antigen elicits a humoral immune response to the target antigen and wherein the second antigen elicits a cellular immune response to the target antigen, wherein said first polynucleotide and said second polynucleotide are expressed from different constructs; or (c) antigen-presenting cells which have been contacted with a first antigen corresponding to a target antigen or with a polynucleotide from which the first antigen is expressible, and with a second antigen corresponding to the target antigen and comprising an intracellular degradation signal that is absent in the first antigen, wherein the presence of the intracellular degradation signal increases the rate of intracellular proteolytic degradation of the second antigen relative to the first antigen, wherein the intracellular degradation signal is a ubiquitin, wherein the first and second antigens are physically separated from each other, wherein the first antigen elicits a humoral immune response to the target antigen and wherein the second antigen elicits a cellular immune response to the target antigen, or with a polynucleotide from which the second antigen is expressible, for a time and under conditions sufficient to express a processed form of said first antigen, and a processed form of said second antigen, for presentation to, and modulation of, T cells.

11. A method for eliciting a humoral and a cellular immune response against a target antigen, comprising co-administering to a patient:
a first antigen corresponding to the target antigen, or a polynucleotide from which the first antigen is expressible; and
a second antigen corresponding to the target antigen and comprising an intracellular degradation signal that is absent in the first antigen, wherein the presence of the intracellular degradation signal increases the rate of intracellular proteolytic degradation of the second antigen relative to the first antigen, wherein the intracellular degradation signal is a ubiquitin, wherein the first and second antigens are physically separated from each other, wherein the first antigen elicits a humoral immune response to the target antigen and wherein the second antigen elicits a cellular immune response to the target antigen, or a polynucleotide from which the second antigen is expressible.

12. A method for eliciting a humoral and a cellular immune response against a target antigen, comprising co-administering to a patient: a polynucleotide from which a first antigen, corresponding to the target antigen, is expressible; and a polynucleotide from which a second antigen, corresponding to the target antigen, is expressible, wherein the second antigen comprises an intracellular degradation signal that is absent in the first antigen, wherein the presence of the intracellular degradation signal increases the rate of intracellular proteolytic degradation of the second antigen relative to the first antigen, wherein the intracellular degradation signal is a ubiquitin, wherein the first and second antigens are physically separated from each other, wherein the first antigen elicits a humoral immune response to the target antigen and wherein the second antigen elicits a cellular immune response to the target antigen.

13. A method for eliciting a humoral and a cellular immune response against a target antigen, comprising co-administering to a patient:
a first antigen corresponding to the target antigen; and
a second antigen, corresponding to the target antigen and comprising an intracellular degradation signal that is absent from the first antigen, wherein the presence of the intracellular degradation signal increases the rate of intracellular proteolytic degradation of the second antigen relative to the first antigen, wherein the intracellular degradation signal is a ubiquitin, wherein the first and second antigens are physically separated from each other, wherein the first antigen elicits a humoral immune response to the target antigen and wherein the second antigen elicits a cellular immune response to the target antigen.

14. A method for eliciting a humoral and a cellular immune response against a target antigen, comprising co-administering to a patient:
antigen-presenting cells which have been contacted with a first antigen corresponding to the target antigen, or with a polynucleotide from which the first antigen is expressible, for a time and under conditions sufficient to express a processed form of said first antigen for presentation to, and modulation of, T cells; and
antigen-presenting cells which have been contacted with a second antigen, corresponding to the target antigen and comprising an intracellular degradation signal that is absent in the first antigen, wherein the presence of the intracellular degradation signal increases the rate of intracellular proteolytic degradation of the second antigen relative to the first antigen, wherein the intracellular degradation signal is a ubiquitin, wherein the first and second antigens are physically separated from each other, wherein the first antigen elicits a humoral immune response to the target antigen and wherein the second antigen elicits a cellular immune response to the target antigen, or with a polynucleotide from which the second antigen is expressible, for a time and under conditions sufficient to express a processed form of said second antigen for presentation to, and modulation of, T cells,
wherein the antigen-presenting cells which have been contacted with the first antigen and the antigen-presenting cells which have been contacted with the second antigen may be the same or different.

15. A method for modulating an immune response, comprising administering to a patient in need of such treatment at least one composition comprising a first polynucleotide encoding a first antigen corresponding to a target antigen, a second polynucleotide encoding a second antigen, corresponding to the target antigen and comprising an intracellular degradation signal that is absent in the first antigen, wherein the presence of the intracellular degradation signal increases the rate of intracellular proteolytic degradation of the second antigen relative to the first antigen, wherein the intracellular degradation signal is a ubiquitin, wherein the first and second antigens are physically separated from each other, wherein the first antigen elicits a humoral immune response to the target antigen and wherein the second antigen elicits a cellular immune response to the target antigen, wherein said first polynucleotide and said second polynucleotide are expressed from different regulatory constructs.

16. A method for modulating an immune response, comprising administering to a patient in need of such treatment the composition comprising antigen-presenting cells which have been contacted with a first antigen corresponding to the target antigen or with a polynucleotide from which the first antigen is expressible, and with a second antigen corresponding to the target antigen and comprising an intracellular degradation signal that is absent in the first antigen, wherein the presence of the intracellular degradation signal increases the rate of intracellular proteolytic degradation of the second antigen relative to the first antigen, wherein the intracellular degradation signal is a ubiquitin, wherein the first and second antigens are physically separated from each other, wherein the first antigen elicits a humoral immune response to the target antigen and wherein the second antigen elicits a cellular immune response to the target antigen, or with a polynucleotide from which the second antigen is expressible, for a time and under conditions sufficient to express a processed form of said first antigen, and a processed form of said second antigen, for presentation to, and modulation of, T cells.

17. A method for treatment and/or prophylaxis of a disease or condition, comprising administering to a patient in need of such treatment an effective amount of at least one composition comprising a first polynucleotide encoding a first antigen corresponding to a target antigen, a second polynucleotide encoding a second antigen, corresponding to the target antigen and comprising an intracellular degradation signal that is absent in the first antigen, wherein the presence of the intracellular degradation signal increases the rate of intracellular proteolytic degradation of the second antigen relative to the first antigen, wherein the intracellular degradation signal is a ubiquitin, wherein the first and second antigens are physically separated from each other, wherein the first antigen elicits a humoral immune response to the target antigen and wherein the second antigen elicits a cellular immune response to the target antigen, wherein said first polynucleotide and said second polynucleotide are expressed from different constructs.

18. A method for treatment and/or prophylaxis of a disease or condition, comprising administering to a patient in need of such treatment an effective amount of the composition comprising antigen-presenting cells which have been contacted with a first antigen corresponding to the target antigen or with a polynucleotide from which the first antigen is expressible, and with a second antigen corresponding to the target antigen and comprising an intracellular degradation signal that is absent in the first antigen, wherein the presence of the intracellular degradation signal increases the rate of intracellular proteolytic degradation of the second antigen relative to the first antigen, wherein the intracellular degradation signal is a ubiquitin, wherein the first and second antigens are physically separated from each other, wherein the first antigen elicits a humoral immune response to the target antigen and wherein the second antigen elicits a cellular immune response to the target antigen, or with a polynucleotide from which the second antigen is expressible, for a time and under conditions sufficient to express a processed form of said first antigen, and a processed form of said second antigen, for presentation to, and modulation of, T cells.

\* \* \* \* \*

SEQUENCE LISTING

<160> NUMBER OF SEQ ID NOS: 29

<210> SEQ ID NO 1
<211> LENGTH: 231
<212> TYPE: DNA
<213> ORGANISM: Homo sapiens
<220> FEATURE:
<221> NAME/KEY: CDS
<222> LOCATION: (1)..(231)

<400> SEQUENCE: 1

```
atg cag atc ttc gtg aag act ctg act ggt aag acc atc acc ctc gag      48
Met Gln Ile Phe Val Lys Thr Leu Thr Gly Lys Thr Ile Thr Leu Glu
1               5                   10                  15 gtg gag ccc agt gac acc atc gag aat gtc aag gca aag atc caa gat      96
Val Glu Pro Ser Asp Thr Ile Glu Asn Val Lys Ala Lys Ile Gln Asp
                20                  25                  30 aag gaa ggc att cct cct gat cag cag agg ttg atc ttt gcc gga aaa     144
Lys Glu Gly Ile Pro Pro Asp Gln Gln Arg Leu Ile Phe Ala Gly Lys
            35                  40                  45 cag ctg gaa gat ggt cgt acc ctg tct gac tac aac atc cag aaa gag     192
Gln Leu Glu Asp Gly Arg Thr Leu Ser Asp Tyr Asn Ile Gln Lys Glu
        50                  55                  60 tcc acc ttg cac ctg gta ctc cgt ctc aga ggt ggg tga                 231
Ser Thr Leu His Leu Val Leu Arg Leu Arg Gly Gly
65                  70                  75
```

<210> SEQ ID NO 2
<211> LENGTH: 76
<212> TYPE: PRT
<213> ORGANISM: Homo sapiens

<400> SEQUENCE: 2

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Phe Ala Gly Lys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Gly Gly
65                  70                  75
```

<210> SEQ ID NO 3
<211> LENGTH: 1503
<212> TYPE: DNA
<213> ORGANISM: Human papillomavirus type 6b
<220> FEATURE:
<221> NAME/KEY: CDS
<222> LOCATION: (1)..(1503)

<400> SEQUENCE: 3

```
atg tgg cgg cct agc gac agc aca gta tat gtg cct cct cct aac cct      48
Met Trp Arg Pro Ser Asp Ser Thr Val Tyr Val Pro Pro Pro Asn Pro
1               5                   10                  15 gta tcc aaa gtt gtt gcc acg gat gct tat gtt act cgc acc aac ata      96
Val Ser Lys Val Val Ala Thr Asp Ala Tyr Val Thr Arg Thr Asn Ile
                20                  25                  30 ttt tat cat gcc agc agt tct aga ctt ctt gca gtg gga cat cct tat     144
Phe Tyr His Ala Ser Ser Ser Arg Leu Leu Ala Val Gly His Pro Tyr
            35                  40                  45
```

| | | |
|---|---|---|
| ttt tcc ata aaa cgg gct aac aaa act gtt gtg cca aag gtg tca gga<br>Phe Ser Ile Lys Arg Ala Asn Lys Thr Val Val Pro Lys Val Ser Gly<br>50 55 60 | 192 | |
| tat caa tac agg gta ttt aag gtg gtg tta cca gat cct aac aaa ttt<br>Tyr Gln Tyr Arg Val Phe Lys Val Val Leu Pro Asp Pro Asn Lys Phe<br>65 70 75 80 | 240 | |
| gca ttg cct gac tcg tct ctt ttc gat ccc aca aca caa cgt tta gta<br>Ala Leu Pro Asp Ser Ser Leu Phe Asp Pro Thr Thr Gln Arg Leu Val<br>85 90 95 | 288 | |
| tgg gca tgc aca ggc cta gag gtg ggc agg gga cag cca tta ggt gtg<br>Trp Ala Cys Thr Gly Leu Glu Val Gly Arg Gly Gln Pro Leu Gly Val<br>100 105 110 | 336 | |
| ggt gta agt gga cat cct ttc cta aat aaa tat gat gat gtt gaa aat<br>Gly Val Ser Gly His Pro Phe Leu Asn Lys Tyr Asp Asp Val Glu Asn<br>115 120 125 | 384 | |
| tca ggg agt ggt ggt aac cct gga cag gat aac agg gtt aat gta ggt<br>Ser Gly Ser Gly Gly Asn Pro Gly Gln Asp Asn Arg Val Asn Val Gly<br>130 135 140 | 432 | |
| atg gat tat aaa caa aca caa tta tgc atg gtt gga tgt gcc ccc cct<br>Met Asp Tyr Lys Gln Thr Gln Leu Cys Met Val Gly Cys Ala Pro Pro<br>145 150 155 160 | 480 | |
| ttg ggc gag cat tgg ggt aaa ggt aaa cag tgt act aat aca cct gta<br>Leu Gly Glu His Trp Gly Lys Gly Lys Gln Cys Thr Asn Thr Pro Val<br>165 170 175 | 528 | |
| cag gct ggt gac tgc ccg ccc tta gaa ctt att acc agt gtt ata cag<br>Gln Ala Gly Asp Cys Pro Pro Leu Glu Leu Ile Thr Ser Val Ile Gln<br>180 185 190 | 576 | |
| gat ggc gat atg gtt gac aca ggc ttt ggt gct atg aat ttt gct gat<br>Asp Gly Asp Met Val Asp Thr Gly Phe Gly Ala Met Asn Phe Ala Asp<br>195 200 205 | 624 | |
| ttg cag acc aat aaa tca gat gtt cct att gac ata tgt ggc act aca<br>Leu Gln Thr Asn Lys Ser Asp Val Pro Ile Asp Ile Cys Gly Thr Thr<br>210 215 220 | 672 | |
| tgt aaa tat cca gat tat tta caa atg gct gca gac cca tat ggt gat<br>Cys Lys Tyr Pro Asp Tyr Leu Gln Met Ala Ala Asp Pro Tyr Gly Asp<br>225 230 235 240 | 720 | |
| aga tta ttt ttt ttt cta cgg aag gaa caa atg ttt gcc aga cat ttt<br>Arg Leu Phe Phe Phe Leu Arg Lys Glu Gln Met Phe Ala Arg His Phe<br>245 250 255 | 768 | |
| ttt aac agg gct ggc gag gtg ggg gaa cct gtg cct gat aca ctt ata<br>Phe Asn Arg Ala Gly Glu Val Gly Glu Pro Val Pro Asp Thr Leu Ile<br>260 265 270 | 816 | |
| att aag ggt agt gga aat cgc acg tct gta ggg agt agt ata tat gtt<br>Ile Lys Gly Ser Gly Asn Arg Thr Ser Val Gly Ser Ser Ile Tyr Val<br>275 280 285 | 864 | |
| aac acc ccg agc ggc tct ttg gtg tcc tct gag gca caa ttg ttt aat<br>Asn Thr Pro Ser Gly Ser Leu Val Ser Ser Glu Ala Gln Leu Phe Asn<br>290 295 300 | 912 | |
| aag cca tat tgg cta caa aaa gcc cag gga cat aac aat ggt att tgt<br>Lys Pro Tyr Trp Leu Gln Lys Ala Gln Gly His Asn Asn Gly Ile Cys<br>305 310 315 320 | 960 | |
| tgg ggt aat caa ctg ttt gtt act gtg gta gat acc aca cgc agt acc<br>Trp Gly Asn Gln Leu Phe Val Thr Val Val Asp Thr Thr Arg Ser Thr<br>325 330 335 | 1008 | |
| aac atg aca tta tgt gca tcc gta act aca tct tcc aca tac acc aat<br>Asn Met Thr Leu Cys Ala Ser Val Thr Thr Ser Ser Thr Tyr Thr Asn<br>340 345 350 | 1056 | |
| tct gat tat aaa gag tac atg cgt cat gtg gaa gag tat gat tta caa<br>Ser Asp Tyr Lys Glu Tyr Met Arg His Val Glu Glu Tyr Asp Leu Gln<br>355 360 365 | 1104 | |

-continued

```
ttt att ttt caa tta tgt agc att aca ttg tct gct gaa gta atg gcc    1152
Phe Ile Phe Gln Leu Cys Ser Ile Thr Leu Ser Ala Glu Val Met Ala
    370                 375                 380 tat att cac aca atg aat ccc tct gtt ttg gaa gac tgg aac ttt ggg    1200
Tyr Ile His Thr Met Asn Pro Ser Val Leu Glu Asp Trp Asn Phe Gly
385                 390                 395                 400 tta tcg cct ccc cca aat ggt aca tta gaa gat acc tat agg tat gtg    1248
Leu Ser Pro Pro Pro Asn Gly Thr Leu Glu Asp Thr Tyr Arg Tyr Val
                405                 410                 415 cag tca cag gcc att acc tgt caa aag ccc act cct gaa aag gaa aag    1296
Gln Ser Gln Ala Ile Thr Cys Gln Lys Pro Thr Pro Glu Lys Glu Lys
            420                 425                 430 cca gat ccc tat aag aac ctt agt ttt tgg gag gtt aat tta aaa gaa    1344
Pro Asp Pro Tyr Lys Asn Leu Ser Phe Trp Glu Val Asn Leu Lys Glu
        435                 440                 445 aag ttt tct agt gaa ttg gat cag tat cct ttg gga cgc aag ttt ttg    1392
Lys Phe Ser Ser Glu Leu Asp Gln Tyr Pro Leu Gly Arg Lys Phe Leu
    450                 455                 460 tta caa agt gga tat agg gga cgg tcc tct att cgt aca ggt gtt aag    1440
Leu Gln Ser Gly Tyr Arg Gly Arg Ser Ser Ile Arg Thr Gly Val Lys
465                 470                 475                 480 cgc cct gct gtt tcc aaa gcc tct gct gcc cct aaa cgt aag cgc gcc    1488
Arg Pro Ala Val Ser Lys Ala Ser Ala Ala Pro Lys Arg Lys Arg Ala
                485                 490                 495 aaa act aaa agg taa                                                1503
Lys Thr Lys Arg
            500

<210> SEQ ID NO 4
<211> LENGTH: 500
<212> TYPE: PRT
<213> ORGANISM: Human papillomavirus type 6b

<400> SEQUENCE: 4

Met Trp Arg Pro Ser Asp Ser Thr Val Tyr Val Pro Pro Pro Asn Pro
1               5                   10                  15

Val Ser Lys Val Val Ala Thr Asp Ala Tyr Val Thr Arg Thr Asn Ile
            20                  25                  30

Phe Tyr His Ala Ser Ser Ser Arg Leu Leu Ala Val Gly His Pro Tyr
        35                  40                  45

Phe Ser Ile Lys Arg Ala Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Phe Leu Asn Lys Tyr Asp Asp Val Glu Asn
        115                 120                 125

Ser Gly Ser Gly Gly Asn Pro Gly Gln Asp Asn Arg Val Asn Val Gly
    130                 135                 140

Met Asp Tyr Lys Gln Thr Gln Leu Cys Met Val Gly Cys Ala Pro Pro
145                 150                 155                 160

Leu Gly Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
```

```
                180             185             190
Asp Gly Asp Met Val Asp Thr Gly Phe Gly Ala Met Asn Phe Ala Asp
            195                 200             205
Leu Gln Thr Asn Lys Ser Asp Val Pro Ile Asp Ile Cys Gly Thr Thr
        210                 215                 220
Cys Lys Tyr Pro Asp Tyr Leu Gln Met Ala Ala Asp Pro Tyr Gly Asp
225                 230                 235                 240
Arg Leu Phe Phe Phe Leu Arg Lys Glu Gln Met Phe Ala Arg His Phe
                245                 250                 255
Phe Asn Arg Ala Gly Glu Val Gly Glu Pro Val Pro Asp Thr Leu Ile
            260                 265                 270
Ile Lys Gly Ser Gly Asn Arg Thr Ser Val Gly Ser Ser Ile Tyr Val
        275                 280                 285
Asn Thr Pro Ser Gly Ser Leu Val Ser Ser Glu Ala Gln Leu Phe Asn
    290                 295                 300
Lys Pro Tyr Trp Leu Gln Lys Ala Gln Gly His Asn Asn Gly Ile Cys
305                 310                 315                 320
Trp Gly Asn Gln Leu Phe Val Thr Val Val Asp Thr Thr Arg Ser Thr
                325                 330                 335
Asn Met Thr Leu Cys Ala Ser Val Thr Thr Ser Ser Thr Tyr Thr Asn
            340                 345                 350
Ser Asp Tyr Lys Glu Tyr Met Arg His Val Glu Glu Tyr Asp Leu Gln
        355                 360                 365
Phe Ile Phe Gln Leu Cys Ser Ile Thr Leu Ser Ala Glu Val Met Ala
    370                 375                 380
Tyr Ile His Thr Met Asn Pro Ser Val Leu Glu Asp Trp Asn Phe Gly
385                 390                 395                 400
Leu Ser Pro Pro Pro Asn Gly Thr Leu Glu Asp Thr Tyr Arg Tyr Val
                405                 410                 415
Gln Ser Gln Ala Ile Thr Cys Gln Lys Pro Thr Pro Glu Lys Glu Lys
            420                 425                 430
Pro Asp Pro Tyr Lys Asn Leu Ser Phe Trp Glu Val Asn Leu Lys Glu
        435                 440                 445
Lys Phe Ser Ser Glu Leu Asp Gln Tyr Pro Leu Gly Arg Lys Phe Leu
    450                 455                 460
Leu Gln Ser Gly Tyr Arg Gly Arg Ser Ser Ile Arg Thr Gly Val Lys
465                 470                 475                 480
Arg Pro Ala Val Ser Lys Ala Ser Ala Ala Pro Lys Arg Lys Arg Ala
                485                 490                 495
Lys Thr Lys Arg
            500

<210> SEQ ID NO 5
<211> LENGTH: 1503
<212> TYPE: DNA
<213> ORGANISM: Artificial Sequence
<220> FEATURE:
<223> OTHER INFORMATION: Synthetic HPV type 6b construct humanised
<220> FEATURE:
<221> NAME/KEY: CDS
<222> LOCATION: (1)..(1503)

<400> SEQUENCE: 5 atg tgg cgc ccc agc gac agc acc gtg tac gtg ccc ccc aac ccc       48
Met Trp Arg Pro Ser Asp Ser Thr Val Tyr Val Pro Pro Asn Pro
1               5                   10                  15
```

```
gtg tcc aag gtg gtg gcc acc gac gcc tac gtg acc cgc acc aac atc         96
Val Ser Lys Val Val Ala Thr Asp Ala Tyr Val Thr Arg Thr Asn Ile
         20                  25                  30 ttc tac cac gcc agc agc tcc agg ctg ctg gcc gtg ggc cac ccc tac        144
Phe Tyr His Ala Ser Ser Ser Arg Leu Leu Ala Val Gly His Pro Tyr
         35                  40                  45 ttc ttc atc aag cgc gcc aac aag acc gtg gtg ccc aag gtg tcc ggc        192
Phe Phe Ile Lys Arg Ala Asn Lys Thr Val Val Pro Lys Val Ser Gly
 50                  55                  60 tac cag tac agg gtg ttc aag gtg gtg ctg ccc gac ccc aac aag ttc        240
Tyr Gln Tyr Arg Val Phe Lys Val Val Leu Pro Asp Pro Asn Lys Phe
 65                  70                  75                  80 gcc ctg ccc gac tcc tcc ctg ttc gac ccc acc acc cag cgc ctg gtg        288
Ala Leu Pro Asp Ser Ser Leu Phe Asp Pro Thr Thr Gln Arg Leu Val
                 85                  90                  95 tgg gcc tgc acc ggc ctg gag gtg ggc agg ggc cag ccc ctg ggc gtg        336
Trp Ala Cys Thr Gly Leu Glu Val Gly Arg Gly Gln Pro Leu Gly Val
            100                 105                 110 ggc gtg agc ggc cac ccc ttc ctg aac aag tac gac gac gtg gag aac        384
Gly Val Ser Gly His Pro Phe Leu Asn Lys Tyr Asp Asp Val Glu Asn
        115                 120                 125 tcc ggg agc ggc ggc aac ccc ggc cag gac aac agg gtg aac gtg ggc        432
Ser Gly Ser Gly Gly Asn Pro Gly Gln Asp Asn Arg Val Asn Val Gly
130                 135                 140 atg gac tac aag cag acc cag ctg tgc atg gtg ggc tgt gcc ccc ccc        480
Met Asp Tyr Lys Gln Thr Gln Leu Cys Met Val Gly Cys Ala Pro Pro
145                 150                 155                 160 ctg tgc gag cac tgg ggc aag ggc aag cag tgt acc aac acc ccc gtg        528
Leu Cys Glu His Trp Gly Lys Gly Lys Gln Cys Thr Asn Thr Pro Val
                165                 170                 175 cag gcc ggc gac tgc ccc ccc ctg gag ctg atc acc agc gtg atc cag        576
Gln Ala Gly Asp Cys Pro Pro Leu Glu Leu Ile Thr Ser Val Ile Gln
            180                 185                 190 gac ggc gac atg gtg gac acc ggc ttc ggc gcc atg aac ttc gcc gac        624
Asp Gly Asp Met Val Asp Thr Gly Phe Gly Ala Met Asn Phe Ala Asp
        195                 200                 205 ctg cag acc aac aag tcc gac gtg ccc atc gac atc tgt ggc acc acc        672
Leu Gln Thr Asn Lys Ser Asp Val Pro Ile Asp Ile Cys Gly Thr Thr
    210                 215                 220 tgt aag tac ccc gac tac ctg cag atg gcc gcc gac ccc tac ggc gac        720
Cys Lys Tyr Pro Asp Tyr Leu Gln Met Ala Ala Asp Pro Tyr Gly Asp
225                 230                 235                 240 agg ctg ttc ttc ttc ctg cgc aag gag cag atg ttc gcc agg cac ttc        768
Arg Leu Phe Phe Phe Leu Arg Lys Glu Gln Met Phe Ala Arg His Phe
                245                 250                 255 ttc aac agg gcc ggc gag gtg ggg gag ccc gtg ccc gac acc ctg atc        816
Phe Asn Arg Ala Gly Glu Val Gly Glu Pro Val Pro Asp Thr Leu Ile
            260                 265                 270 atc aag ggc agc ggc aac cgc acc tcc gtg ggg agc agc atc tac gtg        864
Ile Lys Gly Ser Gly Asn Arg Thr Ser Val Gly Ser Ser Ile Tyr Val
        275                 280                 285 aac acc ccc agc ggc tcc ctg gtg tcc tcc gag gcc cag ctg ttc aac        912
Asn Thr Pro Ser Gly Ser Leu Val Ser Ser Glu Ala Gln Leu Phe Asn
    290                 295                 300 aag ccc tac tgg ctg cag aag gcc cag ggc cac aac aac ggc atc tgt        960
Lys Pro Tyr Trp Leu Gln Lys Ala Gln Gly His Asn Asn Gly Ile Cys
305                 310                 315                 320 tgg ggc aac cag ctg ttc gtg acc gtg gtg gac acc acc cgc agc acc       1008
Trp Gly Asn Gln Leu Phe Val Thr Val Val Asp Thr Thr Arg Ser Thr
                325                 330                 335
```

-continued

```
aac atg acc ctg tgt gcc tcc gtg acc acc tcc tcc acc tac acc aac    1056
Asn Met Thr Leu Cys Ala Ser Val Thr Thr Ser Ser Thr Tyr Thr Asn
        340                 345                 350 tcc gac tac aag gag tac atg cgc cac gtg gag gag tac gac ctg cag    1104
Ser Asp Tyr Lys Glu Tyr Met Arg His Val Glu Glu Tyr Asp Leu Gln
            355                 360                 365 ttc atc ttc cag ctg tgt agc atc acc ctg tcc gcc gag gtg atg gcc    1152
Phe Ile Phe Gln Leu Cys Ser Ile Thr Leu Ser Ala Glu Val Met Ala
370                 375                 380 tac atc cac acc atg aac ccc tcc gtg ctg gag gac tgg aac ttc ggg    1200
Tyr Ile His Thr Met Asn Pro Ser Val Leu Glu Asp Trp Asn Phe Gly
385                 390                 395                 400 ctg tcc ccc ccc ccc aac ggc acc ctg gag gac acc tac agg tac gtg    1248
Leu Ser Pro Pro Pro Asn Gly Thr Leu Glu Asp Thr Tyr Arg Tyr Val
                405                 410                 415 cag tcc cag gcc atc acc tgt cag aag ccc acc ccc gag aag gag aag    1296
Gln Ser Gln Ala Ile Thr Cys Gln Lys Pro Thr Pro Glu Lys Glu Lys
            420                 425                 430 ccc gac ccc tac aag aac ctg agc ttc tgg gag gtg aac ctg aag gag    1344
Pro Asp Pro Tyr Lys Asn Leu Ser Phe Trp Glu Val Asn Leu Lys Glu
        435                 440                 445 aag ttc tcc agc gag ctg gac cag tac ccc ctg ggc cgc aag ttc ctg    1392
Lys Phe Ser Ser Glu Leu Asp Gln Tyr Pro Leu Gly Arg Lys Phe Leu
    450                 455                 460 ctg cag agc ggc tac agg ggc cgc tcc tcc atc cgc acc ggc gtg aag    1440
Leu Gln Ser Gly Tyr Arg Gly Arg Ser Ser Ile Arg Thr Gly Val Lys
465                 470                 475                 480 cgc ccc gcc gtg tcc aag gcc tcc gcc gcc ccc aag cgc aag cgc gcc    1488
Arg Pro Ala Val Ser Lys Ala Ser Ala Ala Pro Lys Arg Lys Arg Ala
                485                 490                 495 aag acc aag agg taa                                                 1503
Lys Thr Lys Arg
        500

<210> SEQ ID NO 6
<211> LENGTH: 500
<212> TYPE: PRT
<213> ORGANISM: Artificial Sequence
<220> FEATURE:
<223> OTHER INFORMATION: Polypeptide encoded by SEQ ID NO: 5

<400> SEQUENCE: 6

Met Trp Arg Pro Ser Asp Ser Thr Val Tyr Val Pro Pro Asn Pro
1               5                   10                  15

Val Ser Lys Val Val Ala Thr Asp Ala Tyr Val Thr Arg Thr Asn Ile
            20                  25                  30

Phe Tyr His Ala Ser Ser Arg Leu Leu Ala Val Gly His Pro Tyr
        35                  40                  45

Phe Phe Ile Lys Arg Ala Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Phe Leu Asn Lys Tyr Asp Asp Val Glu Asn
        115                 120                 125
```

Ser Gly Ser Gly Gly Asn Pro Gly Gln Asp Asn Arg Val Asn Val Gly
130                 135                 140

Met Asp Tyr Lys Gln Thr Gln Leu Cys Met Val Gly Cys Ala Pro Pro
145                 150                 155                 160

Leu Cys Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
                180                 185                 190

Asp Gly Asp Met Val Asp Thr Gly Phe Gly Ala Met Asn Phe Ala Asp
                195                 200                 205

Leu Gln Thr Asn Lys Ser Asp Val Pro Ile Asp Ile Cys Gly Thr Thr
210                 215                 220

Cys Lys Tyr Pro Asp Tyr Leu Gln Met Ala Ala Asp Pro Tyr Gly Asp
225                 230                 235                 240

Arg Leu Phe Phe Phe Leu Arg Lys Glu Gln Met Phe Ala Arg His Phe
                245                 250                 255

Phe Asn Arg Ala Gly Glu Val Gly Glu Pro Val Pro Asp Thr Leu Ile
                260                 265                 270

Ile Lys Gly Ser Gly Asn Arg Thr Ser Val Gly Ser Ser Ile Tyr Val
                275                 280                 285

Asn Thr Pro Ser Gly Ser Leu Val Ser Ser Glu Ala Gln Leu Phe Asn
290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Ser Val Thr Thr Ser Ser Thr Tyr Thr Asn
                340                 345                 350

Ser Asp Tyr Lys Glu Tyr Met Arg His Val Glu Glu Tyr Asp Leu Gln
                355                 360                 365

Phe Ile Phe Gln Leu Cys Ser Ile Thr Leu Ser Ala Glu Val Met Ala
370                 375                 380

Tyr Ile His Thr Met Asn Pro Ser Val Leu Glu Asp Trp Asn Phe Gly
385                 390                 395                 400

Leu Ser Pro Pro Pro Asn Gly Thr Leu Glu Asp Thr Tyr Arg Tyr Val
                405                 410                 415

Gln Ser Gln Ala Ile Thr Cys Gln Lys Pro Thr Pro Glu Lys Glu Lys
                420                 425                 430

Pro Asp Pro Tyr Lys Asn Leu Ser Phe Trp Glu Val Asn Leu Lys Glu
                435                 440                 445

Lys Phe Ser Ser Glu Leu Asp Gln Tyr Pro Leu Gly Arg Lys Phe Leu
450                 455                 460

Leu Gln Ser Gly Tyr Arg Gly Arg Ser Ser Ile Arg Thr Gly Val Lys
465                 470                 475                 480

Arg Pro Ala Val Ser Lys Ala Ser Ala Ala Pro Lys Arg Lys Arg Ala
                485                 490                 495

Lys Thr Lys Arg
            500

<210> SEQ ID NO 7
<211> LENGTH: 1404
<212> TYPE: DNA
<213> ORGANISM: Artificial Sequence
<220> FEATURE:
<223> OTHER INFORMATION: Synthetic HPV type 6b construct wt truncated

```
<220> FEATURE:
<221> NAME/KEY: CDS
<222> LOCATION: (1)..(1404)

<400> SEQUENCE: 7
```

| | | | | | | | | | | | | | | | | |
|---|---|---|---|---|---|---|---|---|---|---|---|---|---|---|---|---|
| atg | tgg | cgg | cct | agc | gac | agc | aca | gta | tat | gtg | cct | cct | cct | aac | cct | 48 |
| Met | Trp | Arg | Pro | Ser | Asp | Ser | Thr | Val | Tyr | Val | Pro | Pro | Pro | Asn | Pro | |
| 1 | | | | 5 | | | | | 10 | | | | | 15 | | |
| gta | tcc | aaa | gtt | gtt | gcc | acg | gat | gct | tat | gtt | act | cgc | acc | aac | ata | 96 |
| Val | Ser | Lys | Val | Val | Ala | Thr | Asp | Ala | Tyr | Val | Thr | Arg | Thr | Asn | Ile | |
| | | | 20 | | | | | 25 | | | | | 30 | | | |
| ttt | tat | cat | gcc | agc | agt | tct | aga | ctt | ctt | gca | gtg | gga | cat | cct | tat | 144 |
| Phe | Tyr | His | Ala | Ser | Ser | Ser | Arg | Leu | Leu | Ala | Val | Gly | His | Pro | Tyr | |
| | | 35 | | | | | 40 | | | | | 45 | | | | |
| ttt | tcc | ata | aaa | cgg | gct | aac | aaa | act | gtt | gtg | cca | aag | gtg | tca | gga | 192 |
| Phe | Ser | Ile | Lys | Arg | Ala | Asn | Lys | Thr | Val | Val | Pro | Lys | Val | Ser | Gly | |
| 50 | | | | | 55 | | | | | 60 | | | | | | |
| tat | caa | tac | agg | gta | ttt | aag | gtg | gtg | tta | cca | gat | cct | aac | aaa | ttt | 240 |
| Tyr | Gln | Tyr | Arg | Val | Phe | Lys | Val | Val | Leu | Pro | Asp | Pro | Asn | Lys | Phe | |
| 65 | | | | 70 | | | | | 75 | | | | | 80 | | |
| gca | ttg | cct | gac | tcg | tct | ctt | ttc | gat | ccc | aca | aca | caa | cgt | tta | gta | 288 |
| Ala | Leu | Pro | Asp | Ser | Ser | Leu | Phe | Asp | Pro | Thr | Thr | Gln | Arg | Leu | Val | |
| | | | | 85 | | | | | 90 | | | | | 95 | | |
| tgg | gca | tgc | aca | ggc | cta | gag | gtg | ggc | agg | gga | cag | cca | tta | ggt | gtg | 336 |
| Trp | Ala | Cys | Thr | Gly | Leu | Glu | Val | Gly | Arg | Gly | Gln | Pro | Leu | Gly | Val | |
| | | | 100 | | | | | 105 | | | | | 110 | | | |
| ggt | gta | agt | gga | cat | cct | ttc | cta | aat | aaa | tat | gat | gat | gtt | gaa | aat | 384 |
| Gly | Val | Ser | Gly | His | Pro | Phe | Leu | Asn | Lys | Tyr | Asp | Asp | Val | Glu | Asn | |
| | | 115 | | | | | 120 | | | | | 125 | | | | |
| tca | ggg | agt | ggt | ggt | aac | cct | gga | cag | gat | aac | agg | gtt | aat | gta | ggt | 432 |
| Ser | Gly | Ser | Gly | Gly | Asn | Pro | Gly | Gln | Asp | Asn | Arg | Val | Asn | Val | Gly | |
| 130 | | | | | 135 | | | | | 140 | | | | | | |
| atg | gat | tat | aaa | caa | aca | caa | tta | tgc | atg | gtt | gga | tgt | gcc | ccc | cct | 480 |
| Met | Asp | Tyr | Lys | Gln | Thr | Gln | Leu | Cys | Met | Val | Gly | Cys | Ala | Pro | Pro | |
| 145 | | | | | 150 | | | | | 155 | | | | | 160 | |
| ttg | ggc | gag | cat | tgg | ggt | aaa | ggt | aaa | cag | tgt | act | aat | aca | cct | gta | 528 |
| Leu | Gly | Glu | His | Trp | Gly | Lys | Gly | Lys | Gln | Cys | Thr | Asn | Thr | Pro | Val | |
| | | | | 165 | | | | | 170 | | | | | 175 | | |
| cag | gct | ggt | gac | tgc | ccg | ccc | tta | gaa | ctt | att | acc | agt | gtt | ata | cag | 576 |
| Gln | Ala | Gly | Asp | Cys | Pro | Pro | Leu | Glu | Leu | Ile | Thr | Ser | Val | Ile | Gln | |
| | | | 180 | | | | | 185 | | | | | 190 | | | |
| gat | ggc | gat | atg | gtt | gac | aca | ggc | ttt | ggt | gct | atg | aat | ttt | gct | gat | 624 |
| Asp | Gly | Asp | Met | Val | Asp | Thr | Gly | Phe | Gly | Ala | Met | Asn | Phe | Ala | Asp | |
| | | 195 | | | | | 200 | | | | | 205 | | | | |
| ttg | cag | acc | aat | aaa | tca | gat | gtt | cct | att | gac | ata | tgt | ggc | act | aca | 672 |
| Leu | Gln | Thr | Asn | Lys | Ser | Asp | Val | Pro | Ile | Asp | Ile | Cys | Gly | Thr | Thr | |
| 210 | | | | | 215 | | | | | 220 | | | | | | |
| tgt | aaa | tat | cca | gat | tat | tta | caa | atg | gct | gca | gac | cca | tat | ggt | gat | 720 |
| Cys | Lys | Tyr | Pro | Asp | Tyr | Leu | Gln | Met | Ala | Ala | Asp | Pro | Tyr | Gly | Asp | |
| 225 | | | | | 230 | | | | | 235 | | | | | 240 | |
| aga | tta | ttt | ttt | ttt | cta | cgg | aag | gaa | caa | atg | ttt | gcc | aga | cat | ttt | 768 |
| Arg | Leu | Phe | Phe | Phe | Leu | Arg | Lys | Glu | Gln | Met | Phe | Ala | Arg | His | Phe | |
| | | | | 245 | | | | | 250 | | | | | 255 | | |
| ttt | aac | agg | gct | ggc | gag | gtg | ggg | gaa | cct | gtg | cct | gat | aca | ctt | ata | 816 |
| Phe | Asn | Arg | Ala | Gly | Glu | Val | Gly | Glu | Pro | Val | Pro | Asp | Thr | Leu | Ile | |
| | | | 260 | | | | | 265 | | | | | 270 | | | |
| att | aag | ggt | agt | gga | aat | cgc | acg | tct | gta | ggg | agt | agt | ata | tat | gtt | 864 |
| Ile | Lys | Gly | Ser | Gly | Asn | Arg | Thr | Ser | Val | Gly | Ser | Ser | Ile | Tyr | Val | |
| | | 275 | | | | | 280 | | | | | 285 | | | | |
| aac | acc | ccg | agc | ggc | tct | ttg | gtg | tcc | tct | gag | gca | caa | ttg | ttt | aat | 912 |

```
                Asn Thr Pro Ser Gly Ser Leu Val Ser Ser Glu Ala Gln Leu Phe Asn
                        290                 295                 300 aag cca tat tgg cta caa aaa gcc cag gga cat aac aat ggt att tgt         960
Lys Pro Tyr Trp Leu Gln Lys Ala Gln Gly His Asn Asn Gly Ile Cys
305                 310                 315                 320 tgg ggt aat caa ctg ttt gtt act gtg gta gat acc aca cgc agt acc        1008
Trp Gly Asn Gln Leu Phe Val Thr Val Val Asp Thr Thr Arg Ser Thr
                325                 330                 335 aac atg aca tta tgt gca tcc gta act aca tct tcc aca tac acc aat        1056
Asn Met Thr Leu Cys Ala Ser Val Thr Thr Ser Ser Thr Tyr Thr Asn
            340                 345                 350 tct gat tat aaa gag tac atg cgt cat gtg gaa gag tat gat tta caa        1104
Ser Asp Tyr Lys Glu Tyr Met Arg His Val Glu Glu Tyr Asp Leu Gln
        355                 360                 365 ttt att ttt caa tta tgt agc att aca ttg tct gct gaa gta atg gcc        1152
Phe Ile Phe Gln Leu Cys Ser Ile Thr Leu Ser Ala Glu Val Met Ala
    370                 375                 380 tat att cac aca atg aat ccc tct gtt ttg gaa gac tgg aac ttt ggg        1200
Tyr Ile His Thr Met Asn Pro Ser Val Leu Glu Asp Trp Asn Phe Gly
385                 390                 395                 400 tta tcg cct ccc cca aat ggt aca tta gaa gat acc tat agg tat gtg        1248
Leu Ser Pro Pro Pro Asn Gly Thr Leu Glu Asp Thr Tyr Arg Tyr Val
                405                 410                 415 cag tca cag gcc att acc tgt caa aag ccc act cct gaa aag gaa aag        1296
Gln Ser Gln Ala Ile Thr Cys Gln Lys Pro Thr Pro Glu Lys Glu Lys
                420                 425                 430 cca gat ccc tat aag aac ctt agt ttt tgg gag gtt aat tta aaa gaa        1344
Pro Asp Pro Tyr Lys Asn Leu Ser Phe Trp Glu Val Asn Leu Lys Glu
            435                 440                 445 aag ttt tct agt gaa ttg gat cag tat cct ttg gga cgc aag ttt ttg        1392
Lys Phe Ser Ser Glu Leu Asp Gln Tyr Pro Leu Gly Arg Lys Phe Leu
        450                 455                 460 tta caa agt taa                                                        1404
Leu Gln Ser
465

<210> SEQ ID NO 8
<211> LENGTH: 467
<212> TYPE: PRT
<213> ORGANISM: Artificial Sequence
<220> FEATURE:
<223> OTHER INFORMATION: Polypeptide encoded by SEQ ID NO: 7

<400> SEQUENCE: 8

Met Trp Arg Pro Ser Asp Ser Thr Val Tyr Val Pro Pro Asn Pro
1               5                   10                  15

Val Ser Lys Val Val Ala Thr Asp Ala Tyr Val Thr Arg Thr Asn Ile
                20                  25                  30

Phe Tyr His Ala Ser Ser Arg Leu Leu Ala Val Gly His Pro Tyr
            35                  40                  45

Phe Ser Ile Lys Arg Ala Asn Lys Thr Val Pro Lys Val Ser Gly
        50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Phe Leu Asn Lys Tyr Asp Asp Val Glu Asn
```

```
              115                 120                 125
Ser Gly Ser Gly Gly Asn Pro Gly Gln Asp Asn Arg Val Asn Val Gly
    130                 135                 140

Met Asp Tyr Lys Gln Thr Gln Leu Cys Met Val Gly Cys Ala Pro Pro
145                 150                 155                 160

Leu Gly Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
            180                 185                 190

Asp Gly Asp Met Val Asp Thr Gly Phe Gly Ala Met Asn Phe Ala Asp
        195                 200                 205

Leu Gln Thr Asn Lys Ser Asp Val Pro Ile Asp Ile Cys Gly Thr Thr
    210                 215                 220

Cys Lys Tyr Pro Asp Tyr Leu Gln Met Ala Ala Asp Pro Tyr Gly Asp
225                 230                 235                 240

Arg Leu Phe Phe Phe Leu Arg Lys Glu Gln Met Phe Ala Arg His Phe
                245                 250                 255

Phe Asn Arg Ala Gly Glu Val Gly Glu Pro Val Pro Asp Thr Leu Ile
            260                 265                 270

Ile Lys Gly Ser Gly Asn Arg Thr Ser Val Gly Ser Ser Ile Tyr Val
        275                 280                 285

Asn Thr Pro Ser Gly Ser Leu Val Ser Ser Glu Ala Gln Leu Phe Asn
    290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Ser Val Thr Thr Ser Ser Thr Tyr Thr Asn
            340                 345                 350

Ser Asp Tyr Lys Glu Tyr Met Arg His Val Glu Glu Tyr Asp Leu Gln
        355                 360                 365

Phe Ile Phe Gln Leu Cys Ser Ile Thr Leu Ser Ala Glu Val Met Ala
    370                 375                 380

Tyr Ile His Thr Met Asn Pro Ser Val Leu Glu Asp Trp Asn Phe Gly
385                 390                 395                 400

Leu Ser Pro Pro Pro Asn Gly Thr Leu Glu Asp Thr Tyr Arg Tyr Val
                405                 410                 415

Gln Ser Gln Ala Ile Thr Cys Gln Lys Pro Thr Pro Glu Lys Glu Lys
            420                 425                 430

Pro Asp Pro Tyr Lys Asn Leu Ser Phe Trp Glu Val Asn Leu Lys Glu
        435                 440                 445

Lys Phe Ser Ser Glu Leu Asp Gln Tyr Pro Leu Gly Arg Lys Phe Leu
    450                 455                 460

Leu Gln Ser
465

<210> SEQ ID NO 9
<211> LENGTH: 1404
<212> TYPE: DNA
<213> ORGANISM: Artificial Sequence
<220> FEATURE:
<223> OTHER INFORMATION: Synthetic HPV type 6b construct humanised
      truncated
<220> FEATURE:
<221> NAME/KEY: CDS
<222> LOCATION: (1)..(1404)
```

<400> SEQUENCE: 9

```
atg tgg cgc ccc agc gac agc acc gtg tac gtg ccc ccc aac ccc      48
Met Trp Arg Pro Ser Asp Ser Thr Val Tyr Val Pro Pro Asn Pro
1               5                   10                  15 gtg tcc aag gtg gtg gcc acc gac gcc tac gtg acc cgc acc aac atc  96
Val Ser Lys Val Val Ala Thr Asp Ala Tyr Val Thr Arg Thr Asn Ile
            20                  25                  30 ttc tac cac gcc agc agc tcc agg ctg ctg gcc gtg ggc cac ccc tac  144
Phe Tyr His Ala Ser Ser Ser Arg Leu Leu Ala Val Gly His Pro Tyr
35                  40                  45 ttc ttc atc aag cgc gcc aac aag acc gtg gtg ccc aag gtg tcc ggc  192
Phe Phe Ile Lys Arg Ala Asn Lys Thr Val Val Pro Lys Val Ser Gly
    50                  55                  60 tac cag tac agg gtg ttc aag gtg gtg ctg ccc gac ccc aac aag ttc  240
Tyr Gln Tyr Arg Val Phe Lys Val Val Leu Pro Asp Pro Asn Lys Phe
65                  70                  75                  80 gcc ctg ccc gac tcc tcc ctg ttc gac ccc acc acc cag cgc ctg gtg  288
Ala Leu Pro Asp Ser Ser Leu Phe Asp Pro Thr Thr Gln Arg Leu Val
                85                  90                  95 tgg gcc tgc acc ggc ctg gag gtg ggc agg ggc cag ccc ctg ggc gtg  336
Trp Ala Cys Thr Gly Leu Glu Val Gly Arg Gly Gln Pro Leu Gly Val
            100                 105                 110 ggc gtg agc ggc cac ccc ttc ctg aac aag tac gac gac gtg gag aac  384
Gly Val Ser Gly His Pro Phe Leu Asn Lys Tyr Asp Asp Val Glu Asn
        115                 120                 125 tcc ggg agc ggc ggc aac ccc ggc cag gac aac agg gtg aac gtg ggc  432
Ser Gly Ser Gly Gly Asn Pro Gly Gln Asp Asn Arg Val Asn Val Gly
130                 135                 140 atg gac tac aag cag acc cag ctg tgc atg gtg ggc tgt gcc ccc ccc  480
Met Asp Tyr Lys Gln Thr Gln Leu Cys Met Val Gly Cys Ala Pro Pro
145                 150                 155                 160 ctg tgc gag cac tgg ggc aag ggc aag cag tgt acc aac acc ccc gtg  528
Leu Cys Glu His Trp Gly Lys Gly Lys Gln Cys Thr Asn Thr Pro Val
                165                 170                 175 cag gcc ggc gac tgc ccc ccc ctg gag ctg atc acc agc gtg atc cag  576
Gln Ala Gly Asp Cys Pro Pro Leu Glu Leu Ile Thr Ser Val Ile Gln
            180                 185                 190 gac ggc gac atg gtg gac acc ggc ttc ggc gcc atg aac ttc gcc gac  624
Asp Gly Asp Met Val Asp Thr Gly Phe Gly Ala Met Asn Phe Ala Asp
        195                 200                 205 ctg cag acc aac aag tcc gac gtg ccc atc gac atc tgt ggc acc acc  672
Leu Gln Thr Asn Lys Ser Asp Val Pro Ile Asp Ile Cys Gly Thr Thr
    210                 215                 220 tgt aag tac ccc gac tac ctg cag atg gcc gcc gac ccc tac ggc gac  720
Cys Lys Tyr Pro Asp Tyr Leu Gln Met Ala Ala Asp Pro Tyr Gly Asp
225                 230                 235                 240 agg ctg ttc ttc ttc ctg cgc aag gag cag atg ttc gcc agg cac ttc  768
Arg Leu Phe Phe Phe Leu Arg Lys Glu Gln Met Phe Ala Arg His Phe
                245                 250                 255 ttc aac agg gcc ggc gag gtg ggg gag ccc gtg ccc gac acc ctg atc  816
Phe Asn Arg Ala Gly Glu Val Gly Glu Pro Val Pro Asp Thr Leu Ile
            260                 265                 270 atc aag ggc agc ggc aac cgc acc tcc gtg ggg agc agc atc tac gtg  864
Ile Lys Gly Ser Gly Asn Arg Thr Ser Val Gly Ser Ser Ile Tyr Val
        275                 280                 285 aac acc ccc agc ggc tcc ctg gtg tcc tcc gag gcc cag ctg ttc aac  912
Asn Thr Pro Ser Gly Ser Leu Val Ser Ser Glu Ala Gln Leu Phe Asn
    290                 295                 300
```

-continued

| | |
|---|---|
| aag ccc tac tgg ctg cag aag gcc cag ggc cac aac aac ggc atc tgt<br>Lys Pro Tyr Trp Leu Gln Lys Ala Gln Gly His Asn Asn Gly Ile Cys<br>305                      310                    315                320 | 960 |
| tgg ggc aac cag ctg ttc gtg acc gtg gtg gac acc acc cgc agc acc<br>Trp Gly Asn Gln Leu Phe Val Thr Val Val Asp Thr Thr Arg Ser Thr<br>               325                    330                    335 | 1008 |
| aac atg acc ctg tgt gcc tcc gtg acc acc tcc tcc acc tac acc aac<br>Asn Met Thr Leu Cys Ala Ser Val Thr Thr Ser Ser Thr Tyr Thr Asn<br>                    340                    345              350 | 1056 |
| tcc gac tac aag gag tac atg cgc cac gtg gag gag tac gac ctg cag<br>Ser Asp Tyr Lys Glu Tyr Met Arg His Val Glu Glu Tyr Asp Leu Gln<br>355                      360                    365 | 1104 |
| ttc atc ttc cag ctg tgt agc atc acc ctg tcc gcc gag gtg atg gcc<br>Phe Ile Phe Gln Leu Cys Ser Ile Thr Leu Ser Ala Glu Val Met Ala<br>370                      375                    380 | 1152 |
| tac atc cac acc atg aac ccc tcc gtg ctg gag gac tgg aac ttc ggg<br>Tyr Ile His Thr Met Asn Pro Ser Val Leu Glu Asp Trp Asn Phe Gly<br>385                      390                    395              400 | 1200 |
| ctg tcc ccc ccc ccc aac ggc acc ctg gag gac acc tac agg tac gtg<br>Leu Ser Pro Pro Pro Asn Gly Thr Leu Glu Asp Thr Tyr Arg Tyr Val<br>                    405                    410                    415 | 1248 |
| cag tcc cag gcc atc acc tgt cag aag ccc acc ccc gag aag gag aag<br>Gln Ser Gln Ala Ile Thr Cys Gln Lys Pro Thr Pro Glu Lys Glu Lys<br>420                      425                    430 | 1296 |
| ccc gac ccc tac aag aac ctg agc ttc tgg gag gtg aac ctg aag gag<br>Pro Asp Pro Tyr Lys Asn Leu Ser Phe Trp Glu Val Asn Leu Lys Glu<br>                    435                    440                    445 | 1344 |
| aag ttc tcc agc gag ctg gac cag tac ccc ctg ggc cgc aag ttc ctg<br>Lys Phe Ser Ser Glu Leu Asp Gln Tyr Pro Leu Gly Arg Lys Phe Leu<br>     450                    455                    460 | 1392 |
| ctg cag agc taa<br>Leu Gln Ser<br>465 | 1404 |

<210> SEQ ID NO 10
<211> LENGTH: 467
<212> TYPE: PRT
<213> ORGANISM: Artificial Sequence
<220> FEATURE:
<223> OTHER INFORMATION: Polypeptide encoded by SEQ ID NO: 9

<400> SEQUENCE: 10

Met Trp Arg Pro Ser Asp Ser Thr Val Tyr Val Pro Pro Asn Pro
1               5                  10               15

Val Ser Lys Val Val Ala Thr Asp Ala Tyr Val Thr Arg Thr Asn Ile
             20                    25                    30

Phe Tyr His Ala Ser Ser Arg Leu Leu Ala Val Gly His Pro Tyr
         35                    40                    45

Phe Phe Ile Lys Arg Ala Asn Lys Thr Val Val Pro Lys Val Ser Gly
50                    55                    60

Tyr Gln Tyr Arg Val Phe Lys Val Val Leu Pro Asp Pro Asn Lys Phe
65                    70                    75                    80

Ala Leu Pro Asp Ser Ser Leu Phe Asp Pro Thr Thr Gln Arg Leu Val
               85                  90                    95

Trp Ala Cys Thr Gly Leu Glu Val Gly Arg Gly Gln Pro Leu Gly Val
            100                   105                 110

Gly Val Ser Gly His Pro Phe Leu Asn Lys Tyr Asp Asp Val Glu Asn
       115                  120                  125

Ser Gly Ser Gly Gly Asn Pro Gly Gln Asp Asn Arg Val Asn Val Gly

```
            130                 135                 140
Met Asp Tyr Lys Gln Thr Gln Leu Cys Met Val Gly Cys Ala Pro Pro
145                 150                 155                 160

Leu Cys Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
            180                 185                 190

Asp Gly Asp Met Val Asp Thr Gly Phe Gly Ala Met Asn Phe Ala Asp
                195                 200                 205

Leu Gln Thr Asn Lys Ser Asp Val Pro Ile Asp Ile Cys Gly Thr Thr
    210                 215                 220

Cys Lys Tyr Pro Asp Tyr Leu Gln Met Ala Ala Asp Pro Tyr Gly Asp
225                 230                 235                 240

Arg Leu Phe Phe Phe Leu Arg Lys Glu Gln Met Phe Ala Arg His Phe
                245                 250                 255

Phe Asn Arg Ala Gly Glu Val Gly Glu Pro Val Pro Asp Thr Leu Ile
            260                 265                 270

Ile Lys Gly Ser Gly Asn Arg Thr Ser Val Gly Ser Ser Ile Tyr Val
        275                 280                 285

Asn Thr Pro Ser Gly Ser Leu Val Ser Ser Glu Ala Gln Leu Phe Asn
    290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Ser Val Thr Thr Ser Ser Thr Tyr Thr Asn
            340                 345                 350

Ser Asp Tyr Lys Glu Tyr Met Arg His Val Glu Glu Tyr Asp Leu Gln
        355                 360                 365

Phe Ile Phe Gln Leu Cys Ser Ile Thr Leu Ser Ala Glu Val Met Ala
    370                 375                 380

Tyr Ile His Thr Met Asn Pro Ser Val Leu Glu Asp Trp Asn Phe Gly
385                 390                 395                 400

Leu Ser Pro Pro Pro Asn Gly Thr Leu Glu Asp Thr Tyr Arg Tyr Val
                405                 410                 415

Gln Ser Gln Ala Ile Thr Cys Gln Lys Pro Thr Pro Glu Lys Glu Lys
            420                 425                 430

Pro Asp Pro Tyr Lys Asn Leu Ser Phe Trp Glu Val Asn Leu Lys Glu
        435                 440                 445

Lys Phe Ser Ser Glu Leu Asp Gln Tyr Pro Leu Gly Arg Lys Phe Leu
    450                 455                 460

Leu Gln Ser
465

<210> SEQ ID NO 11
<211> LENGTH: 1554
<212> TYPE: DNA
<213> ORGANISM: Artificial Sequence
<220> FEATURE:
<223> OTHER INFORMATION: Synthetic HPV type 6b construct humanised
      hybrid
<220> FEATURE:
<221> NAME/KEY: CDS
<222> LOCATION: (1)..(1554)

<400> SEQUENCE: 11
```

-continued

| | |
|---|---|
| atg tgg cgc ccc agc gac agc acc gtg tac gtg ccc ccc ccc aac ccc<br>Met Trp Arg Pro Ser Asp Ser Thr Val Tyr Val Pro Pro Pro Asn Pro<br>1               5                   10                  15 | 48 |
| gtg tcc aag gtg gtg gcc acc gac gcc tac gtg acc cgc acc aac atc<br>Val Ser Lys Val Val Ala Thr Asp Ala Tyr Val Thr Arg Thr Asn Ile<br>            20                  25                  30 | 96 |
| ttc tac cac gcc agc agc tcc agg ctg ctg gcc gtg ggc cac ccc tac<br>Phe Tyr His Ala Ser Ser Ser Arg Leu Leu Ala Val Gly His Pro Tyr<br>        35                  40                  45 | 144 |
| ttc ttc atc aag cgc gcc aac aag acc gtg gtg ccc aag gtg tcc ggc<br>Phe Phe Ile Lys Arg Ala Asn Lys Thr Val Val Pro Lys Val Ser Gly<br>    50                  55                  60 | 192 |
| tac cag tac agg gtg ttc aag gtg gtg ctg ccc gac ccc aac aag ttc<br>Tyr Gln Tyr Arg Val Phe Lys Val Val Leu Pro Asp Pro Asn Lys Phe<br>65                  70                  75                  80 | 240 |
| gcc ctg ccc gac tcc tcc ctg ttc gac ccc acc acc cag cgc ctg gtg<br>Ala Leu Pro Asp Ser Ser Leu Phe Asp Pro Thr Thr Gln Arg Leu Val<br>                85                  90                  95 | 288 |
| tgg gcc tgc acc ggc ctg gag gtg ggc agg ggc cag ccc ctg ggc gtg<br>Trp Ala Cys Thr Gly Leu Glu Val Gly Arg Gly Gln Pro Leu Gly Val<br>            100                 105                 110 | 336 |
| ggc gtg agc ggc cac ccc ttc ctg aac aag tac gac gac gtg gag aac<br>Gly Val Ser Gly His Pro Phe Leu Asn Lys Tyr Asp Asp Val Glu Asn<br>        115                 120                 125 | 384 |
| tcc ggg agc ggc ggc aac ccc ggc cag gac aac agg gtg aac gtg ggc<br>Ser Gly Ser Gly Gly Asn Pro Gly Gln Asp Asn Arg Val Asn Val Gly<br>    130                 135                 140 | 432 |
| atg gac tac aag cag acc cag ctg tgc atg gtg ggc tgt gcc ccc ccc<br>Met Asp Tyr Lys Gln Thr Gln Leu Cys Met Val Gly Cys Ala Pro Pro<br>145                 150                 155                 160 | 480 |
| ctg tgc gag cac tgg ggc aag ggc aag cag tgt acc aac acc ccc gtg<br>Leu Cys Glu His Trp Gly Lys Gly Lys Gln Cys Thr Asn Thr Pro Val<br>                165                 170                 175 | 528 |
| cag gcc ggc gac tgc ccc ccc ctg gag ctg atc acc agc gtg atc cag<br>Gln Ala Gly Asp Cys Pro Pro Leu Glu Leu Ile Thr Ser Val Ile Gln<br>            180                 185                 190 | 576 |
| gac ggc gac atg gtg gac acc ggc ttc ggc gcc atg aac ttc gcc gac<br>Asp Gly Asp Met Val Asp Thr Gly Phe Gly Ala Met Asn Phe Ala Asp<br>        195                 200                 205 | 624 |
| ctg cag acc aac aag tcc gac gtg ccc atc gac atc tgt ggc acc acc<br>Leu Gln Thr Asn Lys Ser Asp Val Pro Ile Asp Ile Cys Gly Thr Thr<br>    210                 215                 220 | 672 |
| tgt aag tac ccc gac tac ctg cag atg gcc gcc gac ccc tac ggc gac<br>Cys Lys Tyr Pro Asp Tyr Leu Gln Met Ala Ala Asp Pro Tyr Gly Asp<br>225                 230                 235                 240 | 720 |
| agg ctg ttc ttc ttc ctg cgc aag gag cag atg ttc gcc agg cac ttc<br>Arg Leu Phe Phe Phe Leu Arg Lys Glu Gln Met Phe Ala Arg His Phe<br>                245                 250                 255 | 768 |
| ttc aac agg gcc ggc gag gtg ggg gag ccc gtg ccc gac acc ctg atc<br>Phe Asn Arg Ala Gly Glu Val Gly Glu Pro Val Pro Asp Thr Leu Ile<br>            260                 265                 270 | 816 |
| atc aag ggc agc ggc aac cgc acc tcc gtg ggg agc agc atc tac gtg<br>Ile Lys Gly Ser Gly Asn Arg Thr Ser Val Gly Ser Ser Ile Tyr Val<br>        275                 280                 285 | 864 |
| aac acc ccc agc ggc tcc ctg gtg tcc tcc gag gcc cag ctg ttc aac<br>Asn Thr Pro Ser Gly Ser Leu Val Ser Ser Glu Ala Gln Leu Phe Asn<br>    290                 295                 300 | 912 |
| aag ccc tac tgg ctg cag aag gcc cag ggc cac aac aac ggc atc tgt<br>Lys Pro Tyr Trp Leu Gln Lys Ala Gln Gly His Asn Asn Gly Ile Cys<br>305                 310                 315                 320 | 960 |

```
tgg ggc aac cag ctg ttc gtg acc gtg gtg gac acc acc cgc agc acc    1008
Trp Gly Asn Gln Leu Phe Val Thr Val Val Asp Thr Thr Arg Ser Thr
            325                 330                 335 aac atg acc ctg tgt gcc tcc gtg acc acc tcc tcc acc tac acc aac    1056
Asn Met Thr Leu Cys Ala Ser Val Thr Thr Ser Ser Thr Tyr Thr Asn
        340                 345                 350 tcc gac tac aag gag tac atg cgc cac gtg gag gag tac gac ctg cag    1104
Ser Asp Tyr Lys Glu Tyr Met Arg His Val Glu Glu Tyr Asp Leu Gln
    355                 360                 365 ttc atc ttc cag ctg tgt agc atc acc ctg tcc gcc gag gtg atg gcc    1152
Phe Ile Phe Gln Leu Cys Ser Ile Thr Leu Ser Ala Glu Val Met Ala
370                 375                 380 tac atc cac acc atg aac ccc tcc gtg ctg gag gac tgg aac ttc ggg    1200
Tyr Ile His Thr Met Asn Pro Ser Val Leu Glu Asp Trp Asn Phe Gly
385                 390                 395                 400 ctg tcc ccc ccc ccc aac ggc acc ctg gag gac acc tac agg tac gtg    1248
Leu Ser Pro Pro Pro Asn Gly Thr Leu Glu Asp Thr Tyr Arg Tyr Val
                405                 410                 415 cag tcc cag gcc atc acc tgt cag aag ccc acc ccc gag aag gag aag    1296
Gln Ser Gln Ala Ile Thr Cys Gln Lys Pro Thr Pro Glu Lys Glu Lys
            420                 425                 430 ccc gac ccc tac aag aac ctg agc ttc tgg gag gtg aac ctg aag gag    1344
Pro Asp Pro Tyr Lys Asn Leu Ser Phe Trp Glu Val Asn Leu Lys Glu
        435                 440                 445 aag ttc tcc agc gag ctg gac cag tac ccc ctg ggc cgc aag ttc ctg    1392
Lys Phe Ser Ser Glu Leu Asp Gln Tyr Pro Leu Gly Arg Lys Phe Leu
    450                 455                 460 ctg cag agc cat ggc agg acc gtg acc ctg aag gac atc gtg ctg gac    1440
Leu Gln Ser His Gly Arg Thr Val Thr Leu Lys Asp Ile Val Leu Asp
465                 470                 475                 480 ctg cag ccc ccc gac ccc gtg ggg ctg cac tgc tac gag cag ctg gtg    1488
Leu Gln Pro Pro Asp Pro Val Gly Leu His Cys Tyr Glu Gln Leu Val
                485                 490                 495 gac agc tcc gag gac gag gtg gac gag gtg gac ggc cag gac tcc cag    1536
Asp Ser Ser Glu Asp Glu Val Asp Glu Val Asp Gly Gln Asp Ser Gln
            500                 505                 510 ccc ctg aag cag cac taa                                            1554
Pro Leu Lys Gln His
        515
```

<210> SEQ ID NO 12
<211> LENGTH: 517
<212> TYPE: PRT
<213> ORGANISM: Artificial Sequence
<220> FEATURE:
<223> OTHER INFORMATION: Polypeptide encoded by SEQ ID NO: 11

<400> SEQUENCE: 12

```
Met Trp Arg Pro Ser Asp Ser Thr Val Tyr Val Pro Pro Asn Pro
1               5                   10                  15

Val Ser Lys Val Val Ala Thr Asp Ala Tyr Val Thr Thr Asn Ile
            20                  25                  30

Phe Tyr His Ala Ser Ser Arg Leu Leu Ala Val Gly His Pro Tyr
        35                  40                  45

Phe Phe Ile Lys Arg Ala Asn Lys Thr Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
```

```
                85                  90                  95
Trp Ala Cys Thr Gly Leu Glu Val Gly Arg Gly Gln Pro Leu Gly Val
            100                 105                 110
Gly Val Ser Gly His Pro Phe Leu Asn Lys Tyr Asp Val Glu Asn
        115                 120                 125
Ser Gly Ser Gly Gly Asn Pro Gly Gln Asp Asn Arg Val Asn Val Gly
    130                 135                 140
Met Asp Tyr Lys Gln Thr Gln Leu Cys Met Val Gly Cys Ala Pro Pro
145                 150                 155                 160
Leu Cys Glu His Trp Gly Lys Gly Lys Gln Cys Thr Asn Thr Pro Val
                165                 170                 175
Gln Ala Gly Asp Cys Pro Pro Leu Glu Leu Ile Thr Ser Val Ile Gln
            180                 185                 190
Asp Gly Asp Met Val Asp Thr Gly Phe Gly Ala Met Asn Phe Ala Asp
        195                 200                 205
Leu Gln Thr Asn Lys Ser Asp Val Pro Ile Asp Ile Cys Gly Thr Thr
    210                 215                 220
Cys Lys Tyr Pro Asp Tyr Leu Gln Met Ala Ala Asp Pro Tyr Gly Asp
225                 230                 235                 240
Arg Leu Phe Phe Phe Leu Arg Lys Glu Gln Met Phe Ala Arg His Phe
                245                 250                 255
Phe Asn Arg Ala Gly Glu Val Gly Glu Pro Val Pro Asp Thr Leu Ile
            260                 265                 270
Ile Lys Gly Ser Gly Asn Arg Thr Ser Val Gly Ser Ser Ile Tyr Val
        275                 280                 285
Asn Thr Pro Ser Gly Ser Leu Val Ser Ser Glu Ala Gln Leu Phe Asn
    290                 295                 300
Lys Pro Tyr Trp Leu Gln Lys Ala Gln Gly His Asn Asn Gly Ile Cys
305                 310                 315                 320
Trp Gly Asn Gln Leu Phe Val Thr Val Val Asp Thr Thr Arg Ser Thr
                325                 330                 335
Asn Met Thr Leu Cys Ala Ser Val Thr Thr Ser Ser Thr Tyr Thr Asn
            340                 345                 350
Ser Asp Tyr Lys Glu Tyr Met Arg His Val Glu Glu Tyr Asp Leu Gln
        355                 360                 365
Phe Ile Phe Gln Leu Cys Ser Ile Thr Leu Ser Ala Glu Val Met Ala
    370                 375                 380
Tyr Ile His Thr Met Asn Pro Ser Val Leu Glu Asp Trp Asn Phe Gly
385                 390                 395                 400
Leu Ser Pro Pro Pro Asn Gly Thr Leu Glu Asp Thr Tyr Arg Tyr Val
                405                 410                 415
Gln Ser Gln Ala Ile Thr Cys Gln Lys Pro Thr Pro Glu Lys Glu Lys
            420                 425                 430
Pro Asp Pro Tyr Lys Asn Leu Ser Phe Trp Glu Val Asn Leu Lys Glu
        435                 440                 445
Lys Phe Ser Ser Glu Leu Asp Gln Tyr Pro Leu Gly Arg Lys Phe Leu
    450                 455                 460
Leu Gln Ser His Gly Arg Thr Val Thr Leu Lys Asp Ile Val Leu Asp
465                 470                 475                 480
Leu Gln Pro Pro Asp Pro Val Gly Leu His Cys Tyr Glu Gln Leu Val
                485                 490                 495
Asp Ser Ser Glu Asp Glu Val Asp Glu Val Asp Gly Gln Asp Ser Gln
            500                 505                 510
```

<210> SEQ ID NO 13
<211> LENGTH: 1554
<212> TYPE: DNA
<213> ORGANISM: Artificial Sequence
<220> FEATURE:
<223> OTHER INFORMATION: Synthetic HPV type 6b construct humanised hybrid
<220> FEATURE:
<221> NAME/KEY: CDS
<222> LOCATION: (1)..(1554)

<400> SEQUENCE: 13

```
atg tgg cgc ccc agc gac agc acc gtg tac gtg ccc ccc aac ccc        48
Met Trp Arg Pro Ser Asp Ser Thr Val Tyr Val Pro Pro Asn Pro
1               5                   10                  15 gtg tcc aag gtg gtg gcc acc gac gcc tac gtg acc cgc acc aac atc   96
Val Ser Lys Val Val Ala Thr Asp Ala Tyr Val Thr Arg Thr Asn Ile
                20                  25                  30 ttc tac cac gcc agc agc tcc agg ctg ctg gcc gtg ggc cac ccc tac   144
Phe Tyr His Ala Ser Ser Ser Arg Leu Leu Ala Val Gly His Pro Tyr
            35                  40                  45 ttc ttc atc aag cgc gcc aac aag acc gtg gtg ccc aag gtg tcc ggc   192
Phe Phe Ile Lys Arg Ala Asn Lys Thr Val Val Pro Lys Val Ser Gly
        50                  55                  60 tac cag tac agg gtg ttc aag gtg gtg ctg ccc gac ccc aac aag ttc   240
Tyr Gln Tyr Arg Val Phe Lys Val Val Leu Pro Asp Pro Asn Lys Phe
65                  70                  75                  80 gcc ctg ccc gac tcc tcc ctg ttc gac ccc acc acc cag cgc ctg gtg   288
Ala Leu Pro Asp Ser Ser Leu Phe Asp Pro Thr Thr Gln Arg Leu Val
                85                  90                  95 tgg gcc tgc acc ggc ctg gag gtg ggc agg ggc cag ccc ctg ggc gtg   336
Trp Ala Cys Thr Gly Leu Glu Val Gly Arg Gly Gln Pro Leu Gly Val
                100                 105                 110 ggc gtg agc ggc cac ccc ttc ctg aac aag tac gac gac gtg gag aac   384
Gly Val Ser Gly His Pro Phe Leu Asn Lys Tyr Asp Asp Val Glu Asn
            115                 120                 125 tcc ggg agc ggc ggc aac ccc ggc cag gac aac agg gtg aac gtg ggc   432
Ser Gly Ser Gly Gly Asn Pro Gly Gln Asp Asn Arg Val Asn Val Gly
        130                 135                 140 atg gac tac aag cag acc cag ctg tgc atg gtg ggc tgt gcc ccc ccc   480
Met Asp Tyr Lys Gln Thr Gln Leu Cys Met Val Gly Cys Ala Pro Pro
145                 150                 155                 160 ctg tgc gag cac tgg ggc aag ggc aag cag tgt acc aac acc ccc gtg   528
Leu Cys Glu His Trp Gly Lys Gly Lys Gln Cys Thr Asn Thr Pro Val
                165                 170                 175 cag gcc ggc gac tgc ccc ccc ctg gag ctg atc acc agc gtg atc cag   576
Gln Ala Gly Asp Cys Pro Pro Leu Glu Leu Ile Thr Ser Val Ile Gln
                180                 185                 190 gac ggc gac atg gtg gac acc ggc ttc ggc gcc atg aac ttc gcc gac   624
Asp Gly Asp Met Val Asp Thr Gly Phe Gly Ala Met Asn Phe Ala Asp
            195                 200                 205 ctg cag acc aac aag tcc gac gtg ccc atc gac atc tgt ggc acc acc   672
Leu Gln Thr Asn Lys Ser Asp Val Pro Ile Asp Ile Cys Gly Thr Thr
        210                 215                 220 tgt aag tac ccc gac tac ctg cag atg gcc gcc gac ccc tac ggc gac   720
Cys Lys Tyr Pro Asp Tyr Leu Gln Met Ala Ala Asp Pro Tyr Gly Asp
225                 230                 235                 240 agg ctg ttc ttc ttc ctg cgc aag gag cag atg ttc gcc agg cac ttc   768
```

```
                Arg Leu Phe Phe Phe Leu Arg Lys Glu Gln Met Phe Ala Arg His Phe
                                245                 250                 255 ttc aac agg gcc ggc gag gtg ggg gag ccc gtg ccc gac acc ctg atc          816
Phe Asn Arg Ala Gly Glu Val Gly Glu Pro Val Pro Asp Thr Leu Ile
        260                 265                 270 atc aag ggc agc ggc aac cgc acc tcc gtg ggg agc agc atc tac gtg          864
Ile Lys Gly Ser Gly Asn Arg Thr Ser Val Gly Ser Ser Ile Tyr Val
        275                 280                 285 aac acc ccc agc ggc tcc ctg gtg tcc tcc gag gcc cag ctg ttc aac          912
Asn Thr Pro Ser Gly Ser Leu Val Ser Ser Glu Ala Gln Leu Phe Asn
        290                 295                 300 aag ccc tac tgg ctg cag aag gcc cag ggc cac aac aac ggc atc tgt          960
Lys Pro Tyr Trp Leu Gln Lys Ala Gln Gly His Asn Asn Gly Ile Cys
305                 310                 315                 320 tgg ggc aac cag ctg ttc gtg acc gtg gtg gac acc acc cgc agc acc         1008
Trp Gly Asn Gln Leu Phe Val Thr Val Val Asp Thr Thr Arg Ser Thr
                325                 330                 335 aac atg acc ctg tgt gcc tcc gtg acc acc tcc tcc acc tac acc aac         1056
Asn Met Thr Leu Cys Ala Ser Val Thr Thr Ser Ser Thr Tyr Thr Asn
                340                 345                 350 tcc gac tac aag gag tac atg cgc cac gtg gag gag tac gac ctg cag         1104
Ser Asp Tyr Lys Glu Tyr Met Arg His Val Glu Glu Tyr Asp Leu Gln
                355                 360                 365 ttc atc ttc cag ctg tgt agc atc acc ctg tcc gcc gag gtg atg gcc         1152
Phe Ile Phe Gln Leu Cys Ser Ile Thr Leu Ser Ala Glu Val Met Ala
        370                 375                 380 tac atc cac acc atg aac ccc tcc gtg ctg gag gac tgg aac ttc ggg         1200
Tyr Ile His Thr Met Asn Pro Ser Val Leu Glu Asp Trp Asn Phe Gly
385                 390                 395                 400 ctg tcc ccc ccc ccc aac ggc acc ctg gag gac acc tac agg tac gtg         1248
Leu Ser Pro Pro Pro Asn Gly Thr Leu Glu Asp Thr Tyr Arg Tyr Val
                405                 410                 415 cag tcc cag gcc atc acc tgt cag aag ccc acc ccc gag aag gag aag         1296
Gln Ser Gln Ala Ile Thr Cys Gln Lys Pro Thr Pro Glu Lys Glu Lys
                420                 425                 430 ccc gac ccc tac aag aac ctg agc ttc tgg gag gtg aac ctg aag gag         1344
Pro Asp Pro Tyr Lys Asn Leu Ser Phe Trp Glu Val Asn Leu Lys Glu
                435                 440                 445 aag ttc tcc agc gag ctg gac cag tac ccc ctg ggc cgc aag ttc ctg         1392
Lys Phe Ser Ser Glu Leu Asp Gln Tyr Pro Leu Gly Arg Lys Phe Leu
        450                 455                 460 ctg cag agc cat ggg cac ttc cag atc gtg acc tgt tgc tgt ggc tgt         1440
Leu Gln Ser His Gly His Phe Gln Ile Val Thr Cys Cys Cys Gly Cys
465                 470                 475                 480 gac agc aac gtg cgc ctg gtg gtg cag tgt acc gag acc gac atc agg         1488
Asp Ser Asn Val Arg Leu Val Val Gln Cys Thr Glu Thr Asp Ile Arg
                485                 490                 495 gag gtg cag cag ctg ctg ctg ggc acc ctg aac atc gtg tgt ccc atc         1536
Glu Val Gln Gln Leu Leu Leu Gly Thr Leu Asn Ile Val Cys Pro Ile
                500                 505                 510 tgc gcc ccc aag acc taa                                                 1554
Cys Ala Pro Lys Thr
        515

<210> SEQ ID NO 14
<211> LENGTH: 517
<212> TYPE: PRT
<213> ORGANISM: Artificial Sequence
<220> FEATURE:
<223> OTHER INFORMATION: Polypeptide encoded by SEQ ID NO: 13
```

<400> SEQUENCE: 14

```
Met Trp Arg Pro Ser Asp Ser Thr Val Tyr Val Pro Pro Asn Pro
1               5                   10                  15

Val Ser Lys Val Val Ala Thr Asp Ala Tyr Val Thr Arg Thr Asn Ile
            20                  25                  30

Phe Tyr His Ala Ser Ser Arg Leu Leu Ala Val Gly His Pro Tyr
        35                  40                  45

Phe Phe Ile Lys Arg Ala Asn Lys Thr Val Val Pro Lys Val Ser Gly
    50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
                100                 105                 110

Gly Val Ser Gly His Pro Phe Leu Asn Lys Tyr Asp Asp Val Glu Asn
            115                 120                 125

Ser Gly Ser Gly Gly Asn Pro Gly Gln Asp Asn Arg Val Asn Val Gly
    130                 135                 140

Met Asp Tyr Lys Gln Thr Gln Leu Cys Met Val Gly Cys Ala Pro Pro
145                 150                 155                 160

Leu Cys Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
            180                 185                 190

Asp Gly Asp Met Val Asp Thr Gly Phe Gly Ala Met Asn Phe Ala Asp
                195                 200                 205

Leu Gln Thr Asn Lys Ser Asp Val Pro Ile Asp Ile Cys Gly Thr Thr
210                 215                 220

Cys Lys Tyr Pro Asp Tyr Leu Gln Met Ala Ala Asp Pro Tyr Gly Asp
225                 230                 235                 240

Arg Leu Phe Phe Phe Leu Arg Lys Glu Gln Met Phe Ala Arg His Phe
                245                 250                 255

Phe Asn Arg Ala Gly Glu Val Gly Glu Pro Val Pro Asp Thr Leu Ile
            260                 265                 270

Ile Lys Gly Ser Gly Asn Arg Thr Ser Val Gly Ser Ser Ile Tyr Val
        275                 280                 285

Asn Thr Pro Ser Gly Ser Leu Val Ser Ser Glu Ala Gln Leu Phe Asn
290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Ser Val Thr Thr Ser Ser Thr Tyr Thr Asn
            340                 345                 350

Ser Asp Tyr Lys Glu Tyr Met Arg His Val Glu Glu Tyr Asp Leu Gln
    355                 360                 365

Phe Ile Phe Gln Leu Cys Ser Ile Thr Leu Ser Ala Glu Val Met Ala
    370                 375                 380

Tyr Ile His Thr Met Asn Pro Ser Val Leu Glu Asp Trp Asn Phe Gly
385                 390                 395                 400

Leu Ser Pro Pro Pro Asn Gly Thr Leu Glu Asp Thr Tyr Arg Tyr Val
                405                 410                 415
```

```
Gln Ser Gln Ala Ile Thr Cys Gln Lys Pro Thr Pro Glu Lys Glu Lys
            420                 425                 430

Pro Asp Pro Tyr Lys Asn Leu Ser Phe Trp Glu Val Asn Leu Lys Glu
        435                 440                 445

Lys Phe Ser Ser Glu Leu Asp Gln Tyr Pro Leu Gly Arg Lys Phe Leu
    450                 455                 460

Leu Gln Ser His Gly His Phe Gln Ile Val Thr Cys Cys Gly Cys
465             470                 475                 480

Asp Ser Asn Val Arg Leu Val Val Gln Cys Thr Glu Thr Asp Ile Arg
                485                 490                 495

Glu Val Gln Gln Leu Leu Leu Gly Thr Leu Asn Ile Val Cys Pro Ile
            500                 505                 510

Cys Ala Pro Lys Thr
        515

<210> SEQ ID NO 15
<211> LENGTH: 1728
<212> TYPE: DNA
<213> ORGANISM: Artificial Sequence
<220> FEATURE:
<223> OTHER INFORMATION: Synthetic HPV type 6b construct humanised
      hybrid
<220> FEATURE:
<221> NAME/KEY: CDS
<222> LOCATION: (1)..(1728)

<400> SEQUENCE: 15
```

| | |
|---|---|
| atg cag atc ttc gtg aag acc ctg acc ggg aag acc atc acc ctg gag<br>Met Gln Ile Phe Val Lys Thr Leu Thr Gly Lys Thr Ile Thr Leu Glu<br>1               5                   10                  15 | 48 |
| gtg gag ccc tcc gac acc atc gag aac gtg aag gcc aag atc cag gac<br>Val Glu Pro Ser Asp Thr Ile Glu Asn Val Lys Ala Lys Ile Gln Asp<br>            20                  25                  30 | 96 |
| aag gag ggc atc ccc ccc gac cag cag agg ctg atc ttc gcc ggc aag<br>Lys Glu Gly Ile Pro Pro Asp Gln Gln Arg Leu Ile Phe Ala Gly Lys<br>        35                  40                  45 | 144 |
| cag ctg gag gac ggc cgc acc ctg tcc gac tac aac atc cag aag gag<br>Gln Leu Glu Asp Gly Arg Thr Leu Ser Asp Tyr Asn Ile Gln Lys Glu<br>50                  55                  60 | 192 |
| tcc acc ctg cac ctg gtg ctg agg ctg cgc ggc gcc tgg cgc ccc agc<br>Ser Thr Leu His Leu Val Leu Arg Leu Arg Gly Ala Trp Arg Pro Ser<br>65                  70                  75                  80 | 240 |
| gac agc acc gtg tac gtg ccc ccc aac ccc gtg tcc aag gtg gtg<br>Asp Ser Thr Val Tyr Val Pro Pro Asn Pro Val Ser Lys Val Val<br>                85                  90                  95 | 288 |
| gcc acc gac gcc tac gtg acc cgc acc aac atc ttc tac cac gcc agc<br>Ala Thr Asp Ala Tyr Val Thr Arg Thr Asn Ile Phe Tyr His Ala Ser<br>            100                 105                 110 | 336 |
| agc tcc agg ctg ctg gcc gtg ggc cac ccc tac ttc ttc atc aag cgc<br>Ser Ser Arg Leu Leu Ala Val Gly His Pro Tyr Phe Phe Ile Lys Arg<br>        115                 120                 125 | 384 |
| gcc aac aag acc gtg gtg ccc aag gtg tcc ggc tac cag tac agg gtg<br>Ala Asn Lys Thr Val Val Pro Lys Val Ser Gly Tyr Gln Tyr Arg Val<br>    130                 135                 140 | 432 |
| ttc aag gtg gtg ctg ccc gac ccc aac aag ttc gcc ctg ccc gac tcc<br>Phe Lys Val Val Leu Pro Asp Pro Asn Lys Phe Ala Leu Pro Asp Ser<br>145                 150                 155                 160 | 480 |
| tcc ctg ttc gac ccc acc acc cag cgc ctg gtg tgg gcc tgc acc ggc<br>Ser Leu Phe Asp Pro Thr Thr Gln Arg Leu Val Trp Ala Cys Thr Gly<br>                165                 170                 175 | 528 |

```
ctg gag gtg ggc agg ggc cag ccc ctg ggc gtg ggc gtg agc ggc cac      576
Leu Glu Val Gly Arg Gly Gln Pro Leu Gly Val Gly Val Ser Gly His
            180                 185                 190 ccc ttc ctg aac aag tac gac gac gtg gag aac tcg ggg agc ggc ggc      624
Pro Phe Leu Asn Lys Tyr Asp Asp Val Glu Asn Ser Gly Ser Gly Gly
        195                 200                 205 aac ccc ggc cag gac aac agg gtg aac gtg ggc atg gac tac aag cag      672
Asn Pro Gly Gln Asp Asn Arg Val Asn Val Gly Met Asp Tyr Lys Gln
    210                 215                 220 acc cag ctg tgc atg gtg ggc tgt gcc ccc ctg tgc gag cac tgg          720
Thr Gln Leu Cys Met Val Gly Cys Ala Pro Pro Leu Cys Glu His Trp
225                 230                 235                 240 ggc aag ggc aag cag tgt acc aac acc ccc gtg cag gcc ggc gac tgc      768
Gly Lys Gly Lys Gln Cys Thr Asn Thr Pro Val Gln Ala Gly Asp Cys
                245                 250                 255 ccc ccc ctg gag ctg atc acc agc gtg atc cag gac ggc gac atg gtg      816
Pro Pro Leu Glu Leu Ile Thr Ser Val Ile Gln Asp Gly Asp Met Val
            260                 265                 270 gac acc ggc ttc ggc gcc atg aac ttc gcc gac ctg cag acc aac aag      864
Asp Thr Gly Phe Gly Ala Met Asn Phe Ala Asp Leu Gln Thr Asn Lys
        275                 280                 285 tcc gac gtg ccc atc gac atc tgt ggc acc acc tgt aag tac ccc gac      912
Ser Asp Val Pro Ile Asp Ile Cys Gly Thr Thr Cys Lys Tyr Pro Asp
    290                 295                 300 tac ctg cag atg gcc gcc gac ccc tac ggc gac agg ctg ttc ttc ttc      960
Tyr Leu Gln Met Ala Ala Asp Pro Tyr Gly Asp Arg Leu Phe Phe Phe
305                 310                 315                 320 ctg cgc aag gag cag atg ttc gcc agg cac ttc ttc aac agg gcc ggc     1008
Leu Arg Lys Glu Gln Met Phe Ala Arg His Phe Phe Asn Arg Ala Gly
                325                 330                 335 gag gtg ggg gag ccc gtg ccc gac acc ctg atc atc aag ggc agc ggc     1056
Glu Val Gly Glu Pro Val Pro Asp Thr Leu Ile Ile Lys Gly Ser Gly
            340                 345                 350 aac cgc acc tcc gtg ggg agc agc atc tac gtg aac acc ccc agc ggc     1104
Asn Arg Thr Ser Val Gly Ser Ser Ile Tyr Val Asn Thr Pro Ser Gly
        355                 360                 365 tcc ctg gtg tcc tcc gag gcc cag ctg ttc aac aag ccc tac tgg ctg     1152
Ser Leu Val Ser Ser Glu Ala Gln Leu Phe Asn Lys Pro Tyr Trp Leu
370                 375                 380 cag aag gcc cag ggc cac aac aac ggc atc tgt tgg ggc aac cag ctg     1200
Gln Lys Ala Gln Gly His Asn Asn Gly Ile Cys Trp Gly Asn Gln Leu
385                 390                 395                 400 ttc gtg acc gtg gtg gac acc acc cgc agc acc aac atg acc ctg tgt     1248
Phe Val Thr Val Val Asp Thr Thr Arg Ser Thr Asn Met Thr Leu Cys
                405                 410                 415 gcc tcc gtg acc acc tcc tcc acc tac acc aac tcc gac tac aag gag     1296
Ala Ser Val Thr Thr Ser Ser Thr Tyr Thr Asn Ser Asp Tyr Lys Glu
            420                 425                 430 tac atg cgc cac gtg gag gag tac gac ctg cag ttc atc ttc cag ctg     1344
Tyr Met Arg His Val Glu Glu Tyr Asp Leu Gln Phe Ile Phe Gln Leu
        435                 440                 445 tgt agc atc acc ctg tcc gcc gag gtg atg gcc tac atc cac acc atg     1392
Cys Ser Ile Thr Leu Ser Ala Glu Val Met Ala Tyr Ile His Thr Met
    450                 455                 460 aac ccc tcc gtg ctg gag gac tgg aac ttc ggg ctg tcc ccc ccc ccc     1440
Asn Pro Ser Val Leu Glu Asp Trp Asn Phe Gly Leu Ser Pro Pro Pro
465                 470                 475                 480 aac ggc acc ctg gag gac acc tac agg tac gtg cag tcc cag gcc atc     1488
Asn Gly Thr Leu Glu Asp Thr Tyr Arg Tyr Val Gln Ser Gln Ala Ile
```

```
acc tgt cag aag ccc acc ccc gag aag gag aag ccc gac ccc tac aag      1536
Thr Cys Gln Lys Pro Thr Pro Glu Lys Glu Lys Pro Asp Pro Tyr Lys
            500                 505                 510 aac ctg agc ttc tgg gag gtg aac ctg aag gag aag ttc tcc agc gag      1584
Asn Leu Ser Phe Trp Glu Val Asn Leu Lys Glu Lys Phe Ser Ser Glu
        515                 520                 525 ctg gac cag tac ccc ctg ggc cgc aag ttc ctg ctg cag agc ggc tac      1632
Leu Asp Gln Tyr Pro Leu Gly Arg Lys Phe Leu Leu Gln Ser Gly Tyr
    530                 535                 540 agg ggc cgc tcc tcc atc cgc acc ggc gtg aag cgc ccc gcc gtg tcc      1680
Arg Gly Arg Ser Ser Ile Arg Thr Gly Val Lys Arg Pro Ala Val Ser
545                 550                 555                 560 aag gcc tcc gcc gcc ccc aag cgc aag cgc gcc aag acc aag agg taa      1728
Lys Ala Ser Ala Ala Pro Lys Arg Lys Arg Ala Lys Thr Lys Arg
                565                 570                 575
```

<210> SEQ ID NO 16
<211> LENGTH: 575
<212> TYPE: PRT
<213> ORGANISM: Artificial Sequence
<220> FEATURE:
<223> OTHER INFORMATION: Polypeptide encoded by SEQ ID NO: 15

<400> SEQUENCE: 16

```
Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Ala Trp Arg Pro Ser
65                  70                  75                  80

Asp Ser Thr Val Tyr Val Pro Pro Asn Pro Val Ser Lys Val Val
                85                  90                  95

Ala Thr Asp Ala Tyr Val Thr Arg Thr Asn Ile Phe Tyr His Ala Ser
            100                 105                 110

Ser Ser Arg Leu Leu Ala Val Gly His Pro Tyr Phe Phe Ile Lys Arg
        115                 120                 125

Ala Asn Lys Thr Val Val Pro Lys Val Ser Gly Tyr Gln Tyr Arg Val
    130                 135                 140

Phe Lys Val Val Leu Pro Asp Pro Asn Lys Phe Ala Leu Pro Asp Ser
145                 150                 155                 160

Ser Leu Phe Asp Pro Thr Thr Gln Arg Leu Val Trp Ala Cys Thr Gly
                165                 170                 175

Leu Glu Val Gly Arg Gly Gln Pro Leu Gly Val Gly Val Ser Gly His
            180                 185                 190

Pro Phe Leu Asn Lys Tyr Asp Asp Val Glu Asn Ser Gly Ser Gly Gly
        195                 200                 205

Asn Pro Gly Gln Asp Asn Arg Val Asn Val Gly Met Asp Tyr Lys Gln
    210                 215                 220

Thr Gln Leu Cys Met Val Gly Cys Ala Pro Leu Cys Glu His Trp
225                 230                 235                 240

Gly Lys Gly Lys Gln Cys Thr Asn Thr Pro Val Gln Ala Gly Asp Cys
                245                 250                 255
```

```
Pro Pro Leu Glu Leu Ile Thr Ser Val Ile Gln Asp Gly Asp Met Val
            260                 265                 270

Asp Thr Gly Phe Gly Ala Met Asn Phe Ala Asp Leu Gln Thr Asn Lys
        275                 280                 285

Ser Asp Val Pro Ile Asp Ile Cys Gly Thr Thr Cys Lys Tyr Pro Asp
290                 295                 300

Tyr Leu Gln Met Ala Ala Asp Pro Tyr Gly Asp Arg Leu Phe Phe Phe
305                 310                 315                 320

Leu Arg Lys Glu Gln Met Phe Ala Arg His Phe Phe Asn Arg Ala Gly
                325                 330                 335

Glu Val Gly Glu Pro Val Pro Asp Thr Leu Ile Ile Lys Gly Ser Gly
            340                 345                 350

Asn Arg Thr Ser Val Gly Ser Ser Ile Tyr Val Asn Thr Pro Ser Gly
        355                 360                 365

Ser Leu Val Ser Ser Glu Ala Gln Leu Phe Asn Lys Pro Tyr Trp Leu
    370                 375                 380

Gln Lys Ala Gln Gly His Asn Asn Gly Ile Cys Trp Gly Asn Gln Leu
385                 390                 395                 400

Phe Val Thr Val Val Asp Thr Thr Arg Ser Thr Asn Met Thr Leu Cys
                405                 410                 415

Ala Ser Val Thr Thr Ser Ser Thr Tyr Thr Asn Ser Asp Tyr Lys Glu
            420                 425                 430

Tyr Met Arg His Val Glu Glu Tyr Asp Leu Gln Phe Ile Phe Gln Leu
        435                 440                 445

Cys Ser Ile Thr Leu Ser Ala Glu Val Met Ala Tyr Ile His Thr Met
    450                 455                 460

Asn Pro Ser Val Leu Glu Asp Trp Asn Phe Gly Leu Ser Pro Pro Pro
465                 470                 475                 480

Asn Gly Thr Leu Glu Asp Thr Tyr Arg Tyr Val Gln Ser Gln Ala Ile
                485                 490                 495

Thr Cys Gln Lys Pro Thr Pro Glu Lys Glu Lys Pro Asp Pro Tyr Lys
            500                 505                 510

Asn Leu Ser Phe Trp Glu Val Asn Leu Lys Glu Lys Phe Ser Ser Glu
        515                 520                 525

Leu Asp Gln Tyr Pro Leu Gly Arg Lys Phe Leu Leu Gln Ser Gly Tyr
    530                 535                 540

Arg Gly Arg Ser Ser Ile Arg Thr Gly Val Lys Arg Pro Ala Val Ser
545                 550                 555                 560

Lys Ala Ser Ala Ala Pro Lys Arg Lys Arg Ala Lys Thr Lys Arg
                565                 570                 575

<210> SEQ ID NO 17
<211> LENGTH: 1677
<212> TYPE: DNA
<213> ORGANISM: Artificial Sequence
<220> FEATURE:
<223> OTHER INFORMATION: Synthetic HPV type 6b construct humanised
      hybrid
<220> FEATURE:
<221> NAME/KEY: CDS
<222> LOCATION: (1)..(1677)

<400> SEQUENCE: 17 atg cag atc ttc gtg aag acc ctg acc ggg aag acc atc acc ctg gag      48
Met Gln Ile Phe Val Lys Thr Leu Thr Gly Lys Thr Ile Thr Leu Glu
1               5                   10                  15
```

```
gtg gag ccc tcc gac acc atc gag aac gtg aag gcc aag atc cag gac      96
Val Glu Pro Ser Asp Thr Ile Glu Asn Val Lys Ala Lys Ile Gln Asp
         20                  25                  30 aag gag ggc atc ccc ccc gac cag cag agg ctg atc ttc gcc ggc aag     144
Lys Glu Gly Ile Pro Pro Asp Gln Gln Arg Leu Ile Phe Ala Gly Lys
         35                  40                  45 cag ctg gag gac ggc cgc acc ctg tcc gac tac aac atc cag aag gag     192
Gln Leu Glu Asp Gly Arg Thr Leu Ser Asp Tyr Asn Ile Gln Lys Glu
 50                  55                  60 tcc acc ctg cac ctg gtg ctg agg ctg cgc ggc gcc tgg cgc ccc agc     240
Ser Thr Leu His Leu Val Leu Arg Leu Arg Gly Ala Trp Arg Pro Ser
 65                  70                  75                  80 gac agc acc gtg tac gtg ccc ccc aac ccc gtg tcc aag gtg gtg         288
Asp Ser Thr Val Tyr Val Pro Pro Asn Pro Val Ser Lys Val Val
                 85                  90                  95 gcc acc gac gcc tac gtg acc cgc acc aac atc ttc tac cac gcc agc     336
Ala Thr Asp Ala Tyr Val Thr Arg Thr Asn Ile Phe Tyr His Ala Ser
             100                 105                 110 agc tcc agg ctg ctg gcc gtg ggc cac ccc tac ttc ttc atc aag cgc     384
Ser Ser Arg Leu Leu Ala Val Gly His Pro Tyr Phe Phe Ile Lys Arg
         115                 120                 125 gcc aac aag acc gtg gtg ccc aag gtg tcc ggc tac cag tac agg gtg     432
Ala Asn Lys Thr Val Val Pro Lys Val Ser Gly Tyr Gln Tyr Arg Val
 130                 135                 140 ttc aag gtg gtg ctg ccc gac ccc aac aag ttc gcc ctg ccc gac tcc     480
Phe Lys Val Val Leu Pro Asp Pro Asn Lys Phe Ala Leu Pro Asp Ser
145                 150                 155                 160 tcc ctg ttc gac ccc acc acc cag cgc ctg gtg tgg gcc tgc acc ggc     528
Ser Leu Phe Asp Pro Thr Thr Gln Arg Leu Val Trp Ala Cys Thr Gly
                 165                 170                 175 ctg gag gtg ggc agg ggc cag ccc ctg ggc gtg ggc gtg agc ggc cac     576
Leu Glu Val Gly Arg Gly Gln Pro Leu Gly Val Gly Val Ser Gly His
             180                 185                 190 ccc ttc ctg aac aag tac gac gac gtg gag aac tcc ggg agc ggc ggc     624
Pro Phe Leu Asn Lys Tyr Asp Asp Val Glu Asn Ser Gly Ser Gly Gly
         195                 200                 205 aac ccc ggc cag gac aac agg gtg aac gtg ggc atg gac tac aag cag     672
Asn Pro Gly Gln Asp Asn Arg Val Asn Val Gly Met Asp Tyr Lys Gln
 210                 215                 220 acc cag ctg tgc atg gtg ggc tgt gcc ccc ccc ctg tgc gag cac tgg     720
Thr Gln Leu Cys Met Val Gly Cys Ala Pro Pro Leu Cys Glu His Trp
225                 230                 235                 240 ggc aag ggc aag cag tgt acc aac acc ccc gtg cag gcc ggc gac tgc     768
Gly Lys Gly Lys Gln Cys Thr Asn Thr Pro Val Gln Ala Gly Asp Cys
                 245                 250                 255 ccc ccc ctg gag ctg atc acc agc gtg atc cag gac ggc gac atg gtg     816
Pro Pro Leu Glu Leu Ile Thr Ser Val Ile Gln Asp Gly Asp Met Val
             260                 265                 270 gac acc ggc ttc ggc gcc atg aac ttc gcc gac ctg cag acc aac aag     864
Asp Thr Gly Phe Gly Ala Met Asn Phe Ala Asp Leu Gln Thr Asn Lys
         275                 280                 285 tcc gac gtg ccc atc gac atc tgt ggc acc acc tgt aag tac ccc gac     912
Ser Asp Val Pro Ile Asp Ile Cys Gly Thr Thr Cys Lys Tyr Pro Asp
 290                 295                 300 tac ctg cag atg gcc gcc gac ccc tac ggc gac agg ctg ttc ttc ttc     960
Tyr Leu Gln Met Ala Ala Asp Pro Tyr Gly Asp Arg Leu Phe Phe Phe
305                 310                 315                 320 ctg cgc aag gag cag atg ttc gcc agg cac ttc ttc aac agg gcc ggc    1008
Leu Arg Lys Glu Gln Met Phe Ala Arg His Phe Phe Asn Arg Ala Gly
                 325                 330                 335
```

```
gag gtg ggg gag ccc gtg ccc gac acc ctg atc atc aag ggc agc ggc     1056
Glu Val Gly Glu Pro Val Pro Asp Thr Leu Ile Ile Lys Gly Ser Gly
            340                 345                 350 aac cgc acc tcc gtg ggg agc agc atc tac gtg aac acc ccc agc ggc     1104
Asn Arg Thr Ser Val Gly Ser Ser Ile Tyr Val Asn Thr Pro Ser Gly
        355                 360                 365 tcc ctg gtg tcc tcc gag gcc cag ctg ttc aac aag ccc tac tgg ctg     1152
Ser Leu Val Ser Ser Glu Ala Gln Leu Phe Asn Lys Pro Tyr Trp Leu
    370                 375                 380 cag aag gcc cag ggc cac aac aac ggc atc tgt tgg ggc aac cag ctg     1200
Gln Lys Ala Gln Gly His Asn Asn Gly Ile Cys Trp Gly Asn Gln Leu
385                 390                 395                 400 ttc gtg acc gtg gtg gac acc acc cgc agc acc aac atg acc ctg tgt     1248
Phe Val Thr Val Val Asp Thr Thr Arg Ser Thr Asn Met Thr Leu Cys
                405                 410                 415 gcc tcc gtg acc acc tcc tcc acc tac acc aac tcc gac tac aag gag     1296
Ala Ser Val Thr Thr Ser Ser Thr Tyr Thr Asn Ser Asp Tyr Lys Glu
            420                 425                 430 tac atg cgc cac gtg gag gag tac gac ctg cag ttc atc ttc cag ctg     1344
Tyr Met Arg His Val Glu Glu Tyr Asp Leu Gln Phe Ile Phe Gln Leu
        435                 440                 445 tgt agc atc acc ctg tcc gcc gag gtg atg gcc tac atc cac acc atg     1392
Cys Ser Ile Thr Leu Ser Ala Glu Val Met Ala Tyr Ile His Thr Met
    450                 455                 460 aac ccc tcc gtg ctg gag gac tgg aac ttc ggg ctg tcc ccc ccc ccc     1440
Asn Pro Ser Val Leu Glu Asp Trp Asn Phe Gly Leu Ser Pro Pro Pro
465                 470                 475                 480 aac ggc acc ctg gag gac acc tac agg tac gtg cag tcc cag gcc atc     1488
Asn Gly Thr Leu Glu Asp Thr Tyr Arg Tyr Val Gln Ser Gln Ala Ile
                485                 490                 495 acc tgt cag aag ccc acc ccc gag aag gag aag ccc gac ccc tac aag     1536
Thr Cys Gln Lys Pro Thr Pro Glu Lys Glu Lys Pro Asp Pro Tyr Lys
            500                 505                 510 aac ctg agc ttc tgg gag gtg aac ctg aag gag aag ttc tcc agc gag     1584
Asn Leu Ser Phe Trp Glu Val Asn Leu Lys Glu Lys Phe Ser Ser Glu
        515                 520                 525 ctg gac cag tac ccc ctg ggc cgc aag ttc ctg ctg cag agc cag gcc     1632
Leu Asp Gln Tyr Pro Leu Gly Arg Lys Phe Leu Leu Gln Ser Gln Ala
    530                 535                 540 gag ccc gac cgc gcc cac tac aac atc gtc acc ttc aaa aaa taa         1677
Glu Pro Asp Arg Ala His Tyr Asn Ile Val Thr Phe Lys Lys
545                 550                 555

<210> SEQ ID NO 18
<211> LENGTH: 558
<212> TYPE: PRT
<213> ORGANISM: Artificial Sequence
<220> FEATURE:
<223> OTHER INFORMATION: Polypeptide encoded by SEQ ID NO: 17

<400> SEQUENCE: 18

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60
```

-continued

```
Ser Thr Leu His Leu Val Leu Arg Leu Arg Gly Ala Trp Arg Pro Ser
 65                  70                  75                  80

Asp Ser Thr Val Tyr Val Pro Pro Asn Pro Val Ser Lys Val Val
                 85                  90                  95

Ala Thr Asp Ala Tyr Val Thr Arg Thr Asn Ile Phe Tyr His Ala Ser
            100                 105                 110

Ser Ser Arg Leu Leu Ala Val Gly His Pro Tyr Phe Ile Lys Arg
            115                 120                 125

Ala Asn Lys Thr Val Val Pro Lys Val Ser Gly Tyr Gln Tyr Arg Val
            130                 135                 140

Phe Lys Val Val Leu Pro Asp Pro Asn Lys Phe Ala Leu Pro Asp Ser
145                 150                 155                 160

Ser Leu Phe Asp Pro Thr Thr Gln Arg Leu Val Trp Ala Cys Thr Gly
                165                 170                 175

Leu Glu Val Gly Arg Gly Gln Pro Leu Gly Val Gly Val Ser Gly His
                180                 185                 190

Pro Phe Leu Asn Lys Tyr Asp Asp Val Glu Asn Ser Gly Ser Gly Gly
            195                 200                 205

Asn Pro Gly Gln Asp Asn Arg Val Asn Val Gly Met Asp Tyr Lys Gln
            210                 215                 220

Thr Gln Leu Cys Met Val Gly Cys Ala Pro Pro Leu Cys Glu His Trp
225                 230                 235                 240

Gly Lys Gly Lys Gln Cys Thr Asn Thr Pro Val Gln Ala Gly Asp Cys
                245                 250                 255

Pro Pro Leu Glu Leu Ile Thr Ser Val Ile Gln Asp Gly Asp Met Val
            260                 265                 270

Asp Thr Gly Phe Gly Ala Met Asn Phe Ala Asp Leu Gln Thr Asn Lys
            275                 280                 285

Ser Asp Val Pro Ile Asp Ile Cys Gly Thr Thr Cys Lys Tyr Pro Asp
            290                 295                 300

Tyr Leu Gln Met Ala Ala Asp Pro Tyr Gly Asp Arg Leu Phe Phe Phe
305                 310                 315                 320

Leu Arg Lys Glu Gln Met Phe Ala Arg His Phe Phe Asn Arg Ala Gly
                325                 330                 335

Glu Val Gly Glu Pro Val Pro Asp Thr Leu Ile Ile Lys Gly Ser Gly
            340                 345                 350

Asn Arg Thr Ser Val Gly Ser Ser Ile Tyr Val Asn Thr Pro Ser Gly
            355                 360                 365

Ser Leu Val Ser Ser Glu Ala Gln Leu Phe Asn Lys Pro Tyr Trp Leu
            370                 375                 380

Gln Lys Ala Gln Gly His Asn Asn Gly Ile Cys Trp Gly Asn Gln Leu
385                 390                 395                 400

Phe Val Thr Val Val Asp Thr Thr Arg Ser Thr Asn Met Thr Leu Cys
                405                 410                 415

Ala Ser Val Thr Thr Ser Ser Thr Tyr Thr Asn Ser Asp Tyr Lys Glu
            420                 425                 430

Tyr Met Arg His Val Glu Glu Tyr Asp Leu Gln Phe Ile Phe Gln Leu
            435                 440                 445

Cys Ser Ile Thr Leu Ser Ala Glu Val Met Ala Tyr Ile His Thr Met
            450                 455                 460

Asn Pro Ser Val Leu Glu Asp Trp Asn Phe Gly Leu Ser Pro Pro Pro
465                 470                 475                 480

Asn Gly Thr Leu Glu Asp Thr Tyr Arg Tyr Val Gln Ser Gln Ala Ile
```

```
                       485                 490                 495
Thr Cys Gln Lys Pro Thr Pro Glu Lys Glu Lys Pro Asp Pro Tyr Lys
                500                 505                 510

Asn Leu Ser Phe Trp Glu Val Asn Leu Lys Glu Lys Phe Ser Ser Glu
            515                 520                 525

Leu Asp Gln Tyr Pro Leu Gly Arg Lys Phe Leu Leu Gln Ser Gln Ala
530                 535                 540

Glu Pro Asp Arg Ala His Tyr Asn Ile Val Thr Phe Lys Lys
545                 550                 555

<210> SEQ ID NO 19
<211> LENGTH: 1452
<212> TYPE: DNA
<213> ORGANISM: Artificial Sequence
<220> FEATURE:
<223> OTHER INFORMATION: Synthetic HPV type 6b construct humanised
      hybrid
<220> FEATURE:
<221> NAME/KEY: CDS
<222> LOCATION: (1)..(1452)

<400> SEQUENCE: 19 atg tgg cgc ccc agc gac agc acc gtg tac gtg ccc ccc aac ccc        48
Met Trp Arg Pro Ser Asp Ser Thr Val Tyr Val Pro Pro Asn Pro
1               5                   10                  15 gtg tcc aag gtg gtg gcc acc gac gcc tac gtg acc cgc acc aac atc    96
Val Ser Lys Val Val Ala Thr Asp Ala Tyr Val Thr Arg Thr Asn Ile
                20                  25                  30 ttc tac cac gcc agc agc tcc agg ctg ctg gcc gtg ggc cac ccc tac   144
Phe Tyr His Ala Ser Ser Ser Arg Leu Leu Ala Val Gly His Pro Tyr
            35                  40                  45 ttc ttc atc aag cgc gcc aac aag acc gtg gtg ccc aag gtg tcc ggc   192
Phe Phe Ile Lys Arg Ala Asn Lys Thr Val Val Pro Lys Val Ser Gly
        50                  55                  60 tac cag tac agg gtg ttc aag gtg gtg ctg ccc gac ccc aac aag ttc   240
Tyr Gln Tyr Arg Val Phe Lys Val Val Leu Pro Asp Pro Asn Lys Phe
65                  70                  75                  80 gcc ctg ccc gac tcc tcc ctg ttc gac ccc acc acc cag cgc ctg gtg   288
Ala Leu Pro Asp Ser Ser Leu Phe Asp Pro Thr Thr Gln Arg Leu Val
                85                  90                  95 tgg gcc tgc acc ggc ctg gag gtg ggc agg ggc cag ccc ctg ggc gtg   336
Trp Ala Cys Thr Gly Leu Glu Val Gly Arg Gly Gln Pro Leu Gly Val
            100                 105                 110 ggc gtg agc ggc cac ccc ttc ctg aac aag tac gac gac gtg gag aac   384
Gly Val Ser Gly His Pro Phe Leu Asn Lys Tyr Asp Asp Val Glu Asn
        115                 120                 125 tcc ggg agc ggc ggc aac ccc ggc cag gac aac agg gtg aac gtg ggc   432
Ser Gly Ser Gly Gly Asn Pro Gly Gln Asp Asn Arg Val Asn Val Gly
130                 135                 140 atg gac tac aag cag acc cag ctg tgc atg gtg ggc tgt gcc ccc ccc   480
Met Asp Tyr Lys Gln Thr Gln Leu Cys Met Val Gly Cys Ala Pro Pro
145                 150                 155                 160 ctg tgc gag cac tgg ggc aag ggc aag cag tgt acc aac acc ccc gtg   528
Leu Cys Glu His Trp Gly Lys Gly Lys Gln Cys Thr Asn Thr Pro Val
                165                 170                 175 cag gcc ggc gac tgc ccc ccc ctg gag ctg atc acc agc gtg atc cag   576
Gln Ala Gly Asp Cys Pro Pro Leu Glu Leu Ile Thr Ser Val Ile Gln
            180                 185                 190 gac ggc gac atg gtg gac acc ggc ttc ggc gcc atg aac ttc gcc gac   624
Asp Gly Asp Met Val Asp Thr Gly Phe Gly Ala Met Asn Phe Ala Asp
        195                 200                 205
```

```
ctg cag acc aac aag tcc gac gtg ccc atc gac atc tgt ggc acc acc      672
Leu Gln Thr Asn Lys Ser Asp Val Pro Ile Asp Ile Cys Gly Thr Thr
    210                 215                 220 tgt aag tac ccc gac tac ctg cag atg gcc gcc gac ccc tac ggc gac      720
Cys Lys Tyr Pro Asp Tyr Leu Gln Met Ala Ala Asp Pro Tyr Gly Asp
225                 230                 235                 240 agg ctg ttc ttc ttc ctg cgc aag gag cag atg ttc gcc agg cac ttc      768
Arg Leu Phe Phe Phe Leu Arg Lys Glu Gln Met Phe Ala Arg His Phe
                245                 250                 255 ttc aac agg gcc ggc gag gtg ggg gag ccc gtg ccc gac acc ctg atc      816
Phe Asn Arg Ala Gly Glu Val Gly Glu Pro Val Pro Asp Thr Leu Ile
            260                 265                 270 atc aag ggc agc ggc aac cgc acc tcc gtg ggg agc agc atc tac gtg      864
Ile Lys Gly Ser Gly Asn Arg Thr Ser Val Gly Ser Ser Ile Tyr Val
        275                 280                 285 aac acc ccc agc ggc tcc ctg gtg tcc tcc gag gcc cag ctg ttc aac      912
Asn Thr Pro Ser Gly Ser Leu Val Ser Ser Glu Ala Gln Leu Phe Asn
    290                 295                 300 aag ccc tac tgg ctg cag aag gcc cag ggc cac aac aac ggc atc tgt      960
Lys Pro Tyr Trp Leu Gln Lys Ala Gln Gly His Asn Asn Gly Ile Cys
305                 310                 315                 320 tgg ggc aac cag ctg ttc gtg acc gtg gtg gac acc acc cgc agc acc     1008
Trp Gly Asn Gln Leu Phe Val Thr Val Val Asp Thr Thr Arg Ser Thr
                325                 330                 335 aac atg acc ctg tgt gcc tcc gtg acc acc tcc tcc acc tac acc aac     1056
Asn Met Thr Leu Cys Ala Ser Val Thr Thr Ser Ser Thr Tyr Thr Asn
            340                 345                 350 tcc gac tac aag gag tac atg cgc cac gtg gag gag tac gac ctg cag     1104
Ser Asp Tyr Lys Glu Tyr Met Arg His Val Glu Glu Tyr Asp Leu Gln
        355                 360                 365 ttc atc ttc cag ctg tgt agc atc acc ctg tcc gcc gag gtg atg gcc     1152
Phe Ile Phe Gln Leu Cys Ser Ile Thr Leu Ser Ala Glu Val Met Ala
    370                 375                 380 tac atc cac acc atg aac ccc tcc gtg ctg gag gac tgg aac ttc ggg     1200
Tyr Ile His Thr Met Asn Pro Ser Val Leu Glu Asp Trp Asn Phe Gly
385                 390                 395                 400 ctg tcc ccc ccc ccc aac ggc acc ctg gag gac acc tac agg tac gtg     1248
Leu Ser Pro Pro Pro Asn Gly Thr Leu Glu Asp Thr Tyr Arg Tyr Val
                405                 410                 415 cag tcc cag gcc atc acc tgt cag aag ccc acc ccc gag aag gag aag     1296
Gln Ser Gln Ala Ile Thr Cys Gln Lys Pro Thr Pro Glu Lys Glu Lys
            420                 425                 430 ccc gac ccc tac aag aac ctg agc ttc tgg gag gtg aac ctg aag gag     1344
Pro Asp Pro Tyr Lys Asn Leu Ser Phe Trp Glu Val Asn Leu Lys Glu
        435                 440                 445 aag ttc tcc agc gag ctg gac cag tac ccc ctg ggc cgc aag ttc ctg     1392
Lys Phe Ser Ser Glu Leu Asp Gln Tyr Pro Leu Gly Arg Lys Phe Leu
    450                 455                 460 ctg cag agc cag gcc gag ccc gac cgc gcc cac tac aac atc gtc acc     1440
Leu Gln Ser Gln Ala Glu Pro Asp Arg Ala His Tyr Asn Ile Val Thr
465                 470                 475                 480 ttc aaa aaa taa                                                     1452
Phe Lys Lys <210> SEQ ID NO 20
<211> LENGTH: 483
<212> TYPE: PRT
<213> ORGANISM: Artificial Sequence
<220> FEATURE:
<223> OTHER INFORMATION: Polypeptide encoded by SEQ ID NO: 19
```

<400> SEQUENCE: 20

```
Met Trp Arg Pro Ser Asp Ser Thr Val Tyr Val Pro Pro Asn Pro
1               5                   10                  15

Val Ser Lys Val Val Ala Thr Asp Ala Tyr Val Thr Arg Thr Asn Ile
            20                  25                  30

Phe Tyr His Ala Ser Ser Arg Leu Leu Ala Val Gly His Pro Tyr
        35                  40                  45

Phe Phe Ile Lys Arg Ala Asn Lys Thr Val Val Pro Lys Val Ser Gly
        50                  55                  60

Tyr Gln Tyr Arg Val Phe Lys Val Val Leu Pro Asp Pro Asn Lys Phe
65                  70                  75                  80

Ala Leu Pro Asp Ser Ser Leu Phe Asp Pro Thr Thr Gln Arg Leu Val
                85                  90                  95

Trp Ala Cys Thr Gly Leu Glu Val Gly Arg Gly Gln Pro Leu Gly Val
            100                 105                 110

Gly Val Ser Gly His Pro Phe Leu Asn Lys Tyr Asp Asp Val Glu Asn
            115                 120                 125

Ser Gly Ser Gly Gly Asn Pro Gly Gln Asp Asn Arg Val Asn Val Gly
            130                 135                 140

Met Asp Tyr Lys Gln Thr Gln Leu Cys Met Val Gly Cys Ala Pro Pro
145                 150                 155                 160

Leu Cys Glu His Trp Gly Lys Gly Lys Gln Cys Thr Asn Thr Pro Val
                165                 170                 175

Gln Ala Gly Asp Cys Pro Pro Leu Glu Leu Ile Thr Ser Val Ile Gln
            180                 185                 190

Asp Gly Asp Met Val Asp Thr Gly Phe Gly Ala Met Asn Phe Ala Asp
            195                 200                 205

Leu Gln Thr Asn Lys Ser Asp Val Pro Ile Asp Ile Cys Gly Thr Thr
210                 215                 220

Cys Lys Tyr Pro Asp Tyr Leu Gln Met Ala Ala Asp Pro Tyr Gly Asp
225                 230                 235                 240

Arg Leu Phe Phe Phe Leu Arg Lys Glu Gln Met Phe Ala Arg His Phe
                245                 250                 255

Phe Asn Arg Ala Gly Glu Val Gly Glu Pro Val Pro Asp Thr Leu Ile
            260                 265                 270

Ile Lys Gly Ser Gly Asn Arg Thr Ser Val Gly Ser Ser Ile Tyr Val
            275                 280                 285

Asn Thr Pro Ser Gly Ser Leu Val Ser Ser Glu Ala Gln Leu Phe Asn
            290                 295                 300

Lys Pro Tyr Trp Leu Gln Lys Ala Gln Gly His Asn Asn Gly Ile Cys
305                 310                 315                 320

Trp Gly Asn Gln Leu Phe Val Thr Val Val Asp Thr Thr Arg Ser Thr
                325                 330                 335

Asn Met Thr Leu Cys Ala Ser Val Thr Thr Ser Ser Thr Tyr Thr Asn
            340                 345                 350

Ser Asp Tyr Lys Glu Tyr Met Arg His Val Glu Glu Tyr Asp Leu Gln
            355                 360                 365

Phe Ile Phe Gln Leu Cys Ser Ile Thr Leu Ser Ala Glu Val Met Ala
            370                 375                 380

Tyr Ile His Thr Met Asn Pro Ser Val Leu Glu Asp Trp Asn Phe Gly
385                 390                 395                 400

Leu Ser Pro Pro Pro Asn Gly Thr Leu Glu Asp Thr Tyr Arg Tyr Val
```

|  |  |  | 405 |  |  |  | 410 |  |  |  | 415 |  |  |
|---|---|---|---|---|---|---|---|---|---|---|---|---|---|
| Gln | Ser | Gln | Ala | Ile | Thr | Cys | Gln | Lys | Pro | Thr | Pro | Glu | Lys | Glu | Lys |
|  |  |  | 420 |  |  |  | 425 |  |  |  | 430 |  |  |

Pro Asp Pro Tyr Lys Asn Leu Ser Phe Trp Glu Val Asn Leu Lys Glu
        435                 440                 445

Lys Phe Ser Ser Glu Leu Asp Gln Tyr Pro Leu Gly Arg Lys Phe Leu
    450                 455                 460

Leu Gln Ser Gln Ala Glu Pro Asp Arg Ala His Tyr Asn Ile Val Thr
465                 470                 475                 480

Phe Lys Lys

<210> SEQ ID NO 21
<211> LENGTH: 1404
<212> TYPE: DNA
<213> ORGANISM: Bovine papillomavirus type 1
<220> FEATURE:
<221> NAME/KEY: CDS
<222> LOCATION: (1)..(1404)

<400> SEQUENCE: 21

```
atg agt gca cga aaa agg gtg aaa cgt gca aat gtc tat gac ctg tac      48
Met Ser Ala Arg Lys Arg Val Lys Arg Ala Asn Val Tyr Asp Leu Tyr
1               5                   10                  15 agg act tgc aag caa gcg ggc acc tgt cca cca gat gtg ata cct aag      96
Arg Thr Cys Lys Gln Ala Gly Thr Cys Pro Pro Asp Val Ile Pro Lys
            20                  25                  30 gta gaa ggt gac act ata gca gac aag att tta aaa tta gga ggc ctt     144
Val Glu Gly Asp Thr Ile Ala Asp Lys Ile Leu Lys Leu Gly Gly Leu
        35                  40                  45 gca att tat ctg ggg ggc cta ggt att gga aca tgg tct aca gga aga     192
Ala Ile Tyr Leu Gly Gly Leu Gly Ile Gly Thr Trp Ser Thr Gly Arg
    50                  55                  60 gtg gct gca gga gga tca cct agg tat gta ccc tta aga acc tct gga     240
Val Ala Ala Gly Gly Ser Pro Arg Tyr Val Pro Leu Arg Thr Ser Gly
65                  70                  75                  80 tcc act aca agc ctg gca tct gta gga tcc agg gct ggt gca gcc act     288
Ser Thr Thr Ser Leu Ala Ser Val Gly Ser Arg Ala Gly Ala Ala Thr
                85                  90                  95 ggc act cgc agc agc atc aca gga atc ccc ctt gac acc cta gaa act     336
Gly Thr Arg Ser Ser Ile Thr Gly Ile Pro Leu Asp Thr Leu Glu Thr
            100                 105                 110 att ggg gct ctt cgt cct gga gct tat gaa gac act gtg ctc cca gag     384
Ile Gly Ala Leu Arg Pro Gly Ala Tyr Glu Asp Thr Val Leu Pro Glu
        115                 120                 125 gcc cct gct att gtc acc cct gat gct gta cct gcg gac aca ggg ata     432
Ala Pro Ala Ile Val Thr Pro Asp Ala Val Pro Ala Asp Thr Gly Ile
    130                 135                 140 gat ggc ctt tct ata ggc act gac tct tcc act gaa act tta atc aca     480
Asp Gly Leu Ser Ile Gly Thr Asp Ser Ser Thr Glu Thr Leu Ile Thr
145                 150                 155                 160 ttg tta gag cct gag ggt cct gaa gac gtg gca gtc tta gag ctg caa     528
Leu Leu Glu Pro Glu Gly Pro Glu Asp Val Ala Val Leu Glu Leu Gln
                165                 170                 175 cct cta gac cat gca aat tgg caa gtt agc aat gct gtt cat cag ggc     576
Pro Leu Asp His Ala Asn Trp Gln Val Ser Asn Ala Val His Gln Gly
            180                 185                 190 tct gca tac cac gcc cct ctg cag ctg cag tcc tcc att gca gaa aca     624
Ser Ala Tyr His Ala Pro Leu Gln Leu Gln Ser Ser Ile Ala Glu Thr
        195                 200                 205
```

| | | | | | | | | | | | | | | | | |
|---|---|---|---|---|---|---|---|---|---|---|---|---|---|---|---|---|
| tct | gga | cta | gaa | aat | att | ttt | gta | gga | ggg | gct | ggg | tta | ggg | gat | aca | 672 |
| Ser | Gly | Leu | Glu | Asn | Ile | Phe | Val | Gly | Gly | Ala | Gly | Leu | Gly | Asp | Thr | |
| | 210 | | | | 215 | | | | | 220 | | | | | | |
| ggc | gga | gag | aac | ata | gag | ctc | aca | ttt | ttt | ggt | tcc | cca | cgc | aca | agt | 720 |
| Gly | Gly | Glu | Asn | Ile | Glu | Leu | Thr | Phe | Phe | Gly | Ser | Pro | Arg | Thr | Ser | |
| 225 | | | | | 230 | | | | | 235 | | | | | 240 | |
| acc | ccc | cgt | aac | ctg | cct | caa | act | gca | cgg | ggc | atc | ttg | aac | tgg | ttt | 768 |
| Thr | Pro | Arg | Asn | Leu | Pro | Gln | Thr | Ala | Arg | Gly | Ile | Leu | Asn | Trp | Phe | |
| | | | | 245 | | | | | 250 | | | | | 255 | | |
| agc | aaa | aga | tac | tac | aca | caa | ata | ccc | aca | gaa | gac | cct | gat | gtc | ttt | 816 |
| Ser | Lys | Arg | Tyr | Tyr | Thr | Gln | Ile | Pro | Thr | Glu | Asp | Pro | Asp | Val | Phe | |
| | | | 260 | | | | | 265 | | | | | 270 | | | |
| tca | tca | cag | aca | ttt | tca | aac | cca | gtg | tat | gat | cct | gag | cct | gca | gtg | 864 |
| Ser | Ser | Gln | Thr | Phe | Ser | Asn | Pro | Val | Tyr | Asp | Pro | Glu | Pro | Ala | Val | |
| | | | 275 | | | | | 280 | | | | | 285 | | | |
| cta | aaa | ggt | ccc | agt | ggc | cgt | gtg | ggg | cta | agc | caa | gtg | tat | agg | cct | 912 |
| Leu | Lys | Gly | Pro | Ser | Gly | Arg | Val | Gly | Leu | Ser | Gln | Val | Tyr | Arg | Pro | |
| | 290 | | | | | 295 | | | | | 300 | | | | | |
| gac | tat | att | gaa | aca | cgg | ggt | ggg | ggt | cag | gtg | ggc | cca | cag | ctg | cat | 960 |
| Asp | Tyr | Ile | Glu | Thr | Arg | Gly | Gly | Gly | Gln | Val | Gly | Pro | Gln | Leu | His | |
| 305 | | | | | 310 | | | | | 315 | | | | | 320 | |
| gtc | agg | tac | tcc | tta | agc | act | atc | aca | gaa | gat | gtg | gaa | gcc | ata | cct | 1008 |
| Val | Arg | Tyr | Ser | Leu | Ser | Thr | Ile | Thr | Glu | Asp | Val | Glu | Ala | Ile | Pro | |
| | | | | 325 | | | | | 330 | | | | | 335 | | |
| ata | gca | gtt | gat | gaa | gac | aca | caa | ggg | cta | gca | ttt | ctt | cct | tta | cat | 1056 |
| Ile | Ala | Val | Asp | Glu | Asp | Thr | Gln | Gly | Leu | Ala | Phe | Leu | Pro | Leu | His | |
| | | | 340 | | | | | 345 | | | | | 350 | | | |
| gaa | gaa | cca | ggg | gac | ttt | gaa | gaa | att | gag | cta | gat | gat | tta | ggt | gaa | 1104 |
| Glu | Glu | Pro | Gly | Asp | Phe | Glu | Glu | Ile | Glu | Leu | Asp | Asp | Leu | Gly | Glu | |
| | | | 355 | | | | | 360 | | | | | 365 | | | |
| gag | cac | gcc | ttg | ctc | ccc | aag | tca | tct | act | gca | cct | att | ggt | agt | gga | 1152 |
| Glu | His | Ala | Leu | Leu | Pro | Lys | Ser | Ser | Thr | Ala | Pro | Ile | Gly | Ser | Gly | |
| | 370 | | | | | 375 | | | | | 380 | | | | | |
| gtt | cgt | agg | gcg | ctc | att | cca | ggt | caa | ggc | ttc | agt | gca | aca | cgg | ccc | 1200 |
| Val | Arg | Arg | Ala | Leu | Ile | Pro | Gly | Gln | Gly | Phe | Ser | Ala | Thr | Arg | Pro | |
| 385 | | | | | 390 | | | | | 395 | | | | | 400 | |
| aca | ggt | gtg | gta | acc | tat | ggc | tca | cct | gac | atg | tac | cct | gct | agc | cct | 1248 |
| Thr | Gly | Val | Val | Thr | Tyr | Gly | Ser | Pro | Asp | Met | Tyr | Pro | Ala | Ser | Pro | |
| | | | | 405 | | | | | 410 | | | | | 415 | | |
| gtt | ggc | cct | gac | tcg | aca | tcc | cct | agc | cta | gtt | att | gat | gac | aac | aca | 1296 |
| Val | Gly | Pro | Asp | Ser | Thr | Ser | Pro | Ser | Leu | Val | Ile | Asp | Asp | Asn | Thr | |
| | | | 420 | | | | | 425 | | | | | 430 | | | |
| aca | aca | cca | ata | atc | att | att | gat | ggc | cac | aca | gtg | gat | ctg | tat | agc | 1344 |
| Thr | Thr | Pro | Ile | Ile | Ile | Ile | Asp | Gly | His | Thr | Val | Asp | Leu | Tyr | Ser | |
| | | | 435 | | | | | 440 | | | | | 445 | | | |
| aat | aac | tat | agc | ttg | cat | ccc | tcc | ttg | ttg | agg | aaa | aga | aaa | aaa | cgg | 1392 |
| Asn | Asn | Tyr | Ser | Leu | His | Pro | Ser | Leu | Leu | Arg | Lys | Arg | Lys | Lys | Arg | |
| | 450 | | | | | 455 | | | | | 460 | | | | | |
| aaa | cat | gcc | taa | | | | | | | | | | | | | 1404 |
| Lys | His | Ala | | | | | | | | | | | | | | |
| 465 | | | | | | | | | | | | | | | | |

<210> SEQ ID NO 22
<211> LENGTH: 467
<212> TYPE: PRT
<213> ORGANISM: Bovine papillomavirus type 1

<400> SEQUENCE: 22

Met Ser Ala Arg Lys Arg Val Lys Arg Ala Asn Val Tyr Asp Leu Tyr
1               5                   10                  15

-continued

```
Arg Thr Cys Lys Gln Ala Gly Thr Cys Pro Pro Asp Val Ile Pro Lys
             20                  25                  30

Val Glu Gly Asp Thr Ile Ala Asp Lys Ile Leu Lys Leu Gly Gly Leu
         35                  40                  45

Ala Ile Tyr Leu Gly Gly Leu Gly Ile Gly Thr Trp Ser Thr Gly Arg
     50                  55                  60

Val Ala Ala Gly Gly Ser Pro Arg Tyr Val Pro Leu Arg Thr Ser Gly
 65                  70                  75                  80

Ser Thr Thr Ser Leu Ala Ser Val Gly Ser Arg Ala Gly Ala Ala Thr
                 85                  90                  95

Gly Thr Arg Ser Ser Ile Thr Gly Ile Pro Leu Asp Thr Leu Glu Thr
            100                 105                 110

Ile Gly Ala Leu Arg Pro Gly Ala Tyr Glu Asp Thr Val Leu Pro Glu
        115                 120                 125

Ala Pro Ala Ile Val Thr Pro Asp Ala Val Pro Ala Asp Thr Gly Ile
    130                 135                 140

Asp Gly Leu Ser Ile Gly Thr Asp Ser Ser Thr Glu Thr Leu Ile Thr
145                 150                 155                 160

Leu Leu Glu Pro Glu Gly Pro Glu Asp Val Ala Val Leu Glu Leu Gln
                165                 170                 175

Pro Leu Asp His Ala Asn Trp Gln Val Ser Asn Ala Val His Gln Gly
            180                 185                 190

Ser Ala Tyr His Ala Pro Leu Gln Leu Gln Ser Ser Ile Ala Glu Thr
        195                 200                 205

Ser Gly Leu Glu Asn Ile Phe Val Gly Ala Gly Leu Gly Asp Thr
    210                 215                 220

Gly Gly Glu Asn Ile Glu Leu Thr Phe Phe Gly Ser Pro Arg Thr Ser
225                 230                 235                 240

Thr Pro Arg Asn Leu Pro Gln Thr Ala Arg Gly Ile Leu Asn Trp Phe
                245                 250                 255

Ser Lys Arg Tyr Tyr Thr Gln Ile Pro Thr Glu Asp Pro Asp Val Phe
            260                 265                 270

Ser Ser Gln Thr Phe Ser Asn Pro Val Tyr Asp Pro Glu Pro Ala Val
        275                 280                 285

Leu Lys Gly Pro Ser Gly Arg Val Gly Leu Ser Gln Val Tyr Arg Pro
    290                 295                 300

Asp Tyr Ile Glu Thr Arg Gly Gly Gln Val Gly Pro Gln Leu His
305                 310                 315                 320

Val Arg Tyr Ser Leu Ser Thr Ile Thr Glu Asp Val Glu Ala Ile Pro
                325                 330                 335

Ile Ala Val Asp Glu Asp Thr Gln Gly Leu Ala Phe Leu Pro Leu His
            340                 345                 350

Glu Glu Pro Gly Asp Phe Glu Glu Ile Glu Leu Asp Asp Leu Gly Glu
        355                 360                 365

Glu His Ala Leu Leu Pro Lys Ser Ser Thr Ala Pro Ile Gly Ser Gly
    370                 375                 380

Val Arg Arg Ala Leu Ile Pro Gly Gln Gly Phe Ser Ala Thr Arg Pro
385                 390                 395                 400

Thr Gly Val Val Thr Tyr Gly Ser Pro Asp Met Tyr Pro Ala Ser Pro
                405                 410                 415

Val Gly Pro Asp Ser Thr Ser Pro Ser Leu Val Ile Asp Asp Asn Thr
            420                 425                 430

Thr Thr Pro Ile Ile Ile Ile Asp Gly His Thr Val Asp Leu Tyr Ser
```

-continued

```
                435                 440                 445
Asn Asn Tyr Ser Leu His Pro Ser Leu Leu Arg Lys Arg Lys Lys Arg
    450                 455                 460

Lys His Ala
465

<210> SEQ ID NO 23
<211> LENGTH: 1410
<212> TYPE: DNA
<213> ORGANISM: Artificial Sequence
<220> FEATURE:
<223> OTHER INFORMATION: Synthetic BPV type 1 construct humanised
<220> FEATURE:
<221> NAME/KEY: CDS
<222> LOCATION: (1)..(1410)

<400> SEQUENCE: 23 atg agc gcc cgc aag aga gtg aag cgc gcc agc gcc tac gac ctg tac      48
Met Ser Ala Arg Lys Arg Val Lys Arg Ala Ser Ala Tyr Asp Leu Tyr
1               5                   10                  15 agg acc tgc aag cag gcc ggc aca tgt cca cca gat gtg atc cga aag      96
Arg Thr Cys Lys Gln Ala Gly Thr Cys Pro Pro Asp Val Ile Arg Lys
            20                  25                  30 gtg gag ggc gac acc atc gcc gac aag atc ctg aag ttc ggc ggc ctg     144
Val Glu Gly Asp Thr Ile Ala Asp Lys Ile Leu Lys Phe Gly Gly Leu
        35                  40                  45 gcc atc tac ctg ggc ggc ctg ggc atc gga aca tgg tct acc ggc agg     192
Ala Ile Tyr Leu Gly Gly Leu Gly Ile Gly Thr Trp Ser Thr Gly Arg
    50                  55                  60 gtg gcc gcc ggc ggc tca cca agg tac acc cca ctg cgc acc gcc ggc     240
Val Ala Ala Gly Gly Ser Pro Arg Tyr Thr Pro Leu Arg Thr Ala Gly
65                  70                  75                  80 tcc acc tcc tcc ctg gcc tcc atc gga tcc aga gcc gtg acc gcc ggg     288
Ser Thr Ser Ser Leu Ala Ser Ile Gly Ser Arg Ala Val Thr Ala Gly
                85                  90                  95 acc cgc ccc tcc atc ggc gcg ggc atc cct ctg gac acc ctg gaa act     336
Thr Arg Pro Ser Ile Gly Ala Gly Ile Pro Leu Asp Thr Leu Glu Thr
            100                 105                 110 ctt ggg gcc ctg cgc cct ggc gtg tac gag gac acc gtg ctg ccc gaa     384
Leu Gly Ala Leu Arg Pro Gly Val Tyr Glu Asp Thr Val Leu Pro Glu
        115                 120                 125 gcc cct gcc atc gtg acc cct gac gcc gtg cct gca gac tcc ggc ctg     432
Ala Pro Ala Ile Val Thr Pro Asp Ala Val Pro Ala Asp Ser Gly Leu
    130                 135                 140 gac gcc ctg tcc atc ggc aca gac tcc tcc acc gag acc ctg atc acc     480
Asp Ala Leu Ser Ile Gly Thr Asp Ser Ser Thr Glu Thr Leu Ile Thr
145                 150                 155                 160 ctg ctg gag cct gag ggc ccc gaa gac ata gcc gtg ctg gaa ctc cag     528
Leu Leu Glu Pro Glu Gly Pro Glu Asp Ile Ala Val Leu Glu Leu Gln
                165                 170                 175 ccc ctg gac cgc cca acc tgg cag gtg agc aat gct gtg cac cag tcc     576
Pro Leu Asp Arg Pro Thr Trp Gln Val Ser Asn Ala Val His Gln Ser
            180                 185                 190 tct gcc tac cac gcc cct ctc cag ctg caa tcc tcc atc gcc gag aca     624
Ser Ala Tyr His Ala Pro Leu Gln Leu Gln Ser Ser Ile Ala Glu Thr
        195                 200                 205 tct ggt tta gaa aat att ttt gta gga ggc tcg ggt tta ggg gat acc     672
Ser Gly Leu Glu Asn Ile Phe Val Gly Gly Ser Gly Leu Gly Asp Thr
    210                 215                 220 ggc ggc gag aac atc gag ctg acc tac ttc ggc tcc ccc cgc acc agc     720
Gly Gly Glu Asn Ile Glu Leu Thr Tyr Phe Gly Ser Pro Arg Thr Ser
```

```
acc ccc cgc tcc atc gcc tcc aag tcc cgc ggc atc ctg aac tgg ttc        768
Thr Pro Arg Ser Ile Ala Ser Lys Ser Arg Gly Ile Leu Asn Trp Phe
            245                 250                 255 agc aag cgg tac tac acc cag gtg ccc acc gaa gat ccc gaa gtg ttc        816
Ser Lys Arg Tyr Tyr Thr Gln Val Pro Thr Glu Asp Pro Glu Val Phe
        260                 265                 270 tcc tcc cag acc ttc gcc aac ccc ctg tac gag gcc gag ccc gcc gtg        864
Ser Ser Gln Thr Phe Ala Asn Pro Leu Tyr Glu Ala Glu Pro Ala Val
    275                 280                 285 ctg aag ggc cct agc ggc cgc gtg ggc ctg tcc cag gtg tac aag cct        912
Leu Lys Gly Pro Ser Gly Arg Val Gly Leu Ser Gln Val Tyr Lys Pro
290                 295                 300 gat acc ctg acc aca cgt agc ggc aca gag gtg ggc ccc cag ctg cat        960
Asp Thr Leu Thr Thr Arg Ser Gly Thr Glu Val Gly Pro Gln Leu His
305                 310                 315                 320 gtg agg tac tcc ctg tcc acc atc cat gag gat gtg gag gct atc ccc       1008
Val Arg Tyr Ser Leu Ser Thr Ile His Glu Asp Val Glu Ala Ile Pro
                325                 330                 335 tac acc gtg gat gag aac acc cag ggc ctg gcc ttc gtg ccc ctg cat       1056
Tyr Thr Val Asp Glu Asn Thr Gln Gly Leu Ala Phe Val Pro Leu His
            340                 345                 350 gag gag cag gcc ggc ttc gag gag atc gag ctc gac gat ttc agc gag       1104
Glu Glu Gln Ala Gly Phe Glu Glu Ile Glu Leu Asp Asp Phe Ser Glu
        355                 360                 365 acc cat cgc ctg ctg ccc cag aac acc tcc tcc acc ccc gtg ggc agc       1152
Thr His Arg Leu Leu Pro Gln Asn Thr Ser Ser Thr Pro Val Gly Ser
    370                 375                 380 ggc gtg cgc aga agc ctg atc cct acc cga gag ttc agc gcc acc cgg       1200
Gly Val Arg Arg Ser Leu Ile Pro Thr Arg Glu Phe Ser Ala Thr Arg
385                 390                 395                 400 cct acc ggc gtg gtg acc tac ggc tcc ccc gac acc tac tcc gct agc       1248
Pro Thr Gly Val Val Thr Tyr Gly Ser Pro Asp Thr Tyr Ser Ala Ser
                405                 410                 415 ccc gtg acc gac cct gat tct acc tct cct agc ctg gtg atc gac gac       1296
Pro Val Thr Asp Pro Asp Ser Thr Ser Pro Ser Leu Val Ile Asp Asp
            420                 425                 430 acc acc acc ccc atc atc atc atc gac ggc cac aca gtg gat ctg           1344
Thr Thr Thr Pro Ile Ile Ile Ile Asp Gly His Thr Val Asp Leu
        435                 440                 445 tac agc agc aac tac acc ctg cat ccc tcc ctg ctg agg aag cgc aag       1392
Tyr Ser Ser Asn Tyr Thr Leu His Pro Ser Leu Leu Arg Lys Arg Lys
    450                 455                 460 aag cgc aag cat gcc taa                                                1410
Lys Arg Lys His Ala
465

<210> SEQ ID NO 24
<211> LENGTH: 469
<212> TYPE: PRT
<213> ORGANISM: Artificial Sequence
<220> FEATURE:
<223> OTHER INFORMATION: Polypeptide encoded by SEQ ID NO: 23

<400> SEQUENCE: 24

Met Ser Ala Arg Lys Arg Val Lys Arg Ala Ser Ala Tyr Asp Leu Tyr
1               5                   10                  15

Arg Thr Cys Lys Gln Ala Gly Thr Cys Pro Pro Asp Val Ile Arg Lys
            20                  25                  30

Val Glu Gly Asp Thr Ile Ala Asp Lys Ile Leu Lys Phe Gly Gly Leu
```

-continued

```
             35                  40                  45
Ala Ile Tyr Leu Gly Gly Leu Gly Ile Gly Thr Trp Ser Thr Gly Arg
 50                  55                  60
Val Ala Ala Gly Gly Ser Pro Arg Tyr Thr Pro Leu Arg Thr Ala Gly
 65                  70                  75                  80
Ser Thr Ser Ser Leu Ala Ser Ile Gly Ser Arg Ala Val Thr Ala Gly
                 85                  90                  95
Thr Arg Pro Ser Ile Gly Ala Gly Ile Pro Leu Asp Thr Leu Glu Thr
                100                 105                 110
Leu Gly Ala Leu Arg Pro Gly Val Tyr Glu Asp Thr Val Leu Pro Glu
                115                 120                 125
Ala Pro Ala Ile Val Thr Pro Asp Ala Val Pro Ala Asp Ser Gly Leu
130                 135                 140
Asp Ala Leu Ser Ile Gly Thr Asp Ser Ser Thr Glu Thr Leu Ile Thr
145                 150                 155                 160
Leu Leu Glu Pro Glu Gly Pro Glu Asp Ile Ala Val Leu Glu Leu Gln
                165                 170                 175
Pro Leu Asp Arg Pro Thr Trp Gln Val Ser Asn Ala Val His Gln Ser
                180                 185                 190
Ser Ala Tyr His Ala Pro Leu Gln Leu Gln Ser Ser Ile Ala Glu Thr
                195                 200                 205
Ser Gly Leu Glu Asn Ile Phe Val Gly Gly Ser Gly Leu Gly Asp Thr
                210                 215                 220
Gly Gly Glu Asn Ile Glu Leu Thr Tyr Phe Gly Ser Pro Arg Thr Ser
225                 230                 235                 240
Thr Pro Arg Ser Ile Ala Ser Lys Ser Arg Gly Ile Leu Asn Trp Phe
                245                 250                 255
Ser Lys Arg Tyr Tyr Thr Gln Val Pro Thr Glu Asp Pro Glu Val Phe
                260                 265                 270
Ser Ser Gln Thr Phe Ala Asn Pro Leu Tyr Glu Ala Glu Pro Ala Val
                275                 280                 285
Leu Lys Gly Pro Ser Gly Arg Val Gly Leu Ser Gln Val Tyr Lys Pro
                290                 295                 300
Asp Thr Leu Thr Thr Arg Ser Gly Thr Glu Val Gly Pro Gln Leu His
305                 310                 315                 320
Val Arg Tyr Ser Leu Ser Thr Ile His Glu Asp Val Glu Ala Ile Pro
                325                 330                 335
Tyr Thr Val Asp Glu Asn Thr Gln Gly Leu Ala Phe Val Pro Leu His
                340                 345                 350
Glu Glu Gln Ala Gly Phe Glu Glu Ile Glu Leu Asp Asp Phe Ser Glu
                355                 360                 365
Thr His Arg Leu Leu Pro Gln Asn Thr Ser Ser Thr Pro Val Gly Ser
                370                 375                 380
Gly Val Arg Arg Ser Leu Ile Pro Thr Arg Glu Phe Ser Ala Thr Arg
385                 390                 395                 400
Pro Thr Gly Val Val Thr Tyr Gly Ser Pro Asp Thr Tyr Ser Ala Ser
                405                 410                 415
Pro Val Thr Asp Pro Asp Ser Ser Pro Ser Leu Val Ile Asp Asp
                420                 425                 430
Thr Thr Thr Thr Pro Ile Ile Ile Ile Asp Gly His Thr Val Asp Leu
                435                 440                 445
Tyr Ser Ser Asn Tyr Thr Leu His Pro Ser Leu Leu Arg Lys Arg Lys
                450                 455                 460
```

Lys Arg Lys His Ala
465

<210> SEQ ID NO 25
<211> LENGTH: 5
<212> TYPE: PRT
<213> ORGANISM: Artificial Sequence
<220> FEATURE:
<223> OTHER INFORMATION: Ornithine decarboxylase hydrophobic
      pentapeptide motif

<400> SEQUENCE: 25

Ala Arg Ile Asn Val
1               5

<210> SEQ ID NO 26
<211> LENGTH: 11
<212> TYPE: PRT
<213> ORGANISM: Artificial Sequence
<220> FEATURE:
<223> OTHER INFORMATION: Hydrophobic motif found in C-terminal tags of
      aberrant polypeptides

<400> SEQUENCE: 26

Ala Ala Asn Asp Glu Asn Tyr Ala Leu Ala Ala
1               5                   10

<210> SEQ ID NO 27
<211> LENGTH: 9
<212> TYPE: PRT
<213> ORGANISM: Artificial Sequence
<220> FEATURE:
<223> OTHER INFORMATION: Rapid intracellular degradation motif
<220> FEATURE:
<221> NAME/KEY: MISC_FEATURE
<222> LOCATION: (2)..(2)
<223> OTHER INFORMATION: X= any amino acid
<220> FEATURE:
<221> NAME/KEY: MISC_FEATURE
<222> LOCATION: (6)..(6)
<223> OTHER INFORMATION: X= any amino acid
<220> FEATURE:
<221> NAME/KEY: MISC_FEATURE
<222> LOCATION: (8)..(8)
<223> OTHER INFORMATION: X= any amino acid

<400> SEQUENCE: 27

Arg Xaa Ala Leu Gly Xaa Ile Xaa Asn
1               5

<210> SEQ ID NO 28
<211> LENGTH: 10
<212> TYPE: PRT
<213> ORGANISM: Artificial Sequence
<220> FEATURE:
<223> OTHER INFORMATION: Cyclin rapid intracellular degradation

<400> SEQUENCE: 28

Lys Thr Lys Arg Asn Tyr Ser Ala Arg Asp
1               5                   10

<210> SEQ ID NO 29
<211> LENGTH: 9
<212> TYPE: PRT
<213> ORGANISM: Artificial Sequence
<220> FEATURE:
<223> OTHER INFORMATION: polypeptide corresponding to the minimal H-2 Db
      CTL epitope of HPV16

```
<400> SEQUENCE: 29

Arg Ala His Tyr Asn Ile Val Thr Phe
1               5
```